US007687057B2

(12) United States Patent
Mitrani

(10) Patent No.: US 7,687,057 B2
(45) Date of Patent: *Mar. 30, 2010

(54) IN VITRO MICRO-ORGANS, AND USES RELATED THERETO

(75) Inventor: Eduardo N. Mitrani, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 745 days.

This patent is subject to a terminal disclaimer.

(21) Appl. No.: 10/320,717

(22) Filed: Dec. 17, 2002

(65) Prior Publication Data

US 2003/0152561 A1 Aug. 14, 2003

Related U.S. Application Data

(63) Continuation of application No. 09/589,736, filed on Jun. 9, 2000, now abandoned, which is a continuation-in-part of application No. 09/425,233, filed on Oct. 25, 1999, now Pat. No. 6,472,200, which is a continuation-in-part of application No. 09/341,630, filed as application No. PCT/US98/00594 on Jan. 9, 1998, now Pat. No. 6,372,482.

(51) Int. Cl.
*A01N 63/00* (2006.01)
*A61K 48/00* (2006.01)

(52) U.S. Cl. ................ 424/93.2; 424/93.1; 424/93.21; 435/1.1; 435/320.1; 435/325

(58) Field of Classification Search ................ 435/325; 424/93.1

See application file for complete search history.

(56) References Cited

U.S. PATENT DOCUMENTS

| | | | |
|---|---|---|---|
| 1,516,071 A | 11/1924 | Apolant |
| 3,076,461 A | 2/1963 | Meek et al. |
| 3,470,782 A | 10/1969 | Acker |
| 3,613,242 A | 10/1971 | Hill et al. |
| 3,734,851 A | 5/1973 | Matsumura |
| 3,791,932 A | 2/1974 | Schuurs et al. |
| 3,839,153 A | 10/1974 | Schuurs et al. |
| 3,846,846 A | 11/1974 | Fischer |
| 3,850,578 A | 11/1974 | McConnell et al. |
| 3,850,752 A | 11/1974 | Schuurs et al. |
| 3,853,987 A | 12/1974 | Dreyer |
| 3,867,517 A | 2/1975 | Ling |
| 3,867,728 A | 2/1975 | Stubstad et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,043,343 A | 8/1977 | Williams |
| 4,098,876 A | 7/1978 | Piaso et al. |
| 4,115,346 A | 9/1978 | Gross et al. |
| 4,353,888 A | 10/1982 | Sefton |
| 4,369,788 A | 1/1983 | Goald |
| 4,391,909 A | 7/1983 | Lim |
| 4,475,856 A | 10/1984 | Toomingas |
| 4,498,778 A | 2/1985 | White |
| 4,533,635 A | 8/1985 | Guédon born Saglier et al. |
| 4,666,828 A | 5/1987 | Gusella |
| 4,683,202 A | 7/1987 | Mullis |
| 4,736,866 A | 4/1988 | Leder et al. |
| 4,798,885 A | 1/1989 | Mason et al. |
| 4,801,531 A | 1/1989 | Frossard |
| 4,835,102 A | 5/1989 | Bell et al. |
| 4,879,219 A | 11/1989 | Wands et al. |
| 4,883,666 A | 11/1989 | Sabel et al. |
| 4,888,291 A | 12/1989 | Barrandon et al. |
| 4,892,538 A | 1/1990 | Aebischer |
| 4,940,666 A | 7/1990 | Boyce et al. |
| 4,951,684 A | 8/1990 | McMillan |
| 4,966,849 A | 10/1990 | Vallee et al. |
| 4,973,301 A | 11/1990 | Nissenkorn |
| 5,011,771 A | 4/1991 | Bellet et al. |
| 5,012,066 A | 4/1991 | Matsutani et al. |
| 5,024,841 A | 6/1991 | Chu et al. |
| 5,032,508 A | 7/1991 | Naughton et al. |
| 5,059,193 A | 10/1991 | Kuslich |
| 5,106,627 A | 4/1992 | Aebischer |
| 5,175,383 A | 12/1992 | Leder et al. |
| 5,175,384 A | 12/1992 | Krimpenfort et al. |
| 5,175,385 A | 12/1992 | Wagner et al. |

(Continued)

FOREIGN PATENT DOCUMENTS

CA 2279996 8/1999

(Continued)

OTHER PUBLICATIONS

Wang et al, PNAS 1997;94:219-226.*

(Continued)

*Primary Examiner*—Q. Janice Li
(74) *Attorney, Agent, or Firm*—Pearl Cohen Zedek Latzer, LLP; Mark Cohen

(57) ABSTRACT

A method of delivering a gene product to a recipient, the method comprises (a) providing a micro-organ explant expressing at least one recombinant gene product, the micro-organ explant comprising a population of cells, the micro-organ explant maintaining a microarchitecture and a three dimensional structure of an organ from which it is obtained and at the same time having dimensions selected so as to allow diffusion of adequate nutrients and gases to cells in the micro-organ explant and diffusion of cellular waste out of the micro-organ explant so as to minimize cellular toxicity and concomitant death due to insufficient nutrition and accumulation of the waste in the micro-organ explant, at least some of the cells of the population of cells of the micro-organ explant expressing at least one recombinant gene product; and (b) implanting the micro-organ explant in the recipient.

25 Claims, 18 Drawing Sheets

U.S. PATENT DOCUMENTS

| | | | |
|---|---|---|---|
| 5,192,659 A | 3/1993 | Simons | |
| 5,209,753 A | 5/1993 | Biedermann et al. | |
| 5,221,778 A | 6/1993 | Byrne et al. | |
| 5,236,445 A | 8/1993 | Hayhurst et al. | |
| 5,266,480 A * | 11/1993 | Naughton et al. | 435/371 |
| 5,268,001 A | 12/1993 | Nicholson et al. | |
| 5,272,057 A | 12/1993 | Smulson et al. | |
| 5,281,521 A | 1/1994 | Trojanowski et al. | |
| 5,282,859 A | 2/1994 | Eisenberg | |
| 5,288,846 A | 2/1994 | Quertermous et al. | |
| 5,292,655 A | 3/1994 | Wille, Jr. | |
| 5,298,422 A | 3/1994 | Schwartz et al. | |
| 5,333,951 A | 8/1994 | Wakoh | |
| 5,347,075 A | 9/1994 | Sorge | |
| 5,360,735 A | 11/1994 | Weinshank et al. | |
| 5,376,123 A | 12/1994 | Klaue et al. | |
| 5,387,576 A | 2/1995 | Mitrani | |
| 5,387,742 A | 2/1995 | Cordell | |
| 5,423,850 A | 6/1995 | Berger | |
| 5,464,764 A | 11/1995 | Capecchi et al. | |
| 5,480,400 A | 1/1996 | Berger | |
| 5,487,992 A | 1/1996 | Capecchi et al. | |
| 5,491,692 A | 2/1996 | Gunner et al. | |
| 5,516,680 A | 5/1996 | Naughton et al. | |
| 5,518,498 A | 5/1996 | Lindenberg et al. | |
| 5,550,316 A | 8/1996 | Mintz | |
| 5,578,035 A | 11/1996 | Lin | |
| 5,658,310 A | 8/1997 | Berger | |
| 5,670,148 A | 9/1997 | Sherwin et al. | |
| 5,720,753 A | 2/1998 | Sander et al. | |
| 5,725,529 A | 3/1998 | Nicholson et al. | |
| 5,753,612 A | 5/1998 | Mitrani | |
| 5,759,830 A | 6/1998 | Vacanti et al. | |
| 5,782,830 A | 7/1998 | Farris | |
| 5,827,289 A | 10/1998 | Reiley et al. | |
| 5,861,313 A | 1/1999 | Pang et al. | |
| 5,871,767 A | 2/1999 | Dionne et al. | |
| 5,885,971 A | 3/1999 | German et al. | |
| 5,888,720 A | 3/1999 | Mitrani | |
| 5,911,721 A | 6/1999 | Nicholson et al. | |
| 5,958,764 A * | 9/1999 | Roop et al. | 435/320.1 |
| 5,968,044 A | 10/1999 | Nicholson et al. | |
| 5,972,015 A | 10/1999 | Scribner et al. | |
| 5,980,887 A | 11/1999 | Isner et al. | |
| 6,001,647 A | 12/1999 | Peek et al. | |
| 6,030,833 A | 2/2000 | Seebach et al. | |
| 6,036,657 A | 3/2000 | Milliman et al. | |
| 6,071,284 A | 6/2000 | Fox | |
| 6,168,597 B1 | 1/2001 | Biedermann et al. | |
| 6,197,575 B1 | 3/2001 | Griffith et al. | |
| 6,245,101 B1 | 6/2001 | Drasler et al. | |
| 6,248,110 B1 | 6/2001 | Reiley et al. | |
| 6,264,659 B1 | 7/2001 | Ross et al. | |
| 6,303,136 B1 | 10/2001 | Li et al. | |
| 6,372,482 B1 | 4/2002 | Mitrani | |
| 6,472,200 B1 | 10/2002 | Mitrani | |
| 6,979,341 B2 | 12/2005 | Scribner et al. | |
| 7,041,634 B2 * | 5/2006 | Weber et al. | 514/2 |
| 2002/0012661 A1 | 1/2002 | Saito et al. | |
| 2002/0039786 A1 | 4/2002 | Reid et al. | |
| 2002/0068880 A1 | 6/2002 | Burbank et al. | |
| 2002/0154114 A1 | 10/2002 | Christensen et al. | |
| 2003/0086914 A1 | 5/2003 | Mitrani | |
| 2003/0129736 A1 | 7/2003 | Mitrani | |
| 2003/0152561 A1 | 8/2003 | Mitrani | |
| 2003/0152562 A1 | 8/2003 | Mitrani | |
| 2003/0152909 A1 | 8/2003 | Mitrani | |
| 2003/0157074 A1 | 8/2003 | Mitrani | |

FOREIGN PATENT DOCUMENTS

| | | |
|---|---|---|
| DE | 2939057 | 4/1981 |
| DE | 3432897 | 3/1986 |
| DE | 4104092 | 8/1991 |
| EP | 222491 | 5/1987 |
| EP | 271211 | 6/1988 |
| EP | 361957 | 4/1990 |
| EP | 0364306 | 4/1990 |
| EP | 418035 | 3/1991 |
| EP | 0357958 | 5/1993 |
| EP | 0895380 | 3/1998 |
| GB | 408668 | 4/1934 |
| JP | 11-76399 | 3/1999 |
| JP | 2000-125863 | 5/2000 |
| WO | WO 91/12334 | 8/1991 |
| WO | WO 93/14200 | 7/1993 |
| WO | WO 93/22430 | 11/1993 |
| WO | WO 94/06908 | 3/1994 |
| WO | WO 94/28123 | 8/1994 |
| WO | WO 94/23049 | 10/1994 |
| WO | WO 96/30492 | 3/1996 |
| WO | WO 96/15225 | 5/1996 |
| WO | WO 97/15655 | 1/1997 |
| WO | WO 97/27742 | 7/1997 |
| WO | WO 98/54301 | 3/1998 |
| WO | WO 98/15575 | 4/1998 |
| WO | WO 98/16158 | 4/1998 |
| WO | WO 98/25964 | 6/1998 |
| WO | WO 98/39035 | 9/1998 |
| WO | WO 99/06073 | 2/1999 |
| WO | WO 99/49807 | 7/1999 |
| WO | WO 99/39661 | 8/1999 |
| WO | WO 00/09668 | 2/2000 |
| WO | WO 00/53795 | 9/2000 |
| WO | WO 01/07098 | 1/2001 |
| WO | WO 01/00859 | 4/2001 |
| WO | WO 01/23541 | 5/2001 |
| WO | WO 03/035851 | 1/2003 |
| WO | WO 03/039382 | 5/2003 |
| WO | WO 03/040686 | 5/2003 |
| WO | WO 03/049626 | 6/2003 |
| WO | WO 03/049783 | 6/2003 |
| WO | WO 2004/006831 | 1/2004 |
| WO | WO 2004/078916 | 9/2004 |

OTHER PUBLICATIONS

Hortelano et al, Blood 1996;87:5095-5103.*
Choate et al, Hum Gene Ther 1997;8:1659-65.*
Sharkawy et al, J Biomed Mater Res 1997;5:401-12.*
Game et al, Wien Klin Wochenschr 2001;113:823-38.*
Platt et al, Nat Biotech Mar. 2002;20:231-2.*
Paus et al, J Dermatol Sci 1994;7:202-9.*
Lippin et al, Blood 2005;106:2280-6.*
Granov et al. "Extracorporeal Fixation of Liver Slices Onto the System of 'Artificial Kidney' Apparatus", Pub Med., 116(3): 106-109, 1976.
Li et al. "Skin Toxicity Determined in Vitro by Three-Dimensional, Native-State Histoculture", Proc. Natl. Acad. Sci., 88: 1908-1912, 1991.
Norris "A Generous Contribution by Roche Dermatology Division of Hoffman-La Roche Inc. to the Endowment for the Journal has Supported this Issue", The Journal of Investigative Dermatology, 95(4), 1990.
Burke et al. "Preparation of Clone Libraries in Yeast Artificial-Chromosome Vectors", in Methods in Enzymology, 194:251-270, 1991.
Carey et al. "An Amino-Terminal Fragment of GAL4 Binds DNA as a Dimer", Academic Press Ltd. (1989), J. Mol. Biol., 209:423-4332.

Gale et al. "Growth Factors Acting via Endothelial Cell-Specific Receptor Tyrosine Kinases: VEGF's, Angiopoietins, and Ephrins in Vascular Development", Genes and Development 13, 1055-1066 (1999).

Huxley et al. "The Human HPRT Gene on a Yeast Artifical Chromosomes is Functional when Trasferred to Mouse Cells by Cell Fusion", Genomics, 9:742-750 (1991).

Pearson et al. "Expression of the Human Beta-Amyloid Precursor Protein Gene From a Yeast Artificial Chromosome in Transgenic Mice.", Proc. Natl. Acad. Sci. USA, 1993, 90:10578-82.

Achim "In Vivo Model of HIV Infection of the Human Brain", Advances in Neuroimmunology, 4(3): 261-264, 1994.

Cress et al. "Critical Structural Elements of the VP16 Transcriptional Activation Domain", (1991) Science, 251:87-90.

Davies et al. "Targeted Alterations in Yeast Artificial Chromosomes for Inter-Species Gene Transfer", Nucleic Acids Research, 20 (11) 2693-2698, 1992.

Dickinson et al. "High Frequency Gene Targeting Using Insertional Vectors", Human Molecular Genetics, 2(8):1299-1302, 1993.

Futterer et al. "Translation of a Polycistronic mRNA in the Presence of the Cauliflower Mosaic Virus Transactivator Protein", (1991) EMBO J. 10:3887-3896.

Jakobovits et al. "Germ-Line Transmission and Expression of a Human-Derived Yeast Artifical Chromosome", Nature, 362:255-261 (1993).

Rothstein "Targeting, Disruption, Replacement, and Allele Rescue: Integrative DNA Transformation in Yeast", Methods in Enzymology, 194:281-301 (1991).

Sadowski et al. "GAL4-VP16 is an Unusually Potent Transcriptional Activator", (1988), Nature, 335:563-564.

Schedl et al. "A Yeast Artificial Chromosome covering The Tyrosinase Gene Confers Copy Number-Dependent Expression in Transgenic Mice", Nature, 362:258-261, (1993).

Capecchi "Altering the Genome by Homologous Recombination", Science, 244:1288-1292, 1989.

Iruela-Arispe et al. "Angiogenesis: A Dynamic Balance of Stimulators and Inhibitors", (1997) Thrombosis and Haemostasis 78(1), 672-677.

Epstein et al. "Human Neural Xenografts: Progress in Developing An In-Vivo Model to Study Human Immunodeficiency Virus (HIV) and Human Cytomegalovirus (HCMV) Infection", Advances in Neuroimmunology, 4(3): 257-260, 1994.

Sampson-Johannes et al. "Colonization of Human Lung Grafts in SCID-Hu Mice by Human Colon Carcinoma Cells", Int. J. Cancer, 65: 864-869, 1996.

Mansbridge et al. "Three-Dimensional Fibroblast Culture Implant for the Treatment of Diabetic Foot Ulcers: Metabolic Activity and Therapeutic Range", Tissue Engineering, 4(4): 403-414, 1998.

Freshney "Culture of Animal Cells, A Manual of Basic Technique": 297-307, 1987. Esp. p. 302.

Parrish et al. "Minireview: Precision-Cut Tissue Slices: Applications in Pharmacology and Toxicology", Life Sciences, 57(21): 1887-1901, 1995.

Lamb et al. "Introduction and Expression of the 400 Kilobase Precursor Amyloid Protein Gene in Transgenic Mice", Nature Genetics, 5:22-29, 1993.

Houdebine "Production of Pharmaceutical Proteins From Transgenic Animals", J. Biotechnology, 34: 269-287, 1994.

Wall "Transgenic Livestock: Progress and Prospects for the Future", Thenogenology, 45: 57-68, 1996.

Sigmund "Viewpoint: Are Studies in Genetically Altered Mice Out of Control?", Arterioscler. Thromb. Vasc. Biol., 20: 1425-1429, 2000.

Niemann "Transgenic Farm Animals Get Off the Ground", Transgenic Research, 7: 73-75, 1998.

Crystal "Transfer of Genes to Humans: Early Lessons and Obstacles to Success", Science, 270: 404-410, 1995.

Verma et al. "Gene Therapy—Promises, Problems and Prospects", Nature, 389: 239-242, 1997.

Deonarain "Ligand-Targeted Receptor-Mediated Vectors for Gene Delivery", Exp. Opin. Ther. Patents, 8(1): 53-69, 1998.

Miller et al. "Targeted Vectors for Gene Therapy", FASEB J., 9: 190-199, 1995.

Eck et al. "Gene-Based Therapy", in: Goodman & Gilman's 'The Pharmacological Basis of Therapeutics', 9/e, Chap.5: 77-101, 1997.

Ledley "Pharmaceutical Approach to Somatic Gene Therapy", Pharm. Res., 13(11): 1595-1614, 1996.

Saadi et al. "Immunology of Xenotransplantation", Life Sciences, 62(5): 365-387, 1998.

Inverardi et al. "Cell Transplantation", in: 'Transplantation Biology: Cellulat and Molecular Aspects', Raven Pub., Chap. 56, 1996.

Cameron "Recent Advances in Transgenic Technology", Molecular Biotechnology, 7: 253-265, 1997.

Eto et al. "Purification and Charcterization of Erythroid Differntiation Factor (EDF) Isolated Frim Human Leukemia Cell Line THP-1", Bichomical and Biophysical Research Communications, 142(3): 1095-1103, 1987.

Chesnokova et al. "The Thymic Factor Tactivin Prevents ACTH From Stimulating Steroldogenesis by Mouse Adrenal Cells", Institute of Cytology and Genetics, USSR Academy of Science, 1990.

Descamps et al. "Organoids Direct Systematic Expression of Erythropoietin in Mice", Gene Therapy, 2:411-417, 1995.

Villeval et al. "Retrovirus-Mediated Transfer of the Erythroprotein Gene in Hematopoietoic Cells Improves the Erythrocyte Phenotype in Murine β-Thalassemia", Blood, 84(3): 928-933, 1994.

Palu et al. "In Pursuit of New Developments for Gene Therapy of Human Diseases", J. Biotechnology, 68: 1-13, 1999.

Romano et al. "Gene Transfer Technology in Therapy: Current Applications and Future Goals", Stem Cell, 17: 191-202, 1999.

Kappel et al. "Regulating Gene Expression in Transgenic Animals", Current Opinion in Biology, 3: 548-553, 1992.

Mullins et al. "Transgenesis in the Rat and Larger Mammals", J. Clin. Invest., 97(7): 1557-1560, 1996.

Mullins et al. "Transgenesis in Nonmurine Species", Hypertension, 22(4): 630-633, 1993.

Levine, M., "The Growth of Adult Human Skin In Vitro", *Br. J. Derm*, 86:481, 2, 7, 1972.

Agren et al, Human Fetal Pancreas, Culture and Function In Vitro, *Diabetes*, 29(Supp. 1):64-69, 1980.

Eiseman et al, "Prosthetics in Hepatic Assistance", *Transplantation Proceedings*, vol. III, No. 4, pp. 1519-1524, 1971.

Watson et al, "Sheep Vibrissa Dermal Papillae Induce Hair Follicle Formation in Hetertypic Skin Equivalents", *Br. J. Derm.*, 131:827-835, 1994.

Varani et al, "All-Trans Retinoic Acid and Extracellular $Ca^{2+}$ Differentially Influence Extracellular Matrix Production by Human Skin in Organ Culture", *Am. J. Pathology*, 142(6):1813-1822, 1993.

Reynolds et al, "Cultured Dermal Papilla Cells Induce Follicle Formation and Hair Growth by Transdifferentiation of an Adult Epidermis", *Development*, 115:587-593, 1992.

Coulomb et al, "Interactions Dermo-Epidermiques et Pharacologie Cutanee", *Path Biol*, 40(2):139-146, 1992.

Philpott et al, "Rat Hair Folliclr Growth In Vivo", *Br. J. Derm*, 127:600-607, 1992.

Lingna, L., "Skin Toxicity Determined in vitro by Three-Dimensional, Native-State Histoculture", *Proc. Natl. Acad. Sci.*, USA, 88:1908-1912, 1991.

Sugihara et al, "Reconstruction of the Skin in Three-Dimensional Collagen Gel Matrix Culture", *In Vitro Cell. Dev.Biol.*, 27A:142-146, 1991.

Parenteau et al, "Epidermis Generated In Vitro: Practical Considerations and Applications", *J. Cellular Biochem.*, 45:245-251, 1991.

Kondo et al, "Long-Term Organ Culture of Rabbit Skin: Effect of EGF on Epidermal Structure In Vitro", *J. Invest Dermatol*, 95:397-402, 1990.

"Alternative Methods in Toxicology Series, vol. 7", Alan M. Goldberg (Editor), 1989, Preface.

"Alternative Methods in Toxicology Series, vol. 6", Alan M. Goldberg (Editor), 1988, Chap A3, "Testskin: A Hybrid Organism Covered by a Living Human Skin Equivalent Designed for Toxicity and Other Testing", by Bell et al.

Pinkus, H., "Examination of the Epidemis by the Strip Method of Removing Horny Layers", *J. Invest. Derm.*, 16:383-386, 1951.

Rheinwald et al, "Serial Cultivation of Strains of Human Epidermal Keratinocytes: Thew Formation of Keratinizing Colonies from Single Cells", *Cell*, 6(3):331-43, 1975.

Boisseau et al, "Production of Epidermal Sheets in a Serum Free Culture System: A Further Appraisal of the Role of Extracellular Calcium", *J. Derm. Sci.*, 3:111-120, 1992.

Boyce et al, "Calcium-Regulated Differentiation of Normal Human Epidermal Keratinocytes in Chemically Defined Clonal Culture and Serum-Free Serial Culture", *J. Invest. Derm.*, 81(1):33S-40S, 1983.

Soyer et al, "Extracorporeal Assist Of Anhepatic Animals With Liver Slice Perfusion", *Am J Surg.* 126(1):20-4, 1973.

Kao et al, "Skin Penetration and Metabolism of Topically Applied Chemicals in Six Mammalian Species, Including Man: An in Vitro Study with Benzo[a]pyrene and Testosterone", *Toxicology and Applied Pharmacology*, 81:502-516, 1985.

Gurdon, J.B., "The Generation of Diversity and Pattern in Animal Development", *Cell*, 68:185-199, 1992.

Choi et al, "TGF-β and Retinoic Acid: Regulators of Growth and Modifiers of Differentiation in Human Epidermal Cells", *Cell Regulation*, 1:791-809, 1990.

Gerlach, J.C., "Hepatocyte Culture And Bioreactor Design For Liver Support Systems", Chap. 19 of "Acute Liver Failure", William M. Lee, Ed., Cambridge University Press, 1997.

Communication Pursuant to Article 96(2) EPC Dated Feb. 22, 2006 from the European Patent Office Re.: Application No. 03016266.3.

Communication Pursuant to Article 94(3) EPC Dated Mar. 4, 2008 from European Patent Office Re.: Application No. 01204125.7.

Communication Pursuant to Article 96(2) EPC Dated Jan. 23, 2001 from European Patent Office Re.: Application No. 95905458.6.

Communication Pursuant to Article 96(2) EPC Dated Dec. 13, 2006 from the European Patent Office Re.: Application No. 98909974.2.

Communication Pursuant to Article 96(2) EPC Dated Nov. 22, 2005 from the European Patent Office Re.: Application No. 01204125.7.

Communication Pursuant to Article 96(2) EPC Dated Oct. 28, 2004 from the European Patent Office Re.: Application No. 00939024.6.

Communication Pursuant to Article 96(2) EPC Dated Dec. 6, 1999 from the European Patent Office Re.: Application No. 95905458.6.

European Search Report Dated Nov. 7, 2003 from the European Patent Office Re:. Application No. 03016266.3.

European Search Report Dated Dec. 19, 2006 from the European Patent Office Re:. Application No. 03019593.7.

Examiner's Report Dated Jul. 6, 2007 from the Australian Government, IP Australia Re.: Application No. 2003271042.

Examiner's Report Dated Aug. 31, 2007 From the Australian Government, IP Australia Re.: Application No. 200327142.

International Preliminary Examination Report Dated Dec. 11, 2000 from the International Preliminary Examination Authority Re.: Application No. PCT/US98/00594.

International Preliminary Examination Report Dated Feb. 19, 1997 from the International Preliminary Examining Authority Re.: Application No. PCT/US94/14822.

International Preliminary Examination Report Dated Jul. 23, 2004 from the International Preliminary Examining Authority Re.: Application No. PCT/IL00/00365.

International Search Report Dated Jan. 4, 2005 from the International Searching Authority Re.: Application No. PCT/IL04/00202.

International Search Report Dated Nov. 8, 2000 from the International Searching Authority Re.: Application No. PCT/IL00/00365.

International Search Report Dated Dec. 10, 2002 from the International Searching Authority by the Patent Cooperation Treaty Re.: Application No. PCTIL01/00976.

International Search Report Dated Mar. 13, 2003 From the International Searching Authority Re.: Application No. PCT/IL02/00879.

International Search Report Dated Jan. 16, 2001 from the International Searching Authority by the Patent Cooperation Treaty Re.: Application No. PCT/IL00/00424.

International Search Report Dated Mar. 18, 2005 From the International Searching Authority Re.: Application No. PCT/US04/13194.

International Search Report Dated Jul. 20, 2004 from the International Searching Authority Re.: Application No. PCT/IL03/00578.

International Search Report Dated Aug. 7, 1995 from the International Searching Authority by the Patent Cooperation Treaty Re.: Application No. PCTUS94/14822.

Office Action Dated Nov. 2, 2008 From the Israeli Patent Office Re.: Application No. 161472 and Its Translation Into English.

Office Action Dated Jun. 14, 2005 From the Japanese Patent Office Re.: Application No. 2003-538352.

Official Action Dated Jun. 1, 2006 from the United States Patent Trademark Office Re.: U.S. Appl. No. 10/376,506.

Official Action Dated Mar. 1, 2004 from the Canadian Intellectual Property Office Re.: Application No. 2,205,207.

Official Action Dated Jan. 3, 2006 from the United States Patent and Trademark Office Re.: U.S. Appl. No. 10/009,520.

Official Action Dated Dec. 4, 2006 from the United States Patent and Trademark Office Re.: U.S. Appl. No. 10/320,717.

Official Action Dated Apr. 5, 2006 from the United States Patent and Trademark Office Re.: U.S. Appl. No. 10/320,717.

Official Action Dated Apr. 5, 2006 from the United States Patent and Trademark Office Re.: U.S. Appl. No. 10/320,703.

Official Action Dated Jan. 5, 1998 from the United States Patent and Trademark Office Re.: U.S. Appl. No. 08/341,409.

Official Action Dated May 5, 2008 From the Israeli Patent Office Re.: Application No. 161472.

Official Action Dated Feb. 7, 2008 from the United States Patent and Trademark Office Re.: U.S. Appl. No. 10/320,717.

Official Action Dated May 9, 2008 From the Canadian Intellectual Property Office Re.: Application No. 2,464,460.

Official Action Dated Apr. 10, 2007 From the Japanese Patent Office Re.: Application No. 11-536048.

Official Action Dated Aug. 10, 2007 from the United States Patent and Trademark Office Re.: U.S. Appl. No. 10/519,838.

Official Action Dated Mar. 11, 2008 from the United States Patent and Trademark Office Re.: U.S. Appl. No. 10/320,703.

Official Action Dated Nov. 12, 2004 from the United States Patent and Trademark Office Re.: U.S. Appl. No. 10/201,685.

Official Action Dated Sep. 14, 2006 from the United States Patent and Trademark Office Re.: U.S. Appl. No. 10/009,520.

Official Action Dated Aug. 15, 2003 From the State Intellectual Property Office of the People's Republic of China Re.: Application No. 98808474.0, and its translation into English.

Official Action Dated Nov. 16, 2006 from the United States Patent and Trademark Office Re.: U.S. Appl. No. 10/519,838.

Official Action Dated Aug. 17, 2007 from the United States Patent and Trademark Office Re.: U.S. Appl. No. 10/320,717.

Official Action Dated Jun. 18, 2008 from the United States Patent and Trademark Office Re.: U.S. Appl. No. 10/376,506.

Official Action Dated Sep. 19, 2007 from the United States Patent and Trademark Office Re.: U.S. Appl. No. 10/376,506.

Official Action Dated Jul. 23, 1996 from the United States Patent and Trademark Office Re.: U.S. Appl. No. 08/341,409.

Official Action Dated Oct. 25, 2007 From the Korean Patent Office Re.: Application No. 2004-7006068.

Official Action Dated Mar. 26, 2004 from the United States Patent and Trademark Office Re.: U.S. Appl. No. 09/890,172.

Official Action Dated Jul. 28, 2008 From the Canadian Intellectual Property Office Re.: Application No. 2,377,541.

Official Action Dated Apr. 29, 2008 from the United States Patent and Trademark Office Re.: U.S. Appl. No. 10/519,838.

Official Action Dated Jun. 29, 2006 from the United States Patent and Trademark Office Re.: U.S. Appl. No. 10/182,352.

Supplementary European Search Report Dated Mar. 17, 2005 from the European Patent Office Re.: Application No. 98909974.2.

Supplementary Partial European Search Report Dated Feb. 6, 2003 from the European Patent Office Re.: Application No. 00939024.

Translation of Examination Report Dated May 17, 2006 from the Government of India, Patent Office Re:. Appliction No. 834/CHENP/2004.

Translation of the Official Action Dated Jul. 9, 2007 From the Japanese Patent Office Re.: Application No. 2003-538352.

Albano et al. "A Mesoderm-Inducing Factor Produced by WEHI-3 Murine Myelomonocytic Leukemia Cells Is Activin A", Development, 110: 435-443, 1990.

Asashima et al. "Mesodermal Induction in Early Amphibian Embryos by Activin A (Erythroid Differentiation Factor)", Development Genes and Evolution, 198(6): 330-335, 1990. Abstract.

Boukamp et al. "Environmental Modulation of the Expression of Differentiation and Malignancy in Six Human Squamous Cell Carcinoma Cell Lines", Cancer Research, 45: 5582-5592, 1985.

Bullough et al. "The Control of Epidermal Mitotic Activity in the Mouse", Proceedings of the Royal Society, Series B., Biological Sciences, 151(945): 517-536, 1960. Abstract.

Dvir et al. "The Inhibition of EGF-Dependent Proliferation of Keratinocytes by Tyrphostin Tyrosine Kinase Blockers" The Journal of Cell Biology, 133(4): 857-865, 1991.

Jones et al. "Involvement of Bone Morphogenetic Protein-4 (BMP-4) and Vgr-1 in Morphogenesis and Neurogenesis in the Mouse", Development, 111: 531-542, 1991.

Ling et al. "Pituitary FSH Is Released by A Heterodimer of the Beta-Subunits From the Two Froms of Inhibin", Nature, 321: 779-782, 1986. Abstract.

Lyons et al. "Vgr-1, A Mammalian Gene Related to Xenopus Vg-1, Is A Member of the Transforming Growth Factor ? Gene Superfamily", Proc. Natl. Acad. Sci. USA, 86: 4554-4558, 1989.

Mason et al. "Complementary DNA Sequences of Ovarian Follicular Fluid Inhibin Show Precursor Structure and Homology With Transforming Growth Factor-Beta", Nature, 318: 659-663, 1985. Abstract.

Mathews et al. "Expression Cloning of An Activin Receptor, A Predicted Transmembrane Serine Kinase", Cell, 65: 973-982, 1991. Abstract.

Mitrani et al. "Activin Can Induce the Formation of Axial Structures and Is Expressed in the Hypoblast of the Chick", Cell, 63: 495-501, 1990. Abstract.

Mitrani et al. "Induction by Soluble Factors of Organized Axial Structures in Chick Epiblasts", Science, 247: 1092-1094, 1990. Abstract.

Murata et al, "Erythroid Differentiation Factor Is Encoded by the Same mRNA as That of the Inhibin Beta A Chain", Proc. Natl. Acad. Sci. USA, 85: 2434-2438, 1988.

Pelton et al. "Expression of Transforming Growth Factor Beta 2 RNA During Murine Embryogensis", Development, 106(4): 759-767, 1989. Abstract.

Schubert et al. "Activin Is A Nerve Cell Survival Molecule", Nature, 344: 868-870, 1990. Abstract.

Smith et al. "Identification of A Potent Xenopus Mesoderm-Inducing Factor as A Hologue of Activin A", Nature, 345: 729-731, 1990. Abstract.

Strauss et al. "Germ Line Transmission of A Yeast Artificial Chromosome Spanning the Murine Alpha 1(I) Collagen Locus", Science, 259(5103): 1904-1907, 1993. Abstract.

Thompson et al. "Expression of Transforming Growth Factor-Beta1 in Specific Cells and Tissues of Adult and Neonatal Mice", The Journal of Cell Biology, 108: 661-669, 1989.

Thomsen et al. "Activins Are Expressed Early in Xenopus Embryo-Genesis and Can Induce Axial Mesoderm and Anterior Structures", Cell, 63: 485-493, 1990. Abstract.

Vale et al. "Purification and Characterization of An FSH Releasing Protein From Porcine Ovarian Follicular Fluid", Nature, 321: 776-779, 1986. Abstract.

Weiss et al. "A Model of Growth & Growth Control in Mathematical Terms", The Journal of General Physiology, 41(1): 1-47, 1957.

Bergold et al. "Transsynaptic Neuronal Loss Induced in Hippocampal Slice Cultures by A Herpes Simplex Virus Vector Expressing the GluR6 Subunit of the Kainate Receptor", Proc. Natl. Acad. Sci. USA, 90: 6165-6169, 1993.

Bradl et al. "Malignant Melanoma in Transgenic Mice", Proc. Natl. Acad. Sci. USA, 88: 164-168, 1991.

Cassell et al. "Vascularisation of Tissue-Engineered Grafts: The Regulation of Angiogenesis in Reconstructive Surgery and in Disease States", British Journal of Plastic Surgery, 55: 603-610, 2002.

Clark et al. "Islet Cell Culture in Definded Serum-Free Medium", Endocrinology, 126(4): 1895-1903, 1990.

Furth et al. "Gene Transfer by Jet Injection Into Differentiated Tissues of Living Animals and in Organ Culture", Molecular Biotechnology, 4: 121-127, 1995.

German et al. "Regulation of Insulin Gene Expression by Glucose and Calcium in Transfected Primary Islet Cultures", The Journal of biological Chemistry, 265(36): 22063-22066, 1990.

Iizuka et al. "Effects of Retinoids on the Cyclic AMP System of Pig Skin Epidermis", The Journal of Investigative Dermatology, 85(4): 324-327, 1985.

Khurana et al. "Gene Therapy for Cardiovascular Disease: A Case for Cautious Optimism", Hypertension, 38(5): 1210-1216, 2001.

Laham et al. "Gene Transfer for Angiogenesis in Coronary Artery Disease", Annual Reviews in Medicine, 52: 485-502, 2001.

Laub et al. "Expression of the Human Insulin Gene and cDNA in A Heterologous Mammalian System", The Journal of Biological Chemistry, 258(10): 6043-6050, 1983.

Massoud et al. "Laboratory Evaluation of A Microangioscope for Potential Percutaneous Cerebrovascular Applications", AJNR, American Journal of Neuroradiology, 22: 363-365, 2001.

Metrakos et al. "Intercellular Communication and Maintenance of Islet Cell Mass—Implications for Islet Transplantation", Surgery, 114: 423-428, 1993.

Mintz et al. "Transgenic Mouse Model of Malignant Skin Melanoma", Proc. Natl. Acad, Sci. USA, 90: 8817-8821, 1993.

Mole et al. "Structure and Function of SV40 Large-T Antigen", Philosophical Transactions of the Royal Society of London, Series B, Biological Sciences, 317(1187): 455-469, 1987.

Montaña et al. "Beta Cell Mass and Growth After Syngeneic Islet Cell Transplantation in Normal and Streptozocin Diabetic C57BL/6 Mice", Journal of Clinical Investigation, 91: 780-787, 1993.

Rubanyi "The Future of Human Gene Therapy", Molecular Aspects of Medicine, 22(3): 113-142, 2001.

Tran et al. "Autologous Cell Transplantation and Cardiac Tissue Engineering: Potential Applications in Heart Failure", Biorheology, 40(1-3): 411-415, 2003. Abstract.

Yu et al. "Importance of FSH-Releasing Protein and Inhibin in Erythrodifferentiation", Nature, 330: 765-767, 1987. Abstract.

Wilkemeyer et al. "Adenovirus-Mediated Gene Transfer Into Dissociated and Explant Cultures of Rat Hippocampal Neurons", Journal of Neuroscience Research, 43(2): 161-174, 1996.

Liu et al. "Hypoxia Regulates Vascular Endothelial Growth Factor Gene Expression in Endothelial Cells. Identification of A 5' Enhancer", Circulation Research, 77(3): 638-643, Sep. 1995. Abstract.

Official Action Dated Jan. 9, 2009 From the US Patent and Trademark Office Re.: U.S. Appl. No. 10/376,506.

Official Action Dated Jan. 12, 2009 From the US Patent and Trademark Office Re.: U.S. Appl. No. 10/320,703.

Faustman et al. "Prevention of Xenograft Rejection by Masking Donor HLA Class I Antigens", Science, 252: 1700-1702, Jun. 21, 1991.

Fenjves et al. "Systemic Distribution of Apolipoprotein E Secreted by Grafts of Epidermal Keratinocytes: Implications for Epidermal Function and Gene Therapy", Proc. Natl. Acad. Sci. USA, 86: 8803-8807, Nov. 1989.

Flaxman et al. "In Vitro Analysis of the Control of Keratinocyte Proliferation in Human Epidermis by Physiologic and Pharmacologic Agents", The Journal of Investigative Dermatology, 65(1): 52-59, 1975.

Hu et al. "Comparative Studies of the Angiogenic Activity of Vasoactive Intestinal Peptide, Endothelins-1 and -3 and Angiotensin II in A Rat Sponge Model", British Journal of Pharmacology, 117: 545-551, 1996.

Lanza et al. "Islet Transplantation With Immunoisolation", Perspectives in Diabetes, Diabetes, 41: 1503-1510, 1992.

Naffakh et al. "Sustained Delivery of Erythropoietin in Mice by Genetically Modified Skin Fibroblasts", Proc. Natl. Acad. Sci. USA, 92: 3194-3198, Apr. 1995.

Petersen et al. "Development of A Nude Mouse Model to Study Human Sebaceous Gland Physiology and Pathophysiology", Journal of Clinical Investigation, 74: 1358-1365, Oct. 1984.

Vasilopoulos et al. "Erythropoietin Response to Post-Liver Transplantation Anemia", Liver Transplantation, 6(3): 349-355, May 2000.

Wang et al. "An Encapsulation System for the Immunoisolation of Pancreatic Islets", Nature Biotechnology, 15: 358-362, Apr. 1997.

Office Action Dated May 19, 2009 From the Israeli Patent Office Re.: Application No. 161472 and Its Translation Into English.

Ravindranath et al. "Epidermal Growth Factor Modulates the Expression of Vascular Endothelial Growth Factor in the Human Prostate", Journal of Andrology, 22(3): 432-443, May/Jun. 2001.

Burn Survivors Throughout the World "Split-Thickness & Full Thickness Grafts", Retrieved From the Internet, 2004.

ICBS "Parts of the Skin", Beauty Skin Care, ICBS Inc., Holistic-Online.com, Retrieved From the Internet, 1998.

* cited by examiner

FIGURE 4-A
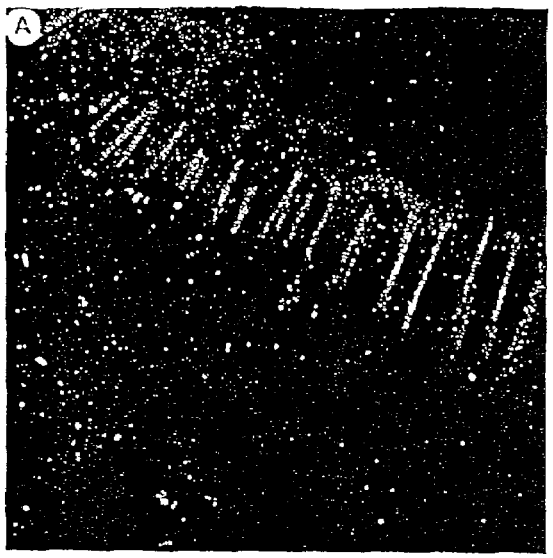
FIGURE 4-B
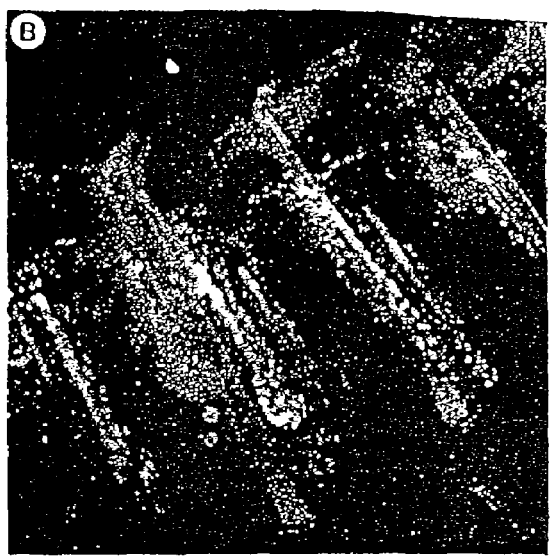
FIGURE 4-C
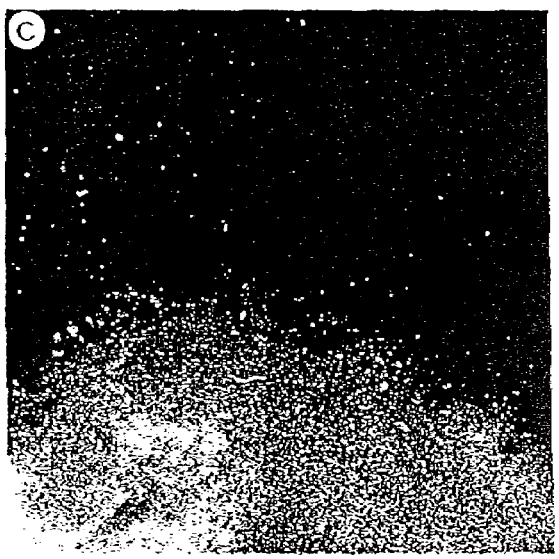
FIGURE 4-D
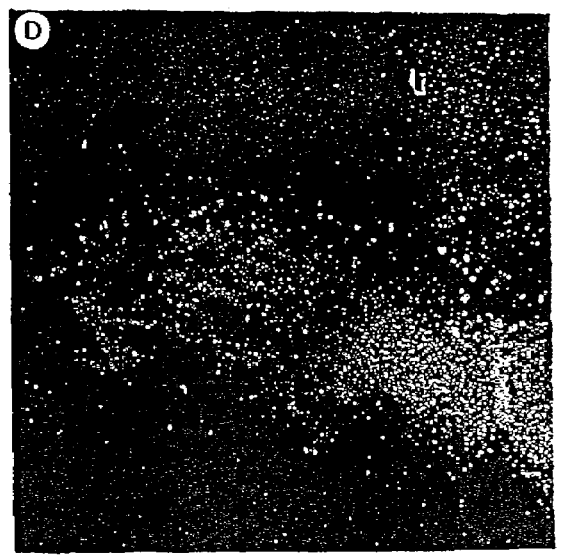

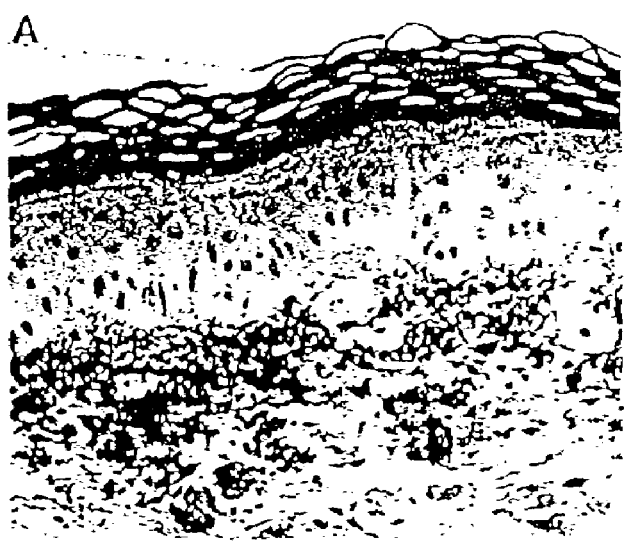
FIGURE 5-A
FIGURE 5-B
FIGURE 5-C

Preliminary experiments indicate that cells proliferate in pancreas-derived cultures
FIGURE 7-A
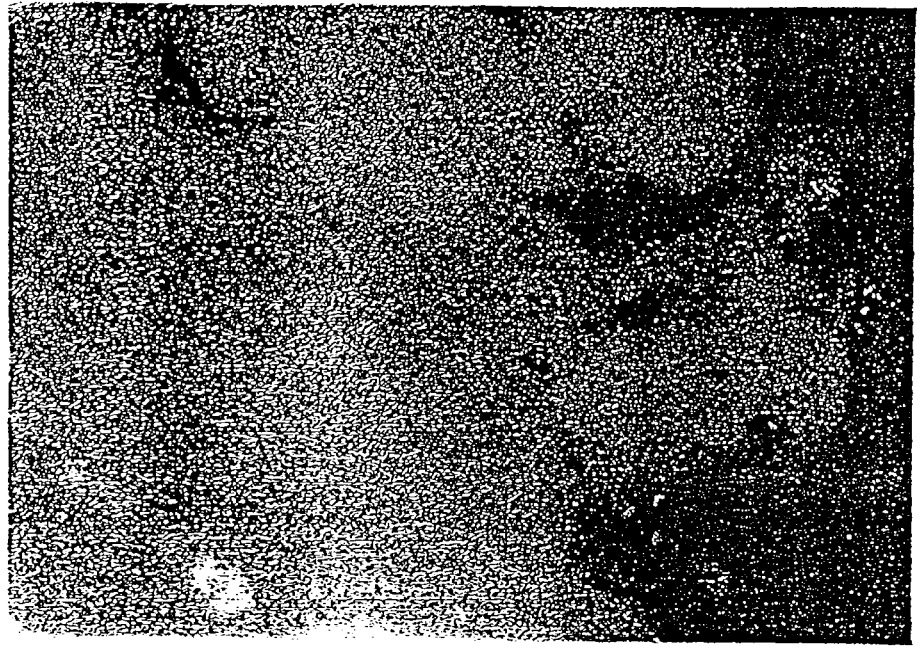
FIGURE 7-B
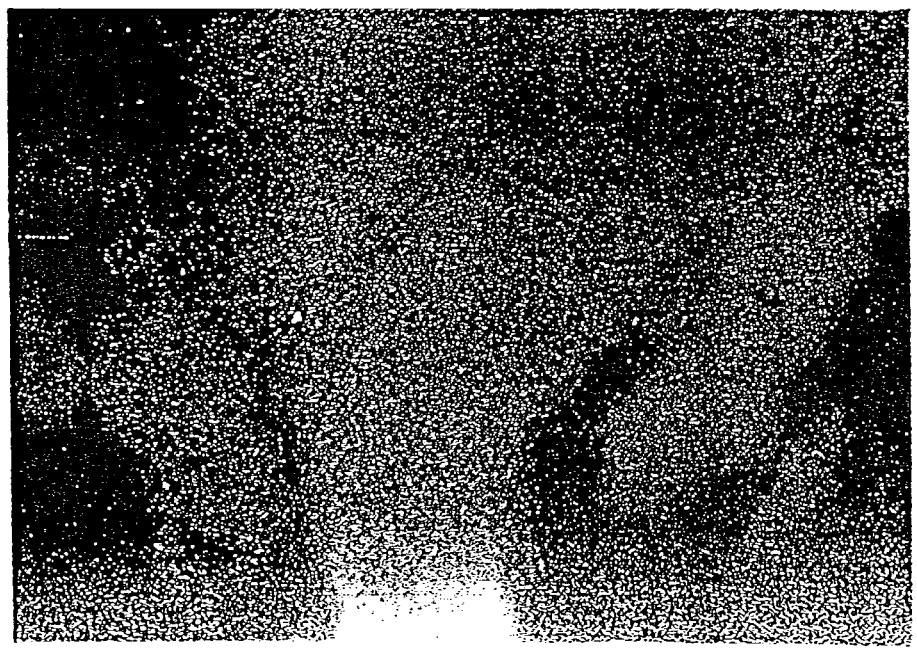

Hair follicle cells proliferate actively in the new culture.
FIGURE 10-A
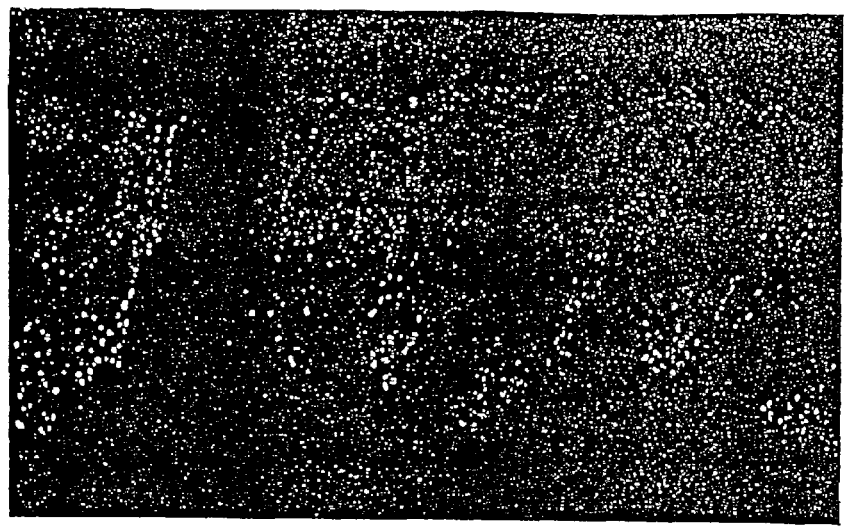
FIGURE 10-B
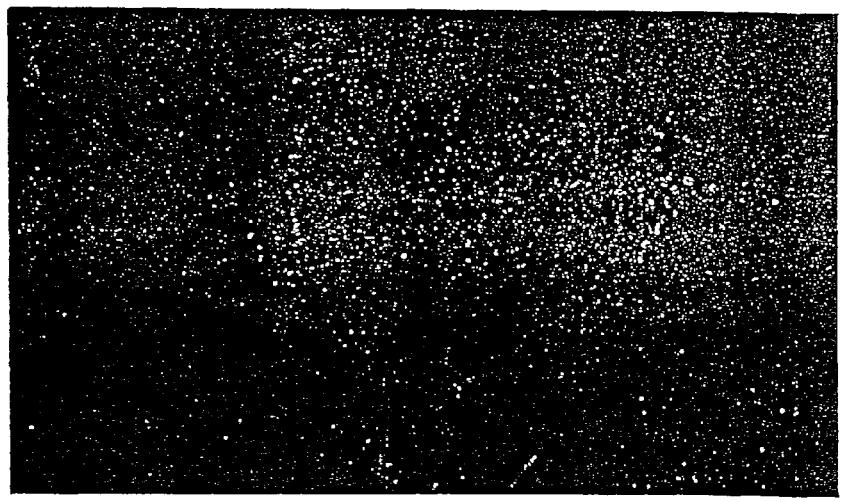
FIGURE 10-C
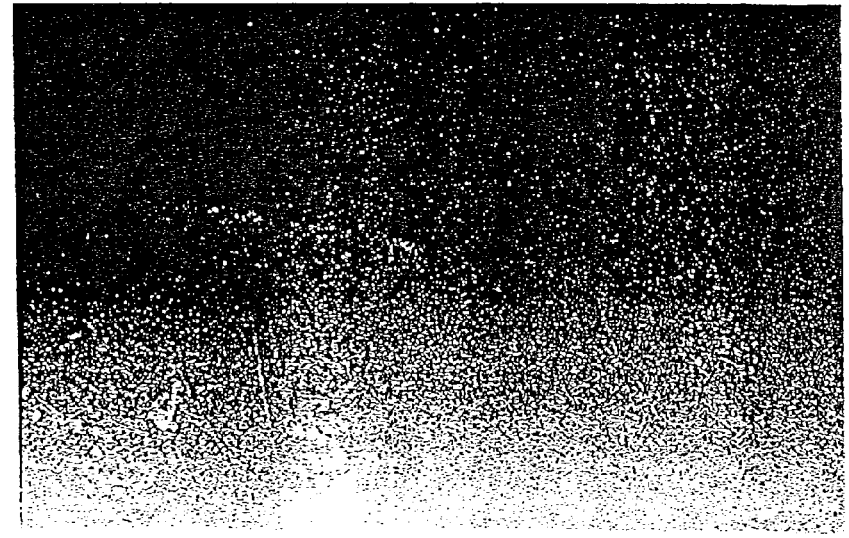

IN VITRO MICRO-ORGANS, AND USES RELATED THERETO

This is a continuation of U.S. patent application Ser. No. 09/589,736, filed Jun. 9, 2000, now abandoned; which is a continuation-in-part of U.S. patent application Ser. No. 09/425,233, filed Oct. 25, 1999, now U.S. Pat. No. 6,472,200; which is a continuation-in-part of U.S. patent application Ser. No. 09/341,630, filed Jul. 15, 1999, now U.S. Pat. No. 6,372,482; which is a U.S. national phase of PCT/US98/00594, filed Jan. 9, 1998. The specification of each of these applications are hereby incorporated by reference.

BACKGROUND OF THE INVENTION

Eukaryotic cell culture was first achieved in the early 1950s. Since that time, a wide range of transformed and primary cells have been cultivated using a wide variety of media and defined supplements, such as growth factors and hormones, as well as undefined supplements, such as sera and other bodily extracts. For example, fibroblasts obtained from the skin of an animal can be routinely cultivated through many cell generations as karyotypically diploid cells or indefinitely as established cell lines. Epithelial cells, however, have morphological and proliferative properties that differ from fibroblasts and are more difficult to cultivate. Moreover, when epithelial cells and fibroblasts are grown in the same culture, the epithelial cells are commonly overgrown by the fibroblasts.

While the growth of cells in two dimensions is a convenient method for preparing, observing and studying cells in culture, allowing a high rate of cell proliferation, it lacks the cell-cell and cell-matrix interactions characteristic of whole tissue in vivo.

In order to study such functional and morphological interactions, a few investigators have explored the use of three-dimensional substrates such as collagen gel (Douglas et al., (1980) In Vitro 16:306-312; Yang et al., (1979) Proc. Natl. Acad. Sci. 76:3401; Yang et al. (1980) Proc. Natl. Acad. Sci. 77:2088-2092; Yang et al., (1981) Cancer Res. 41:1021-1027); cellulose sponge, alone (Leighton et al., (1951) J. Natl Cancer Inst. 12:545-561) or collagen coated (Leighton et al., (1968) Cancer Res. 28:286-296); a gelatin sponge, Gelfoam (Sorour et al., (1975) J. Neurosurg. 43:742-749).

For growing epithelial cells in a clonally competent manner, a variety of culture conditions have been employed. For example, epithelial cells, and in particular, skin epithelial cells (keratinocytes), have been cultivated on feeder layers of lethally irradiated fibroblasts (Rheinhardt et al. (1975) Cell 6:331-343) and on semi-synthetic collagen matrices (U.S. Pat. No. 5,282,859; European Patent Application No. 0361957). In some cases, the media used to grow such cells is manipulated by adding biological extracts, including pituitary extracts and sera, and growth supplements, such as epidermal growth factor and insulin (Boisseau et al. (1992) J. Dermatol. Sci 3(2):111-120; U.S. Pat. No. 5,292,655).

Numerous attempts at growing skin in vitro have been undertaken. These attempts typically include the step of separating the keratinocytes in the epidermis from fibroblasts and fat cells in the dermis. After separation, the keratinocytes are generally grown in a manner that permits the formation of a stratified epidermis. The epidermis prepared in this manner, however, lacks hair follicles and sweat glands. Moreover, in such cultures, the natural relationship between the epidermis and the dermis is not preserved. Cultivation methods including growing keratinocytes on non-viable fibroblasts (Rheinwald et al. (1975) Cell 6:331-343 or placing keratinocytes on a dermal substrate of collagen and fibroblasts that is synthetic or has been derived from an alternative source from that of the epidermis (Sugihara et al. (1991) Cell. Dev. Biol. 27:142-146; Parenteau et al. (1991) J. Cell Biochem. 45(3):245-251) have also been undertaken. In some cases, however, separation of keratinocytes is not performed and the whole organ is placed in culture. Attempts to cultivate organs in vitro have been limited to incubating organs in a serum-containing medium (Li et al. (1991) Proc. Natl. Acad. Sci. 88(5):108-112).

Most existing in vitro models of the epidermis lack hair follicles, sweat glands and sebaceous glands (for a view of epidermal cell culture, see Coulomb et al. (1992) Pathol. Biol. Paris 40(2):139-146). Exceptions include the gel-supported skin model of Li et al. ((1992) Proc. Natl. Acad. Sci 89:8764-8768) in which skin explants with dimensions of 2×5 mm$^2$ and 2.0 mm thick remained viable for several days in the presence of serum-containing media.

In addition to the drawbacks of cell damage, bio-reactors and other methods of culturing mammalian cells are also very limited in their ability to provide conditions which allow cells to assemble into tissues which simulate the spatial three-dimensional form of actual tissues in the intact organism. Conventional tissue culture processes limit, for similar reasons, the capacity for cultured tissues to express a highly functionally specialized or differentiated state considered crucial for mammalian cell differentiation and secretion of specialized biologically active molecules of research and pharmaceutical interest. Unlike microorganisms, the cells of higher organisms such as mammals form themselves into high order multicellular tissues. Although the exact mechanisms of this self-assembly are not known, in the cases that have been studied thus far, development of cells into tissues has been found to be dependent on orientation of the cells with respect to each other (the same or different type of cell) or other anchorage substrate and/or the presence or absence of certain substances (factors) such as hormones, autocrines, or paracrines. In summary no conventional culture process is capable of simultaneously achieving sufficiently low shear stress, sufficient 3-dimensional spatial freedom, and sufficiently long periods for critical cell interactions (with each other or substrates) to allow excellent modeling of in vivo tissue structure.

There is a need, therefore, for in vitro methods of generating and maintaining portions of organs in cultures in which the cells of the culture preserve their natural intercellular relationships for extended periods of time. The availability of tissue and organ models in which cell differentiation, cell proliferation, and cell function mimics that found in the whole organ in vivo would have utility in understanding the mechanisms by which organs are maintained in a healthy state and consequently how abnormal events may be reversed.

SUMMARY OF THE INVENTION

The present invention provides an in-vitro micro-organ culture which addresses the above-cited needs. Salient features of the subject micro-organ cultures include the ability to be maintained in culture for relatively long periods of time, e.g., at least about twenty four hours, preferably for at least seven days or longer, as well as the preservation of an organ microarchitecture which facilitates, for example, cell-cell and cell-matrix interactions analogous to those occurring in the source organ.

Typically, at least one cell of the population of cells of the micro-organ culture has the ability to proliferate. The population of cells in the micro-organ culture can, overall, be in a state of equilibrium, i.e., the ratio of cell proliferation to cell loss in the population of cells is approximately one, or the cells in the micro-organ culture can be proliferating at a greater rate than they are lost, resulting in a ratio of cell proliferation to cell loss in the population of cells which is greater than one, e.g., as in a population of cells obtained from neoplastic tissue, or, c.g., a progenitor cell population induced to proliferate in an explant.

Preferred organs from which the cells of the micro-organ culture can be isolated include lymphoid organs, e.g., thymus and spleen; digestive tract organs, e.g., gut, liver, pancreas, gallbladder and bile duct; lung; reproductive organs, e.g., prostate and uterus; breast, e.g., mammary gland; skin; urinary tract organs, e.g., bladder and kidney; cornea; and blood-associated organs such as bone marrow. The isolated population of cells of the micro-organ culture can, in certain embodiments, be encapsulated within polymeric devices, e.g., for delivery of the cells or cell products, e.g., gene products, to a subject. The present invention also pertains to conditioned medium isolated from the micro-organ cultures of the present invention.

In one embodiment of the present invention, the micro-organ culture includes a population of cells which is a section of an organ. Preferably, the micro-organ explant includes epithelial and connective tissue cells. In one embodiment of the invention, the organ explant is obtained from a pancreas, e.g., the microarchitecture of the population of cells is substantially the same as the microarchitecture of the original pancreas from which the explant was derived, and includes pancreatic epithelial cells, e.g., islet cells, and pancreatic connective tissue cells.

In another embodiment of the invention, the micro-organ explant is obtained from skin, e.g., microarchitecture of the population cells is substantially the same as the microarchitecture of skin in vivo, and includes skin epithelial, e.g., epidermal cells, and skin connective tissue cells, e.g., dermal cells. The micro-organ culture which is obtained from a skin explant can also include a basal lamina supporting the epidermal cells, an extracellular matrix which includes the dermal cells, and at least one invagination, e.g., at least one hair follicle or gland.

In another embodiment of the present invention, the micro-organ culture includes an isolated population of cells infected with a virus, such as a hepatitis virus, e.g., hepatitis B or hepatitis C, or a human papilloma virus (HPV), e.g., HPV-6, HPV-8, or HPV-33. When infected with a virus, the micro-organ culture can be used in a method for identifying an inhibitor of viral infectivity. This method includes isolating a micro-organ explant according to the method of the present invention, which explant is derived from a virally-infected organ, or is subsequently infected in vitro with a virus to produce a population of virus-infected cells in the explant. The explant can then be contacted with a candidate agent, e.g., agent which is being tested for anti-viral activity, and the level of infectivity (e.g., viral loading, new infectivity, etc) in the presence of the candidate agent is measured and compared to the level of infectivity by the virus in the absence of the candidate agent. A decrease in the level of infectivity of the virus in the presence of the candidate agent is indicative of an inhibitor of viral infectivity.

The present invention also pertains to a method for producing a micro-organ culture. This method includes isolating, from a mammalian donor subject, a micro-organ explant having dimensions which provide the isolated population of cells as maintainable in a minimal medium for at least about twenty-four hours. The micro-organ explant is then placed in culture. Typically, the explant includes an isolated population of cells having a microarchitecture of the organ from which the explant is isolated. In one embodiment of the present invention, at least one cell of the explant has the ability to proliferate. The cells of the subject micro-organ culture can be in a state of equilibrium, i.e., the ratio of cell proliferation to cell loss in the population of cells is one, or the cells in the micro-organ culture can be proliferating at a greater rate than they are lost resulting in a ratio of cell proliferation to cell loss in the population of cell loss in the population of cells which is greater than one, e.g., the micro-organ explant includes a population of cells obtained from neoplastic tissue.

Preferred organs from which the cells of the micro-organ culture can be isolated include lymphoid organs, e.g., thymus and spleen; digestive tract organs, e.g., gut, liver, pancreas, gallbladder and bile duct; lung; reproductive organs, e.g., prostate and uterus; breast; skin; urinary tract organs, e.g., bladder; kidney; cornea; and blood-associated organs such as bone-marrow. In each of these examples, the microarchitecture of the organ is maintained by the cultured explant. The micro-organ culture can be a tissue section, e.g., a pancreatic tissue section which includes β-islet cells, e.g., a skin tissue section which includes epidermal and dermal cells and other skin-specific architectural features, e.g., hair follicles.

Cells in the micro-organ explants can also be modified to express a recombinant protein, which protein may or may not be normally expressed by the organ from which the explant is derived. For example, gene products normally produced by the pancreas, and which can be augmented by the subject transgenic method, e.g., to correct a deficiency, include insulin, amylase, protease, lipase, trypsinogen, chymotrypsinogen, carboxypeptidase, ribonuclease, deoxyribonuclease, triacylglycerol lipase, phospholipase $A_2$, elastase, and amylase; likewise, gene products normally produced by the liver, and which can be complemented by replacement gene therapy, include blood clotting factors, such as blood clotting Factor VIII and Factor IX, UDP glucuronyl transferase, ornithine transcarbamoylase, and cytochrome p450 enzymes; gene products normally produced by thymus include serum thymic factor, thymic humoral factor, thymopoietin and thymosin $\alpha_1$.

The micro-organ culture of the present invention can be used in a method for delivering a gene product to a recipient subject. This method includes providing an isolated population of cells from a donor subject, the population of cells having a microarchitecture of an organ or tissue from which the cells are isolated and a surface area to volume which provides the isolated population of cells as maintainable in a minimal medium for at least about twenty-four hours. A recombinant nucleic acid which encodes and directs expression of a desired gene product can then be introduced into the population of cells to produce a population of transgenic cells in the micro-organ explant, e.g., a transgenic explant. The transgenic explant can be administered to a recipient subject. The donor subject and the recipient subject can be of the same species or of different species.

The micro-organ culture of the present invention can also be used in a method for identifying agents which induce proliferation of cells of a given organ, including progenitor cells. This method includes generating a micro-organ explant culture according to the present invention, which explant includes at least one cell which has the ability to proliferate. After being placed in culture, the explant is contacted with a candidate compound, e.g., a compound to be tested for cell proliferative capacity, and the level of cell proliferation in the presence of the candidate compound is measured. The measured level of cell proliferation in the presence of the candidate compound is then compared to the level of cell proliferation in the absence of the candidate compound. An increase in the level of cell proliferation in the presence of the candidate compound is indicative of a cell proliferative agent. Inhibitors of cell proliferation can be identified using a similar method. Specifically, when the measured level of cell proliferation in the presence of the candidate compound is determined using the above-described method, it can be compared to the level of cell proliferation in the absence of the candidate compound. A decrease in the level of cell proliferation in the presence of the candidate compound is indicative of an inhibitor of cell proliferation.

Another method in which the micro-organ culture of the present invention can be used is in a method for identifying an agent which induces, or inhibits, differentiation of one or more cell types in a given organ, or an agent which maintains a particular differentiated state (prevent dedifferentiation). This method includes generating a micro-organ explant from the organ of interest, the population of cells making up the explant having a microarchitecture of that organ, as described hereonbelow, aleph of at least about 1.5 mm$^{-1}$, and including at least one cell which has the ability to differentiate or is differentiated and has the ability to dedifferentiate. Once in culture, the population of cells is contacted with a candidate compound and the level of cell differentiation in the presence of this compound is measured. The measured level of cell differentiation in the presence of the candidate compound is compared with the level of cell differentiation in the absence of the candidate compound. An increase in the level of cell differentiation in the presence of candidate compound is indicative of cell differentiating agent. Inhibitors of cell differentiation can be identified using a similar method. In particular, when the measured level of cell differentiation in the presence of the candidate compound is determined using the above-described method, it can be compared to the level of cell differentiation in the absence of the candidate compound. A decrease in the level of cell differentiation in the presence of the candidate compound is indicative of an inhibitor of cell differentiation.

Yet another aspect of the present invention provides a method for identifying, and isolating, stem cell or progenitor cell populations from an organ. This method generally provides isolating, in a culture, an explant of a population of cells from an organ. As described herein, the explant is characterized by (i) maintenance, in the culture, of a microarchitecture of the organ from which the explant is derived, (ii) a surface area to volume index (aleph) of at least about 1.55 mm$^{-1}$, and (iii) at least one progenitor or stem cell which has the ability to proliferate. The explant is contacted with an agent which induces proliferation of the progenitor or stem cell, e.g., a growth factor or other mitogen, in order to amplify discrete populations of cells in the explant. Subsequently, the amplified progenitor cells can be isolated from the explant. Such sub-populations of the explant can be identified by virtue of their proliferative response. In other embodiments, the progenitor/stem cells will proliferate spontaneously in the culture even without addition of an exogenous agent. In other embodiment, progenitor or stem cells from the explant that proliferate in response to the agent can be isolated, such as by direct mechanical separation of newly emerging buds from the rest of the explant or by dissolution of all or a portion of the explant and subsequent isolation of the amplified cell population.

Still another method in which the micro-organ culture of the present invention can be used is in a method for promoting wound healing in a recipient subject. This method includes isolating, from a donor subject, a population of cells having an aleph of at least approximately 1.5 mm$^{-1}$ and applying the population of cells to a wound of the recipient subject. The donor subject and the recipient subject can be of the same species or of different species. In one embodiment, the tissue from which the cells are isolated is skin and the wound of the recipient subject is an ulcer, e.g., an ulcer associated with diabetes.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning: A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture of Animal Cells (R. I. Freshney, Alan R. Liss, Inc., N.Y.); Gene Transfer Vectors for Mammalian Cells (J. H. Miller and M. P. Calos eds., 1987, Cold Spring Harbor Laboratory); Methods in Enzymology, Vols. 154 and 155 (Wu et al. eds.), Immunochemical Methods In Cell And Molecular Biology (Mayer and Walker, eds., Academic Press, London, 1987); and Handbook of Experimental Immunology, Volumes I-IV (D. M. Weir and C. C. Blackwell, eds., 1986).

Other features and advantages of the invention will be apparent from the following detailed description, and from the claims.

BRIEF DESCRIPTION OF THE DRAWINGS

FIGS. 4A-4D are micrographs showing immunofluorescence corresponding to replicating cells of mouse skin (mag. 50×) (FIG. 4A), guinea pig skin (mag. 75×) (FIG. 4B) human foreskin (mag. 50×) (FIG. 4C) and human foreskin (mag. 75×) (FIG. 4D).

FIGS. 5A-5C are transverse sections of human epidermal micro-organ explants. (mag×75) showing tissue architecture at zero (FIG. 5A), three (FIG. 5B) and six (FIG. 6D) days in culture.

FIG. 7A-7B are micrographs showing immunofluorescence corresponding to proliferating cells in pancreas-derived micro-organ cultures (mag 75×).

FIGS. 10A-10C are micrographs showing active proliferation of hair follicles in micro-organ cultures as determined by immunofluorescence. Magnification 40× (FIG. 10A), 40× (FIG. 10B), and 75× (FIG. 10C).

DETAILED DESCRIPTION OF THE INVENTION

Figure 1:
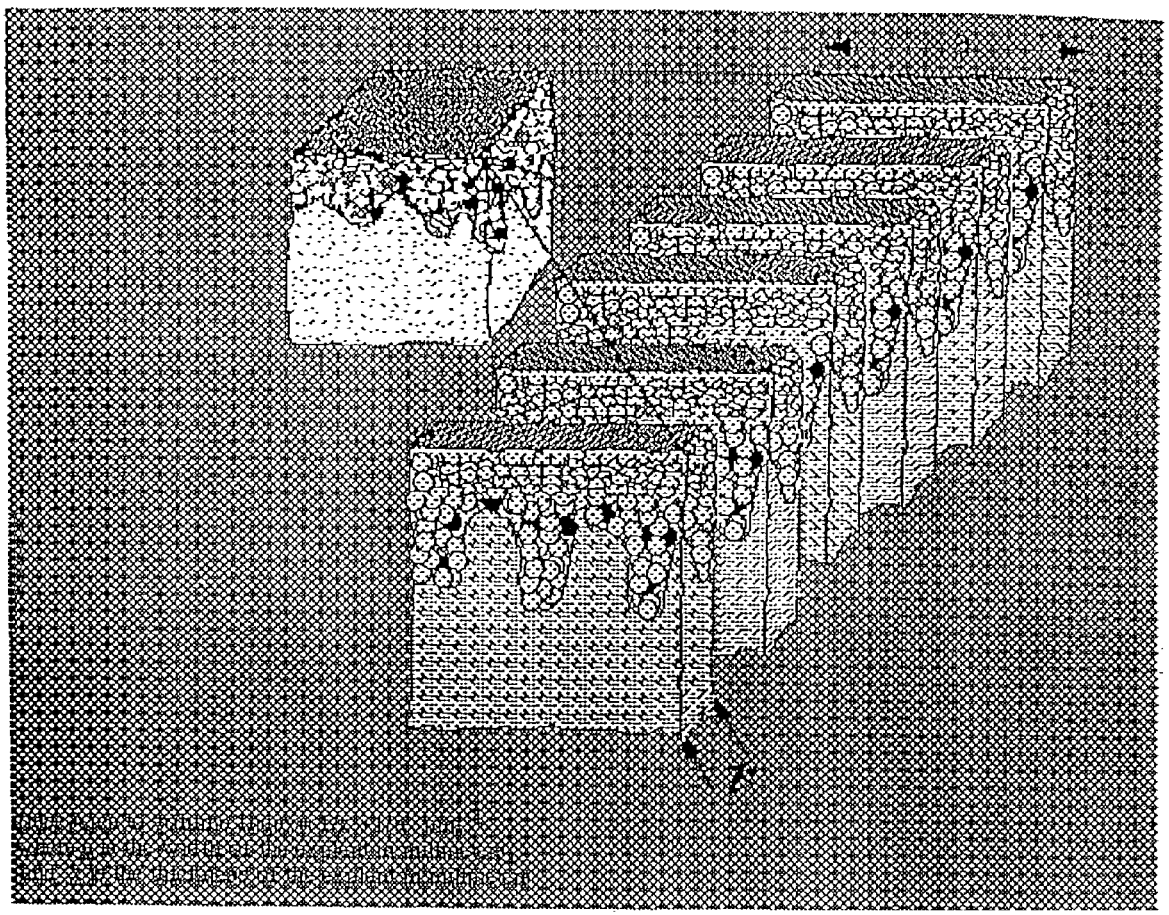
FIG. 1 is a diagrammatic representation of a micro-organ depicting the dimensions that determine Aleph where x=thickness and a=width of tissue.
Figure 2:
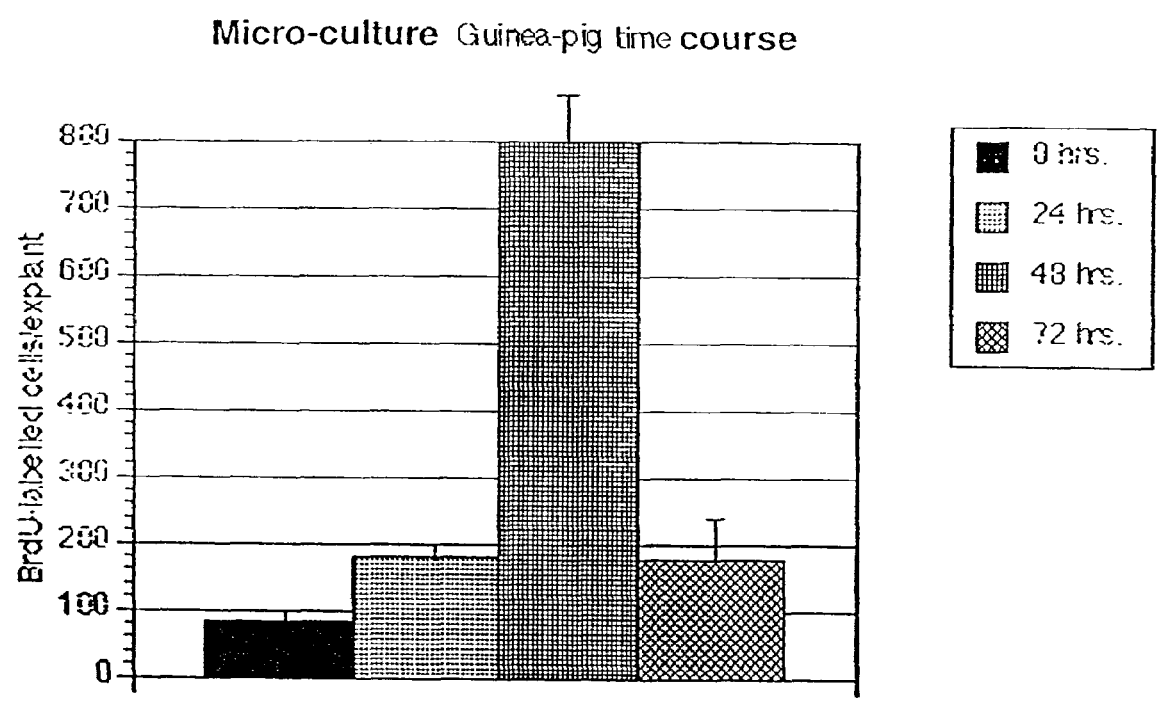
FIG. 2 is a histogram showing cell proliferation in a guinea pig micro-organ culture as determined by BrdU labeling after incubation for different time periods.
Figure 3:
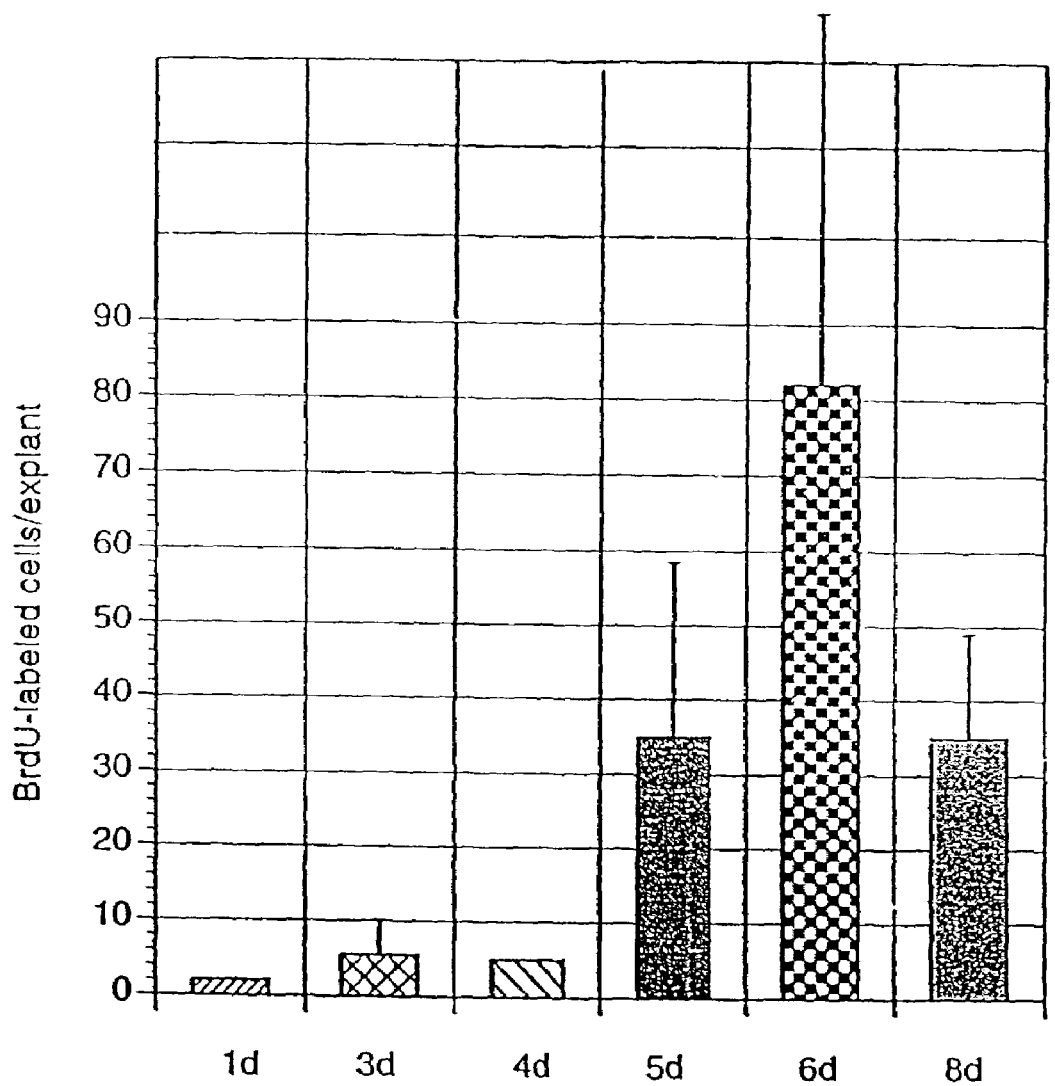
FIG. 3 is a histogram showing cell proliferation in a human back skin micro-organ culture as determined by BrdU labeling after incubation of cultures for 1-8 days.

The present invention is directed to a three-dimensional organ explant culture system. This culture system can be used for the long term proliferation of micro-organ explants in vitro in an environment that closely approximates that found in the whole organ in vivo. The culture system described herein provides for proliferation and appropriate cell maturation to maintain structures analogous to organ counterparts in vivo.

The micro-organ cultures of the present invention provide in vitro culture systems in which tissue or organ sections can be maintained and their function preserved for extended periods of time. These culture systems provide in vitro models in which cell differentiation, cell proliferation, cell function, and methods of altering such cell characteristics and functions can be conveniently and accurately tested. The resulting cultures have a variety of applications ranging from transplantation or implantation ill vivo, to screening cytotoxic compounds and pharmaceutical compounds in vitro, to the production of biologically active molecules in "bioreactors", and to isolating progenitor cells from a tissue.

For example, and not by way of limitation, specific embodiments of the invention include (i) micro-organ bone marrow culture implants used to replace bone marrow destroyed during chemotherapeutic treatment; (ii) micro-organ liver implants used to augment liver function in cirrhosis patients; (iii) genetically altered cells grown in the subject micro-organ culture (such as pancreatic micro-organs which express a recombinant gene encoding insulin); and (iv) dental prostheses joined to a micro-organ culture of oral mucosa.

In yet other illustrative non-limiting embodiments, the subject micro-organ cultures may be used in vitro to screen a wide variety of compounds, such as cytotoxic compounds, growth/regulatory factors, pharmaceutical agents, etc. To this end, the micro-organ cultures are maintained in vitro and exposed to the compound to be tested. The activity of cytotoxic compound can be measured, for example, by its ability to damage or kill cells in the explant.

This may readily be assessed by vital staining techniques. The effect of growth/regulatory factors may be assessed by analyzing the cellular content of the explant, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the three-dimensional system may be assessed. For example, drugs that increase red blood cell formation can be tested on the bone marrow micro-organ cultures. Drugs that affect cholesterol metabolism, e.g., by lowering cholesterol production, could be tested on the liver micro- organs. Micro-organ cultures of abnormal tissue can also be employed, such as to facilitate study of hyperproliferative or neoproliferative disorders. For instance, micro- organ explants of organs invaded by tumor cell growth may be used as model systems to test, for example, the efficacy of anti-tumor agents.

For convenience, certain terms employed in the specification, examples, and appended claims are collected here.

The term "explant" refers to a collection of cells from an organ, taken from the body and grown in an artificial medium. When referring to explants from an organ having both stromal and epithelial components, the term generally refers to explants which contain both components in a single explant from that organ.

The term "tissue" refers to a group or layer of similarly specialized cells which together perform certain special functions.

The term "organ" refers to two or more adjacent layers of tissue, which layers of tissue maintain some form of cell-cell and/or cell-matrix interaction to generate a microarchitecture. In the present invention, micro-organ cultures were prepared from such organs as, for example, mammalian skin, mammalian pancreas, liver, kidney, duodenum, esophagus, bladder, cornea, prostrate, bone marrow, thymus and spleen.

The term "stroma" refers to the supporting tissue or matrix of an organ.

The term "micro-organ culture" as used herein refers to an isolated population of cells, e.g., an explant, having a microarchitecture of an organ or tissue from which the cells are isolated. That is, the isolated cells together form a three dimensional structure which simulates/retains the spatial interactions, e.g. cell-cell, cell-matrix and cell-stromal interactions, and the orientation of actual tissues and the intact organism from which the explant was derived. Accordingly, such interactions as between stromal and epithelial layers is preserved in the explanted tissue such that critical cell interactions provide, for example, autocrine and paracrine factors and other extracellular stimuli which maintain the biological function of the explant, and provide long term viability under conditions wherein adequate nutrient and waste transport occurs throughout the sample.

The subject micro-organ cultures have a microarchitecture of an organ or tissue from which the cells or tissue explant are isolated. As used herein, the term "microarchitecture" refers to an isolated population of cells or a tissue explant in which at least about 50%, preferably at least about 60%, more preferably at least about 70%, still more preferably at least about 80 %, and most preferably at least about 90% or more of the cells of the population maintain, in vitro, their physical and/or functional contact with at least one cell or non cellular substance with which they are in physical and/or functional contact in vivo and form a cell culture of at least about one, more preferably at least about five, and most preferably at least about ten layers or more. Preferably, the cells of the explant maintain at least one biological activity of the organ or tissue from which they are isolated.

The term "isolated" as used herein refers to an explant which has been separated from its natural environment in an organism. This term includes gross physical separation from its natural environment, e.g., removal from the donor animals, e.g., a mammal such as a human or a miniature swine. For example, the term "isolated" refers to a population of cells which is an explant, is cultured as part of an explant, or is transplanted in the form of an explant. When used to refer to a population of cells, the term "isolated" includes population of cells which result from proliferation of cells in the microorgan culture of the invention.

The term "ectoderm" refers to the outermost of the three primitive germ layers of the embryo; from it are derived the epidermis and epidermal tissues such as the nails, hair and glands of the skin, the nervous system, external sense organs and mucous membrane of the mouth and anus.

The terms "epithelia" and "epithelium" refer to the cellular covering, of internal and external body surfaces (cutaneous, mucous and serous), including the glands and other structures derived therefrom, e.g., corneal, esophageal, epidermal and hair follicle epithelial cells. Other exemplary epithelial tissues include: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, which is that characteristically found lining hollow organs that are subject to great mechanical change due to contraction and distention, e.g. tissue which represents a transition between stratified squamous and columnar epithelium. The term "epithelialization" refers to healing by the growth of epithelial tissue over a denuded surface.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "epidermis" refers to the outermost and nonvascular layer of the skin, derived from the embryonic ectoderm, varying in thickness from 0.07-1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent. An "epidermoid" is a cell or tissue resembling the epidermis, but may also be used to refer to any tumor occurring in a noncutaneous site and formed by inclusion of epidermal elements.

The "corium" or "dermis" refers to the layer of the skin beneath deep to the epidermis, consisting of a dense bed of vascular connective tissue, and containing the nerves and terminal organs of sensation. The hair roots, and sebaceous and sweat glands are structures of the epidermis which are deeply embedded in the dermis.

The term "gland" refers to an aggregation of cells specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface. The ordinary or eccrinesweat glands are distributed over most of the body surface, and promote cooling by evaporation of the secretion; the apocrine sweat glands empty into the upper portion of a hair follicle instead of directly onto the skin, and are found only in certain body areas, as around the anus and in the axilla.

The term "hair" (or "pilus") refers to a threadlike structure, especially the specialized epidermal structure composed of keratin and developing from a papilla sunk in the corium, produced only by mammals and characteristic of that group of animals. The term also refers to the aggregate of such hairs. A "hair follicle" refers to one of the tubular-invaginations of the epidermis enclosing the hairs, and from which the hairs grow; and "hair follicle epithelial cells" refers to epithelial cells which are surrounded by the dermis in the hair follicle, e.g., stem cells, outer root sheath cells, matrix cells, and inner root sheath cells. Such cells may be normal non-malignant cells, or transformed/immortalized cells.

The term "alopecia" refers generally to baldness, e.g., the absence of hair from skin areas where it is normally present. Various forms of alopecia are noted in the art. For instance, alopecia areata refers to hair loss, usually reversible, in sharply defined areas, usually involving the beard or scalp; alopecia mediacamentosa refers to hair loss due to ingestion of a drug; and male pattern alopecia, or male pattern baldness, refers to loss of scalp hair genetically determined and androgen-dependent, generally beginning with frontal recession and progressing symmetrically to leave ultimately only a sparse peripheral rim of hair.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidernolytic hyperkeratosis and seborrheic dermatitis. For example, epidernodysplasia is a form of faulty development of the epidermis, such as "epidermodysplasia verruciformis", which is a condition due to a virus identical with or closely related to the virus of common warts. Another example is "epidermnolysis", which refers to a loosened state of the epidermis with formation of blebs and bullae either spontaneously or at the site of trauma.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cells infiltrates into the dermis layer and polymorphonuclear leukocyte infiltration into the epidermis layer resulting in an increase in the basal cell cycle. Additionally, hyperkeratotic and parakeratotic cells are present.

As used herein, "proliferating" and "proliferation" refer to cells undergoing mitosis.

The term "progenitor cell" refers to an undifferentiated cell which is capable of proliferation and giving rise to more progenitor cells having the ability to generate a large number of mother cells that can in turn give rise to differentiated, or differentiable daughter cells. As used herein, the term "progenitor cell" is also intended to encompass a cell which is sometimes referred to in the art as a "stem cell". In a preferred embodiment, the term "progenitor cell" refers to a generalized mother cell whose descendants (progeny) specialize, often in different directions, by differentiation, e.g., by acquiring completely individual characters, as occurs in progressive diversification of embryonic cells and tissues. For instance, a "hematopoietic progenitor cell" (or stem cell) refers to progenitor cells arising in bone marrow and other blood-associated organs and giving rise to such differentiated progeny as, for example, erythrocytes, lymphocytes and other blood cells.

As used herein, "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

As used herein, "immortalized cells" refers to cells which have been altered via chemical and/or recombinant means such that the cells have the ability to grow through an indefinite number of divisions in culture.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous gland of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Another carcinomatous epithelial growth is "papillomas", which refers to benign tumors derived from epithelium and having a papilloma virus as a causative agent; and "epiderinoidomas", which refers to a cerebral or meningeal tumor formed by inclusion of ectodermal elements at the time of closure of the neutral groove.

As used herein, a "transgenic animal" is any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by micro injection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. This term also includes transgenic animals in which the recombinant gene is silent, as for example, the FLP or CRE recombinase dependent constructs described in the art. Transgenic animals also include both constitutive and conditional "knock out" animals. The "non-human animals" of the invention include vertebrates such as rodents, non-human primates, swine, sheep, dog, cow, chickens, amphibians, reptiles, etc. Preferred non-human animals are miniature swine, or are selected from the rodent family including rat and mouse, most preferably mouse. The term "chimeric animal" is used herein to refer to animals in which the recombinant gene is found, or in which the recombinant is expressed in some but not all cells of the animal.

I. Establishment of the Micro-Organ Culture

A salient feature of the present micro-organ cultures and methods, according to the invention, is the ability to preserve the cellular microenvironment found in vivo for a particular tissue. The invention is based, in part, upon the discovery that under defined circumstances growth of cells in different tissue layers of an organ explant, e.g., mesenchymal and epithelial layers, can be activated to proliferate and mature in culture. Moreover, the cell-cell and cell-matrix interactions provided in the explant itself are sufficient to support cellular homeostasis, e.g., maturation, differentiation and segregation of cells in explant culture, thereby sustaining the microarchitecture and function of the tissue for prolonged period of time.

An example of physical contact between a cell and a non-cellular substrate (matrix) is the physical contact between an epithelial cell and its basal lamina. An example of physical contact between a cell and another cell includes actual physical contact maintained by, for example, intercellular cell junctions such as gap junctions and tight junctions. Examples of functional contact between one cell and another cell includes electrical or chemical communication between cells. For example, cardiomyocytes communicate with other cardiomyocytes via electrical impulses. In addition, many cells communicate with other cells via chemical messages, e.g., hormones which either diffuse locally (paracrine signaling and autocrine signaling) or are transported by the vascular system to more remote locations (endocrine signaling). Examples of paracrine signaling between cells are the messages produced by various cells (known as enteroendocrince cells) of the digestive tract, e.g., pyloric D cells which secrete somatostatin which in turn inhibits the release of gastrin by nearby pyloric gastric (G) cells.

Not wishing to be bound by any particular theory, this microarchitecture can be extremely important for the maintenance of the explant in minimal media, e.g., without exogenous sources of serum or growth factors, because the tissue can be sustained in such minimal media by paracrine and autocrine factors resulting from specific cellular interactions within the explant.

Moreover, the phrase "maintain, in vitro, their physical and/or functional contact" is not intended to exclude an isolated population of cells in which at least one cell develops physical and/or functional contact with at least one cell or noncellular substance with which it is not in physical and/or functional contact in vivo. An example of such a development is proliferation of at least one cell of the isolated population of cells.

In preferred embodiments, the populations of cells which make up the explant are isolated from an organ in a manner that preserves the natural affinity of one cell to another, e.g., to preserve layers of different cells if present in the explant. For example, in skin micro-organ cultures, keratinocytes of the epidermis remain associated with the stroma and the normal tissue architecture is preserved including the hair follicles and glands. This basic structure is common to all organs, for instance, which contain an epithelial component. Moreover, such an association facilitates intercellular communication. Many types of communication take place among animal cells. This is particularly important in differentiating cells where induction is defined as the interaction between one (inducing) and another (responding) tissue or cell, as a result of which the responding cells undergo a change in the direction of differentiation. Moreover, inductive interactions occur in embryonic and adult cells and can act to establish and maintain morphogenetic patterns as well as induce differentiation (Gurdon (1992) Cell 68: 185-199).

Furthermore, the micro-organ cultures prepared according to the invention preserve normal tissue architecture even when cultured for prolonged periods of time. This includes the maintenance of hair follicles, sweat glands and sebaceous glands in skin micro-organs in vitro according to their normal occurrence in vivo (see Examples VIII and FIGS. 10A-10C), or islets of Langerhans in the pancreas according to the normal occurrence in vivo (see Examples IV, V and VI). Because these cultures can be maintained in controlled and uniform conditions and yet closely resemble tissue in vivo, they provide a unique opportunity to observe, measure and control natural phenomena and the perturbation of natural phenomena arising from disease, aging or trauma. Furthermore, the ready availability of techniques to study individual cells at identified sites on the culture provide insights into the functioning of individual components of the tissue as they interact with each other as well as the whole tissue.

Examples of micro-organ cultures prepared according to the invention are described in the appended Examples, and can include a population of cells grouped in a manner that may include a plurality of layers so as to preserve the natural affinity of one cell to another. The proliferation of individual cells or groups of cells can be observed and followed by autoradiography or immunofluorescence.

As merely further exemplification, the appended examples demonstrate that the subject culture system provides for the replication of epithelial and stromal elements in vitro, in a system comparable to physiologic conditions. Importantly, the cells which replicate in this system segregate properly to form morphologically and histologically normal epidermal and dermal components.

In addition to isolating an explant which retains the cell-cell, cell-matrix and cell-stroma architecture of the originating tissue, the dimensions of the explant are important to the viability of the cells therein, e.g., where the micro-organ culture is intended to be sustained for prolonged periods of time, e.g., 7-21 days or longer. Accordingly, the dimensions of the tissue explant are selected to provide diffusion of adequate nutrients and gases, e.g., $O_2$, to every cell in the three dimensional micro-organ, as well as diffusion of cellular waste out of the explant so as to minimize cellular toxicity and concomitant death due to localization of the waste in the micro-organ. Accordingly, the size of the explant is determined by the requirement for a minimum level of accessibility to each cell in the absence specialized delivery structures or synthetic substrates. It has been discovered, as described herein, that this accessibility can be maintained if Aleph, an index calculated from the thickness and the width of the explant, is at least greater than approximately 1.5 $mm^{-1}$ As used herein, "Aleph" refers to a surface area to volume ratio given by a formula $1/x+1/a \geq 1.5$ $mm^{-1}$; whereinx=tissue thickness and a=width of tissue in millimeters. In preferred embodiments, the aleph of an explant is in the range of 1.5 to 25 $mm^{-1}$, more preferably in the range of 1.5 to 15 $mm^{-1}$, and even more preferably in the range of 1.5 to 10 $mm^{-1}$, though alephs in the range of 1.5 to 6.67 $mm^{-1}$, 1.5 to 3.33 $mm^{-1}$ are contemplated.

Accordingly, the present invention provides that the surface area to volume index of the tissue explant is maintained within a selected range. This selected range of surface area to volume index provides the cells access to nutrients and to avenues of waste disposal by diffusion in a manner similar to cells in a monolayer. This level of accessibility can be attained and maintained if the surface area to volume index, defined herein as "Aleph or Aleph index" is at least about 1.5 $mm^{-1}$. The third dimension has been ignored in determining the surface area to volume index because variation in the third dimension causes radiometric variation in both volume and surface area. However, when determining Aleph, a and x should be defined as the two smallest dimensions of the tissue slice.

Figure 6:
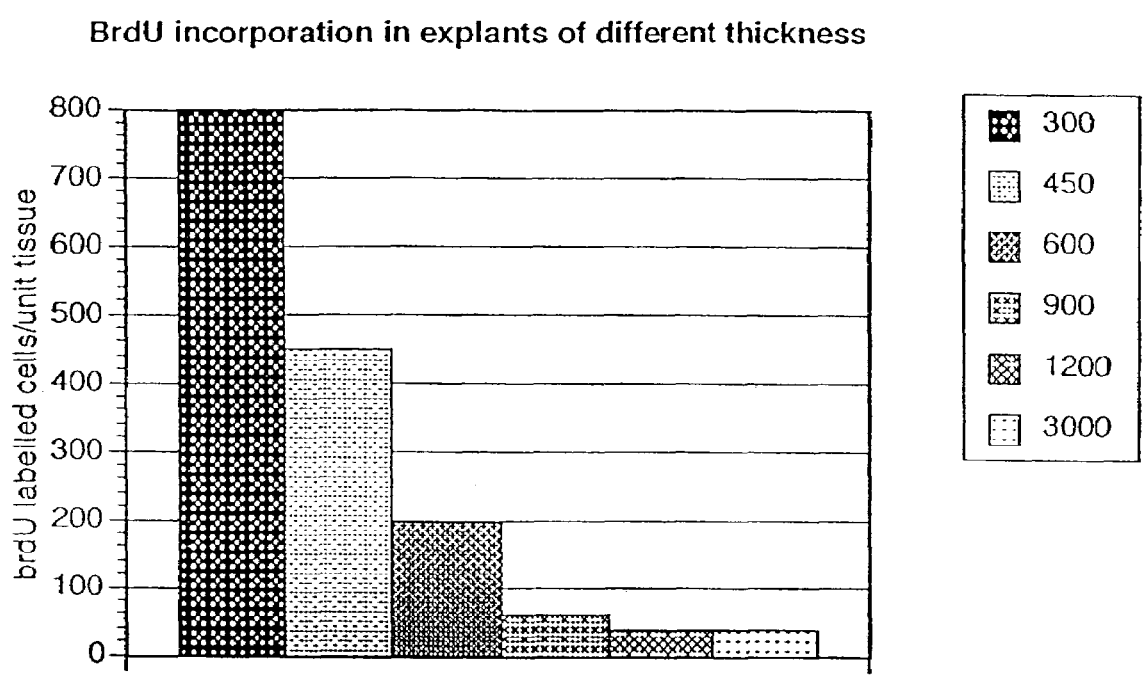
FIG. 6 is a histogram demonstrating the effect on epidermal proliferation of varying thickness (x) of guinea pig skin micro-organ cultures using BrdU incorporation where (a) has been kept constant at 4 mm.
Figure 8:
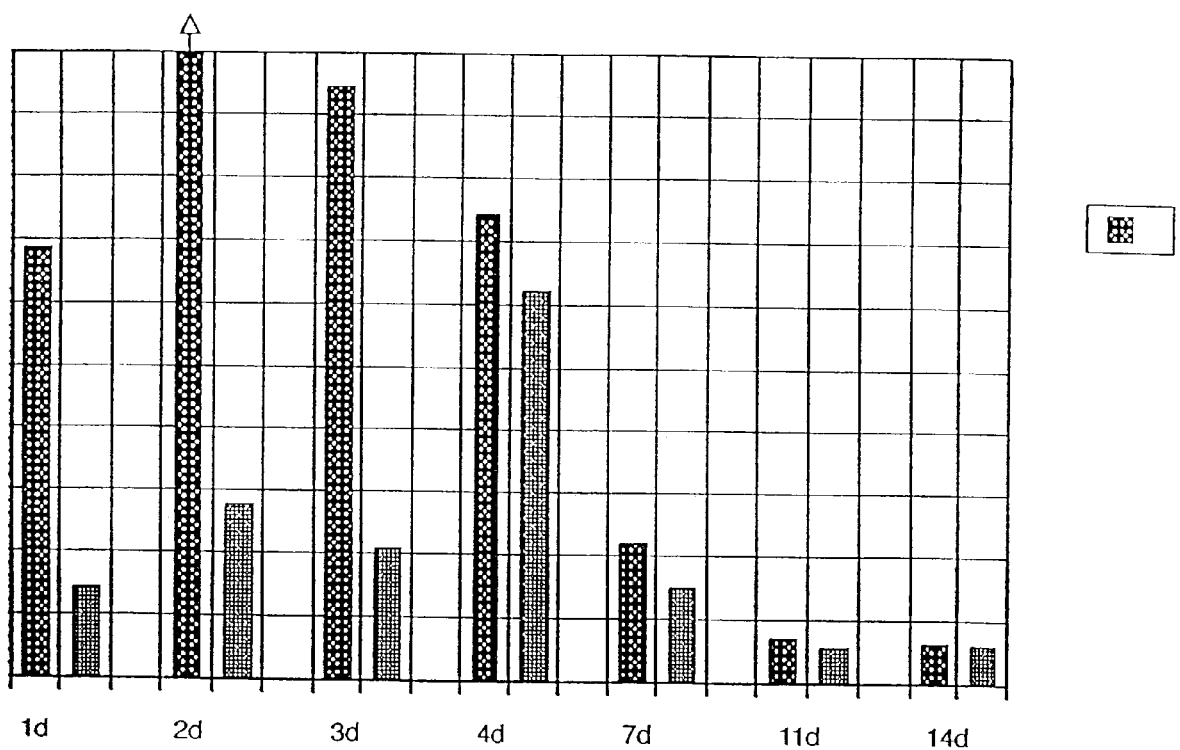
FIG. 8 is a histogram showing amounts of insulin released by adult pig pancreas micro-organ cultures.

Examples of Aleph are provided in Table I wherein, for example, a tissue having a thickness (x) of 0.1 mm and a width (a) of 1 mm would have an Aleph index of 11. In Example I, the tissue had x=0.3 mm and a=4 mm such that Aleph=3.48. In Example III, x is varied and a is constant at 4 mm. As illustrated in FIG. 6, proliferative activity is substantially reduced as the thickness of the explant increases. Accordingly, at 900 μm thickness, the number of proliferating cells in a micro-organ culture is about 10 fold less then in tissue from a similar source having a thickness of 300 μm. The Aleph index for a tissue having a thickness of 900 μm is 1.36 $mm^{-1}$, below the minimum described herein whereas the Aleph index for tissue having a thickness of 300 μm is 3.58 $mm^{-1}$, which is well within the range of defined herein.

TABLE 1

Different values for the surface area to volume ratio index "Aleph", as a function of a (width) and x (thickness) in $mm^{-1}$

| | WIDTH | | | | |
|---|---|---|---|---|---|
| x(mm) | a = 1 mm | a = 2 mm | a = 3 mm | a = 4 mm | a = 5 mm |
| 0.1 | 11 | 10.5 | 10.33 | 10.25 | 10.2 |
| 0.2 | 6 | 5.5 | 5.33 | 5.25 | 5.2 |
| 0.3 | 4.3 | 3.83 | 3.67 | 3.58 | 3.53 |
| 0.4 | 3.5 | 3 | 2.83 | 2.75 | 2.7 |
| 0.5 | 3 | 2.5 | 2.33 | 2.25 | 2.2 |
| 0.6 | 2.66 | 2.16 | 2 | 1.91 | 1.87 |
| 0.7 | 2.4 | 1.92 | 1.76 | 1.68 | 1.63 |
| 0.8 | 2.25 | 1.75 | 1.58 | 1.5 | 1.45 |
| 0.9 | 2.11 | 1.61 | 1.44 | 1.36 | 1.31 |
| 1 | 2 | 1.5 | 1.33 | 1.25 | 1.2 |
| 1.2 | 1.83 | 1.3 | 1.16 | 1.08 | 1.03 |
| 1.3 | 1.77 | 1.26 | 1.1 | 1.02 | 0.96 |
| 1.6 | 1.625 | 1.13 | 0.96 | 0.88 | 0.83 |
| 2 | 1.5 | 1 | 0.83 | 0.75 | 0.7 |

Again, not wishing to be bound by any particular theory, a number of factors provided by the three-dimensional culture system may contribute to its success:

(a) The appropriate choice of the explant size, e.g., by use of the above Aleph calculations, three-dimensional matrix provides appropriate surface area to volume ratio for adequate diffusion of nutrients to all cells of the explant, and adequate diffusion of cellular waste away from all cells in the explant.

(b) Because of the three-dimensionality of the matrix, various cells continue to actively grow, in contrast to cells in monolayer cultures, which grow to confluence, exhibit contact inhibition, and cease to grow and divide. The elaboration of growth and regulatory factors by replicating cells of the explant may be partially responsible for stimulating proliferation and regulating differentiation of cells in culture, e.g., even for the micro-organ culture which is static in terms of overall volume.

(c) The three-dimensional matrix retains a spatial distribution of cellular elements which closely approximate that found in the counterpart tissue in vivo.

(d) The cell-cell and cell-matrix interactions may allow the establishment of localized microenvironments conducive to cellular maturation. It has been recognized that maintenance of a differentiated cellular phenotypes requires not only growth/differentiation factors but also the appropriate cellular interactions. The present invention effectively mimics the tissue microenvironment.

As described in the illustrative examples below, micro-organ cultures from animals (including humans), such as derived from skin, pancreas, liver, kidney, duodenum, esophagus, bladder, bone marrow, thymus or spleen, have been isolated and grown for up to 21 days in culture. However, it is within the scope of the invention to maintain cultures for extended periods of time beyond 21 days.

II. Source of Explants for the Micro-Organ Culture

The subject micro-organ culture can be derived using explants isolated from, for example: skin and mucosa (including oral mucosa, gastrointestinal mucosa, nasal tract, respiratory tract, cervix and cornea); pancreas; liver; gallbladder; bile duct; lung; prostate; uterus; mammary gland; bladder tissue; and blood-associated organs such as thymus, spleen and bone marrow. Accordingly, in vitro culture equivalents of such organs can be generated. The tissue forming the explants can be diseased or normal (e.g., healthy tissue). For example, the organs from which the micro-organ explants of the invention are isolated can be affected by hyperproliferative disorders, e.g., psoriasis or keratosis; proliferation of virally-infected cells, e.g., hepatitis infected or papilloma virus infected; neoproliferative disorders, e.g., basal cell carcinoma, squamous cell carcinoma, sarcomas, or Wilm's tumors; or fibrotic tissue, e.g., from a cirrhotic liver or a pancreas undergoing pancreatitis.

Examples of animals from which the cells of the invention can be isolated include humans and other primates, swine, such as wholly or partially inbred swine (e.g., miniature swine and transgenic swine), rodents, etc.

III. The Growth Media

There are a large number of tissue culture media that exist for culturing cells from animals. Some of these are complex and some are simple. While it is expected that micro-organ cultures may grow in complex media, it has been shown here that the cultures can be maintained in a simple medium such as Dulbecco's Minimal Essential Media. Furthermore, although the cultures may be grown in a media containing sera or other biological extracts such as pituitary extract, it has been shown here that neither serum nor any other biological extract is required. Moreover, the organ cultures can be maintained in the absence of serum for extended periods of time. In preferred embodiments of the invention, growth factors are not included in the medium during maintenance of the cultures in vitro.

The point regarding growth in minimal media is important. At present, most media or systems for prolonged growth of mammalian cells incorporate undefined proteins or use feeder cells to provide proteins necessary to sustain such growth. Because the presence of such undefined proteins can interfere with the intended end use of the subject micro-organ cultures, it will generally be desirable to culture the explants under conditions to minimize the presence of undefined proteins.

As used herein the language "minimal medium" refers to a chemically defined medium which includes only the nutrients that are required by the cells to survive and proliferate in culture. Typically, minimal medium is free of biological extracts, e.g., growth factors, serum, pituitary extract, or other substances which are not necessary to support the survival and proliferation of a cell population in culture. For example, minimal medium generally includes at least one amino acid, at least one vitamin, at least one salt, at least one antibiotic, at least one indicator, e.g., phenol red, used to determine hydrogen ion concentration, glucose, and other miscellaneous components necessary for the survival and proliferation of the cells. Minimal medium is serum-free. A variety of minimal media are commercially available from Gibco BRL, Gaithersburg, Md., as minimal essential media.

However, while growth factors and regulatory factors need not be added to the media, the addition of such factors, or the inoculation of other specialized cells may be used to enhance, alter or modulate proliferation and cell maturation in the cultures. The growth and activity of cells in culture can be affected by a variety of growth factors such as insulin, growth hormone, somatomedins, colony stimulating factors, erytliropoietin, epidermal growth factor, hepatic erythropoietic factor (hepatopoietin), and liver-cell growth factor. Other factors which regulate proliferation and/or differentiation include prostaglandins, interleukins, and naturally-occurring negative growth factors, fibroblast growth factors, and members of the transforming growth factor-$\beta$ family.

The micro-organ cultures may be maintained in any suitable culture vessel such as 24 or 96 well microplates and may be maintained at 37° C. in 5% $CO_2$. The cultures may be shaken for improved aeration, the speed of shaking being for example 12 rpm.

With respect to the culture vessel in/on which (optionally) the subject micro-organ cultures are provided, it is noted that in the preferred embodiment such vessel may generally be of any material and/or shape. A number of different materials may be used to form the vessel, including but not limited to: nylon (polyamides), dacron (polyesters), polystyrene, polypropylene, polyacrylates, polyvinyl compounds (e.g., polyvinylchloride), polycarbonate (PVC), polytetrafluoroethylene (PTFE; teflon), thermanox (TPX), nitrocellulose, cotton, polyglycolic acid (PGA), cat gut sutures, cellulose, gelatin, dextran, etc. Any of these materials may be woven into a mesh. Where the micro-organ culture is itself to be implanted in vivo, it may be preferable to use biodegradable matrices such as poly glycolic acid, catgut suture material, or gelatin, for example. Where the cultures are to be maintained for long periods of time or cryopreserved, non-degradable materials such as nylon, dacron, polystyrene, polyacrylates, polyvinyls, teflons, cotton, etc. may be preferred. A convenient nylon mesh which could be used in accordance with the invention is Nitex, a nylon filtration mesh having an average pore size of 210 µm and an average nylon fiber diameter of 90 µm (#3-210/36, Tetko, Inc., N.Y.). Yet other embodiments are discussed below.

In an exemplary embodiment, pancreatic micro-organs containing islets of Langerhans are prepared as cultures of the present invention. The cultures are then provided in encapsulated form so as to avoid immune rejection. Three general (exemplary) approaches for encapsulation might be used. In the first, a tubular membrane is coiled in a housing that contains the micro-organ explants. The membrane is connected to a polymer graft that in turn connects the device to blood vessels. By manipulation of the membrane permeability, so as to allow free diffusion of glucose and insulin back and forth through the membrane, yet block passage of antibodies and lymphocytes, normnoglycemia can be maintained in pancreatectomized animals treated with this device (Sullivan et al (1991) Science 252:718).

In a second approach, hollow fibers containing the pancreatic explants are (optionally) immobilized in the polysaccharide alginate. When the device is placed intraperitoneally in diabetic animals, blood glucose levels can be lowered and good tissue compatibility observed (Lacey et al. (1991) Science 254:1782; see also Example VI). Accordingly, fibers can be pre-spun and subsequently loaded with the micro-organ-explants (Aebischer et al. U.S. Pat. No. 4,892,538; Aebischer et al. U.S. Pat. No. 5,106,627; Hoffman et al. (1990) Expt. Neurobiol. 110:39-44; Jaeger et al. (1990) Prog. Brain Res. 82:41-46; and Aebischer et al. (1991) J. Biomech Eng. 113: 178-183).

Third, the micro-organ islet explants can be placed in microcapsules composed of alginate or polyacrylates (see, for example, Lim et al. (1980) Science 210:908; O'Shea et al. (1984) Biochim. Biochys. Acta 840:133; Sugamori et al (1989) Trans Am. Soc. Artif. Intern. Organs 35:791; Levesque et al. (1992) Endocrinology 130:644; and Lim et al. (1992) Transplantation 53:1180).

Finally, it is noted that the culture medium in which the micro-organ cultures of the present invention are maintained can be collected as a source of conditioned medium. The term "conditioned media" refers to the supernatant, e.g. free of the cultured cells/tissue, resulting after a period of time in contact with the cultured cells such that the media has been altered to include certain paracrine and/or autocrine factors produced by the cells and secreted into the culture. Examples of such products are insulin, various growth factors, and hormones. This conditioned medium can be used as culture medium for other types of cell and tissue culture. Alternatively, the conditioned medium can be employed as a source of novel cell products such as growth factors. Such products can be fractionated and purified or substantially purified from the conditioned medium.

IV. Measuring the Biological Properties of Micro-Organ Culture

The micro-organ cultures of the present invention derived from normal tissue have been shown to maintain a state of homeostasis with proliferation of constituent cells without overall growth of the tissue.

Methods of measuring cell proliferation are well known in the art and most commonly include determining DNA synthesis characteristic of cell replication. There are numerous methods in the art for measuring DNA synthesis, any of which may be used according to the invention. In an embodiment of the invention, DNA synthesis has been determined using a radioactive label ($^3$H-thymidine) or labeled nucleotide analogues (BrdU) for detection by immunofluorescence.

Micro-organ cultures can be formed and maintained not only by the proliferation of mature cells but also by the active participation of precursor cells including in some instances, embryonic cells. The micro-organ cultures have been shown to present a suitable environment for preserving, identifying, isolating and facilitating the natural evolution of these precursor cells. For example, the immature cells of the basal layer have been observed to become mature keratinocytes in skin micro-organ cultures. Similarly, embryonic pancreatic cells can provide a mature pancreatic epithelium in micro-organ cultures. The maturation of precursor cells and their subsequent functioning as adult cells can be monitored by measuring secretion of specialized products such as specific keratins in epidermal cells and insulin, Glut 2 and glucagon in pancreatic epithelia, and albumin and Factor VIII in liver micro-organ cultures.

The micro-organ cultures prepared according to the invention preserve the normal tissue architecture that is present in vivo. As set out above, this includes maintenance of hair follicles, sweat glands and sebaceous glands in skin micro-organs in vitro, according to the normal occurrence in vivo and insulin and glucagon secreting cells in pancreatic micro-organs. Because these cultures can be maintained in controlled and uniform conditions and yet they closely resemble the microarchitecture of the organ in vivo, they provide a unique opportunity to observe, measure and control natural phenomena and the perturbation of natural phenomena arising from disease, aging or trauma. Furthermore, the ready availability of techniques to study individual cells at identified sites on the culture, provides insights into the functioning of individual components of the organs and their interact with each other as well as the whole organ.

Furthermore, the subject micro-organ cultures are maintainable in culture for extended periods of time. Preferably, the micro-organ cultures are maintainable in culture for at least about twenty-four hours, more preferably for at least about two days, yet more preferably for at least about five days, still more preferably at least about seven days, still further preferably for at least about two weeks or more. The micro-organ cultures of the invention are typically maintained in culture for at least seven days. To illustrate, skin micro-organ cultures from human, mouse, guinea pig, and rat skin have been maintained in culture for at about least twenty-one days.

As used herein, the language "maintainable in culture" refers to the population of cells of a tissue explant of which at least about 60%, preferably at least about 70%, more preferably at least about 80%, yet more preferably at least about 90%, most preferably 95% or more of the cells remain viable in culture after a certain period of time.

In a preferred embodiment, the ratio of cell proliferation to cell loss, e.g., by death or sloughing, of the cells in the micro-organ cultures is equal to one, i.e., the number of cells proliferating is equal to the number of cells lost. In another embodiment of the present invention, the ratio of cell proliferation to cell loss of the cells in the micro-organ cultures is greater than one, i.e., the cells are proliferating at a greater rate than the cells are being lost. In the instance of the latter, the micro-organ culture is understood to include a population of cells which is being amplified.

V. Application of Micro-Organ Cultures

Exemplary applications for the micro-organ cultures of the present invention include the following:

(a) identification of factors involved in normal homeostasis of tissues and organs;

(b) studying the effect on the normal homeostasis of tissues and cells of an organ with respect to changes in the environment including changes in nutrients and the presence of potentially toxic agents;

(c) understanding the pathway of changes in the tissues and cells of an organ that are triggered at the beginning and during pathogenesis or trauma;

(d) identification of repair mechanisms that reverse the adverse effects in an altered environment associated with pathogenesis or trauma;

(e) developmental regulation of cells that differentiate during the normal homeostasis of the tissue.

(f) developmental regulation of specialized structures within an organ, such as hair follicles;

(g) organ supplementation/transplantation where parts of an individual's organ remain but are insufficient for replacing or regenerating damaged tissue such as occurs in patients with chronic skin ulcers, various forms of diabetes, or chronic liver failure;

(h) as a tissue/organ equivalent for drug screening and cytotoxicity studies;

(i) as a diagnostic assay for proliferative disorders;

(j) as a source of novel growth factors;
(k) as a source of stem/progenitor cells;
(l) as a source of inducing molecules;
(m) as a screen for inducing molecules;

To further illustrate, the present method can be used to generate skin equivalents in the form of micro-organ cultures. By way of background, it is noted that numerous attempts have been described for growing epithelial cells in such a way as to mimic human skin for purposes of wound treatment, in particular treatment of burns. The skin consists of two types of tissue. These are: (1) the stroma or dermis which includes fibroblasts that are loosely dispersed within a high density collagen matrix as well as nerves, blood vessels and fat cells; (2) the epidermis which includes an epidermal basal layer of tightly packed, actively proliferating immature epithelial cells. As the cells of the basal layer replicate, some of the young cells remain in the basal layer while others migrate outward, increase in size and eventually develope an envelop resistant to detergents and reducing agents. In humans, a cell born in the basal layer takes about 2 weeks to reach the edge or outer layer after which time the cells die and are shed. The skin contains various structures including hair follicles, sebaceous glands and sweat glands. Hair follicles are formed from differentiating keratinocytes that densely line invaginations of the epidermis. The open ended vesicles that formed from such invaginations collect and concentrate the secreted keratin and a hair filament results. Alternatively, epidermal cells lining an invagination may secrete fluids (sweat gland) or sebum (sebaceous gland). The regulation of formation and proliferation of these structures is unknown. The constant renewal of healthy skin is accomplished by a balanced process in which new cells are being produced and aged cells die. There is a need to understand how this precise regulation comes about in order to counteract abnormal events occurring in aging, and also through disease and trauma that disrupt the balance.

In one embodiment of the invention, the microarchitecture of the micro-organ culture mimics or is substantially the same as that of skin in vivo, e.g., it has an epithelial tissue/connective tissue structure. For example, in skin micro-organ cultures, keratinocytes of the epidermis remain associated with the connective tissue-and the normal tissue architecture is preserved including the hair follicles. The micro-organ culture which is obtained from a skin tissue section can also include a basal lamina supporting the epidermal cells, an extracellular matrix which includes the dermal cells, and at least one invagination, e.g., at least one hair follicle. The association between skin epithelial tissue and the skin connective tissue facilitates intercellular communication. Moreover, full thickness skin can be grown in a variety of ways allowing an air interface. Exposure of the keratinocytes of the explant to air promotes a more rapid differentiation of keratinocytes and more extensive secretion of keratin layers, which may be very important in skin penetration studies.

Finally, it is noted that recent studies have indicated that the skin is an integral and active element of the immune system (Cooper et al., (1987) The mechanobullous disease. In: Dermatology in General Medicine, 3d. Ed., McGraw Hill, N.Y. (pp.610-626). One of the major cell types in the skin which is responsible for various immune activities is the Langerhans cell. These cells may be prepared from fresh skin samples and added to the three-dimensional skin culture to produce an immunologically complete tissue system. Growth of these cells in the culture for long periods of time by conventional tissue culture techniques is difficult. The ability to grow these cells in a three-dimensional system would be of great importance in all aspects of study including engraftment, cytoxicity, and disease mechanisms. This type of skin culture system would have the greatest impact on research involving auto-immune disorders which have direct or indirect cutaneous involvement (lupus erythematosis, bullous pemphigoid, etc.). Accordingly, the micro-organ cultures of the present invention can be used to study proliferative/differentiative disorders under conditions in which immunological aspects of the disease are minimized. An exemplary drug screening assay can be derived using psoriatic skin explants in order to identify agents which can inhibit proliferation of the hyperplastic epithelial cells.

The skin is merely an example of a tissue which can be grown as a micro-organ culture having epithelial tissue which is supported by stromal tissue. Other tissues including epithelial tissue can be grown as micro-organ cultures of the present invention. Epithelial tissues are found in every part of the body where an interface between an organ and the environment arise. Epithelial cells cycle continuously in an uninjured body and form the covering tissue for all the free surfaces in the body including the skin. In some cases, such as in the pancreas, the epithelial cells line numerous invaginations and secrete enzymes into open spaces that enable the organ to function. The lung is another example of a highly invaginated organ, each invagination in the lung being lined with epithelial cells through which air diffuses from the environment in to the body. Once again, these epithelial cells have characteristic properties. The lining of the gut is also composed of specialized epithelial cells that not only form a barrier but also contain specialized structures for selectively absorbing food. All the epithelia are supported by connective tissue. Still another organ comprising important cell-stromal interactions is the bone marrow.

Thus, in another embodiment of the present invention, microarchitecture of a micro-organ pancreas culture mimics or is substantially the same as that of the source pancreas in vivo, e.g., it has an epithelial tissue/connective tissue structure. For example, pancreas micro-organ cultures include pancreatic epithelial cells, e.g., islet cells, remain associated with the pancreatic connective tissue. In the pancreas micro-organ culture, therefore, the normal tissue architecture is preserved and the normal pancreatic epithelial cell products, e.g., insulin and glucagon are produced.

In another embodiment, the present invention provides for the generation of micro-organ cultures derived from the bone marrow, which cultures preserve the microarchitecture of the in vivo organ. As described in Example XV, bone marrow micro-organs have been isolated in culture to derive a system comparable to physiologic conditions.

The bone marrow cultures of the present invention may be used for treating diseases or conditions which destroy healthy bone marrow cells or depress their functional ability. Implantation of the subject micro-organs can be effective in the treatment of hematological malignancies and other neoplasias which involve the bone marrow. This aspect of the invention is also effective in treating patients whose bone marrow has been adversely affected by the environmental factors (e.g., radiation, toxins, etc). While reimplantation of explants derived from the patients own marrow are generally preferable, it is noted that such explants can be allogenic, e.g., from another member of the same species, or xenogenic, e.g., from another organism. An exemplary xenogenic implant could be a micro-organ culture derived from a miniature swine for implantation in a human.

Moreover, long-term growth of human hematopoietic progenitors is possible if they are provided with the necessary stromal-derived growth/regulatory factors. Such interactions are provided by the subject micro-organs, rendering these explants as sources of stem and progenitor cells. In general, hematopoietic progenitor cells of the marrow colonize ("seed") the natural packets formed in the stromal matrix of the bone marrow micro-organ. The primary rate limiting factor in the growth of marrow stromal cells is the relatively low mitotic index of the fibroblasts included among the marrow stromal cells. Accordingly, where the growth of these cells and their disposition of extracellular matrix components is desired to be enhanced, the explant can be contacted with such agents as hydrocortisones or other fibroblast growth factors.

If the bone marrow is to be cultured in order to treat certain patients with metastatic disease or hematological malignancies, the marrow obtained from the patients should be "purged" of abnormally proliferating cells by physical or chemotherapeutic means prior to culturing.

The conditioned medium from a bone marrow micro-organ culture of the present invention can be used as a source of novel or known lymphokines, e.g., as a source of interleukins.

The invention contemplates, in one aspect, the use of the subject micro-organ cultures for transplantation in an organism. As used herein the terms "administering","introducing", and "transplanting" are used interchangeably and refer to the placement of the cell populations of the invention into a subject, e.g., an allogeneic or a xenogeneic subject, by a method or route which results in localization of the cells to a desired site. The cell populations can be administered to a subject by any appropriate route which results in delivery of the cells to a desired location in the subject where at least a portion of the cells remain viable. It is preferred that at least about 5%, preferably at least about 10%, more preferably at least about 20%, yet more preferably at least about 30%, still more preferably at least about 40%, and most preferably at least about 50% or more of the cells remain viable after administration to a subject. The period of viability of the cells after administration to a subject can be as short as a few hours, e.g., twenty-four hours, to a few days, to as long as a few weeks to months. Methods of administering populations of cells of the invention include implantation of cells into the visceral or the parietal peritoneum, for example into a pouch of the omentum, implantation of cells into or onto an organ of the recipient subject, e.g., pancreas, liver, spleen, skin. The micro-organs of the invention can also be administered to a subject by implantation under, e.g., a kidney capsule.

As used herein, the term "subject" refers to mammals, e.g., primates, e.g., humans. A "xenogeneic subject" as used herein is a subject into which cells of another species are introduced or are to be introduced. An "allogeneic subject" is a subject into which cells of the same species are introduced or are to be introduced. Donor subjects are subjects which provide the cells, tissues, or organs, which are to be placed in culture and/or transplanted to a recipient subject. Recipient subjects can be either xenogeneic or allogeneic subject. Donor subjects can also provide cells, tissues, or organs for reintroduction into themselves, i.e. for autologous transplantation.

To facilitate transplantation of the cell populations which may be subject to immunological attack by the host, e.g., where xenogenic grafting is used, such as swine-human transplantations, the micro-organ can be inserted into or encapsulated by rechargeable or biodegradable devices and then transplanted into the recipient subject. Gene products produced by such cells can then be delivered via, for example, polymeric devices designed for the controlled delivery compounds, e.g., drugs, including proteinaceous biopharmaceuticals. A variety of biocompatible polymers (including hydrogels), including both biodegradable and non-degradable polymers, can be used to form an implant for the sustained release of a gene product of the cell populations of the invention at a particular target site. The generation of such implants is generally known in the art. See, for example, *Concise Encyclopedia of Medical & Dental Materials*, ed. By David Williams (MIT Press: Cambridge, Mass., 1990); the Sabel et al. U.S. Pat. No. 4,883,666; Aebischer et al. U.S. Pat. No. 4,892,538; Aebischer et al. U.S. Pat. No. 5,106,627; Lim U.S. Pat. No. 4,391,909; and Sefton U.S. Pat. No. 4,353,888. Cell populations of the invention can be administered in a pharmaceutically acceptable carrier or diluent, such as sterile saline and aqueous buffer solutions. The use of such carriers and diluents is well known in the art.

In one embodiment, the micro-organ cultures of the present invention can be employed for wound healing. Repair of skin lesions is known to be a highly complex process that includes primary epithelial cell migration as well as replication of epidermal cells in response to molecular signals from underlying connective tissue. Skin micro-organ cultures are described herein as a model for wound healing. Under controlled culture conditions, factors controlling healing can be carefully monitored. Furthermore, because the micro-organ culture is isolated from the natural blood supply, analysis of the healing process can be done without the additional complexity of blood borne factors or cells. Normal epidermis has a low mitotic activity with cells cycling every 200-300 hours. When the epidermis is wounded, a burst of mitotic activity takes place so that the cells divide up to 10 times faster depending on the conditions and severity of the wound (Pinkus H.(1951) *J Invest. Dermatol.* 16:383-386).

As demonstrated in Example II, skin micro-organ cultures show increased proliferation of up to 10 fold for several days. In this example, the edge of a wound is comparable to the micro-organ culture. This increased proliferation mimics the events that are associated with wounding and provides a unique opportunity to study the process of wound healing. Moreover, the appended examples demonstrate in vivo that the epidermal explants of the present invention can be applied to chronic wounds (example IX) and can form a viable implant capable of growing hair (example XI).

Moreover, the subject epidermal micro-organs can be used in the treatment of burn patients. The need for a skin replacement for burn patients is evident. Several centers in the United States and Europe have utilized cultured human keratinocyte allografts and autografts to permanently cover the wounds of burns and chronic ulcers (Eisinger et al., (1980) *Surgery* 88:287-293; Green et al., (1979) *Proc. Natl. Acad. Sci. USA* 76:5665-5668; Cuono et al., (1987) *Plast. Reconstr. Surg.* 80:626-635). These methods are often unsuccessful and recent studies have indicated that blistering and/or skin fragility in the healed grafts may exist because of an abnormality in one or more connective tissue components formed under the transplanted epidermal layer (Woodley et al., (1988) *JAMA* 6:2566-2571). The skin culture system of the present invention provides a skin equivalent of both epidermis and dermis and should overcome problems characteristic of currently used cultured keratinocyte grafts.

In yet another embodiment, the micro-organ culture system of the invention may afford a vehicle for introducing genes and gene products in vivo for use in gene therapies. For example, using recombinant DNA techniques, a gene for which a patient is deficient could be placed under the control of a viral or tissue-specific promoter. The recombinant DNA construct can be used to transform or transfect all or certain of the cells in the subject micro-organ culture system. The micro-organ culture which expresses the active gene product could be implanted into an individual who is deficient for that product.

The use of the subject micro-organ culture in gene therapy has a number of advantages. Firstly, since the culture comprises eukaryotic cells, the gene product will be properly expressed and processed in culture to form an active product. Secondly, gene therapy techniques are useful only if the number of transfected cells can be substantially enhanced to be of clinical value, relevance, and utility; the subject cultures allow for expansion of the number of transfected cells and amplification.

In a further embodiment of the invention, the transgenic micro-organ cultures may be used to facilitate gene transduction. For example, and not by way of limitation, a micro-organ culture comprising a recombinant virus expression vector may be used to transfer the recombinant virus into cells brought into contact with the culture, e.g., by implantation, thereby simulating viral transmission in vivo. Accordingly, this system can be a more efficient way of accomplishing gene transduction than are current techniques for DNA transfection.

Accordingly, the cells of the micro-organ cultures of the present invention can be modified to express a gene product. As used herein, the phrase "gene product" refers to proteins, peptides and functional RNA molecules. Generally, the gene product encoded by the nucleic acid molecule is the desired gene product to be supplied to a subject. Examples of such gene products include proteins, peptides, glycoproteins and lipoproteins normally produced by an organ of the recipient subject. For example, gene products which may be supplied by way of gene replacement to defective organs in the pancreas include insulin, amylase, protease, lipase, trypsinogen, chymotrypsinogen, carboxypeptidase, ribonuclease, deoxyribonuclease, triacylglycerol lipase, phospholipase $A_2$, elastase, and amylase; gene products normally produced by the liver include blood clotting factors such as blood clotting Factor VIII and Factor IX, UDP glucuronyl transferase, ornithine transcarbanoylase, and cytochrome p450 enzymes, and adenosine deaminase, for the processing of serum adenosine or the endocytosis of low density lipoproteins; gene products produced by the thymus include serum thymic factor, thymic humoral factor, thymopoietin, and thymosin $\alpha_1$; gene products produced by the digestive tract cells include gastrin, secretin, cholecystokinin, somatostatin, and substance P. Alternatively, the encoded gene product is one which induces the expression of the desired gene product by the cell (e.g., the introduced genetic material encodes a transcription factor which induces the transcription of the gene product to be supplied to the subject). In still another embodiment, the recombinant gene can provide a heterologous protein, e.g., not native to the cell in which it is expressed. For instance, various human MHC components can be provided to non-human micro-organs to support engraftment in a human recipient. Alternatively, the transgene is one which inhibits the expression or action of a donor MHC gene product normally expressed in the micro-organ explant.

A nucleic acid molecule introduced into a cell is in a form suitable for expression in the cell of the gene product encoded by the nucleic acid. Accordingly, the nucleic acid molecule includes coding and regulatory sequences required for transcription of a gene (or portion thereof) and, when the gene product is a protein or peptide, translation of the nucleic acid molecule include promoters, enhancers and polyadenylation signals, as well as sequences necessary for transport of an encoded protein or peptide, for example N-terminal signal sequences for transport of proteins or peptides to the surface of the cell or secretion.

Nucleotide sequences which regulate expression of a gene product (e.g., promoter and enhancer sequences) are selected based upon the type of cell in which the gene product is to be expressed and the desired level of expression of the gene product. For example, a promoter known to confer cell-type specific expression of a gene linked to the promoter can be used. A promoter specific for myoblast gene expression can be linked to a gene of interest to confer muscle-specific expression of that gene product. Muscle-specific regulatory elements which are known in the art include upstream regions from the dystrophin gene (Klamut et al., (1989) *Mol. Cell Biol.* 9:2396), the creatine kinase gene (Buskin and Hauschka, (1989) *Mol. Cell Biol.* 9:2627) and the troponin gene (Mar and Ordahl, (1988) *Proc. Natl. Acad. Sci. USA.* 85:6404), Negative response elements in keratin genes mediate transcriptional repression (Jho Sh et al, (2001). J Biol Chem). Regulatory elements specific for other cell types are known in the art (e.g., the albumin enhancer for liver-specific expression; insulin regulatory elements for pancreatic islet cell-specific expression; various neural cell-specific regulatory elements, including neural dystrophin, neural enolase and A4 amyloid promoters). Alternatively, a regulatory element which can direct constitutive expression of a gene in a variety of different cell types, such as a viral regulatory element, can be used. Examples of viral promoters commonly used to drive gene expression include those derived from polyoma virus, Adenovirus 2, cytomegalovirus and Simian Virus 40, and retroviral LTRs. Alternatively, a regulatory element which provides inducible expression of a gene linked thereto can be used. The use of an inducible regulatory element (e.g., an inducible promoter) allows for modulation of the production of the gene product in the cell. Examples of potentially useful inducible regulatory systems for use in eukaryotic cells include hormone-regulated elements ( e.g., see Mader, S. and White, J. H. (1993) *Proc. Natl. Acad. Sci. USA* 90:5603-5607), synthetic ligand-regulated elements (see, e.g., Spencer, D. M. et al 1993) *Science* 262:1019-1024) and ionizing radiation-regulated elements (e.g., see Manome, Y. Et al. (1993) *Biochemistry* 32:10607-10613; Datta, R. et al. (1992) *Proc. Natl. Acad. Sci. USA* 89:1014-10153). Additional tissue-specific or inducible regulatory systems which may be developed can also be used in accordance with the invention.

There are a number of techniques known in the art for introducing genetic material into a cell that can be applied to modify a cell of the invention. In one embodiment, the nucleic acid is in the form of a naked nucleic acid molecule. In this situation, the nucleic acid molecule introduced into a cell to be modified consists only of the nucleic acid encoding the gene product and the necessary regulatory elements. Alternatively, the nucleic acid encoding the gene product (including the necessary regulatory elements) is contained within a plasmid vector. Examples of plasmid expression vectors include CDM8 (Seed, B. (1987) *Nature* 329:840) and pMT2PC (Kaufman, et al. (1987) *EMBO J.* 6:187-195). In another embodiment, the nucleic acid molecule to be introduced into a cell is contained within a viral vector. In this situation, the nucleic acid encoding the gene product is inserted into the viral genome (or partial viral genome). The regulatory elements directing the expression of the gene product can be included with the nucleic acid inserted into the viral genome (i.e., linked to the gene inserted into the viral genome) or can be provided by the viral genome itself.

Naked nucleic acids can be introduced into cells using calcium-phosphate mediated transfection, DEAE-dextran mediated transfection, electroporation, liposome-mediated transfection, direct injection, and receptor-mediated uptake.

Naked nucleic acid, e.g., DNA, can be introduced into cells by forming a precipitate containing the nucleic acid and calcium phosphate. For example, a HEPES-buffered saline solution can be mixed with a solution containing calcium chloride and nucleic acid to form a precipitate and the precipitate is then incubated with cells. A glycerol or dimethyl sulfoxide shock step can be added to increase the amount of nucleic acid taken up by certain cells. $CaPO_4$-mediated transfection can be used to stably (or transiently) transfect cells and is only applicable to in vitro modification of cells. Protocols for $CaPO_4$-mediated transfection can be found in Current Protocols in Molecular Biology, Ausubel, F. M. et al. (eds.) Greene Publishing Associates, (1989), Section 9.1 and in Molecular Cloning: A Laboratory Manual, 2nd Edition, Sambrook et al. Cold Spring Harbor Laboratory Press, (1989), Sections 16.32-16.40 or other standard laboratory manuals.

Naked nucleic acid can be introduced into cells by forming a mixture of the nucleic acid and DEAE-dextran and incubating the mixture with the cells. A dimethylsulfoxide or chloroquine shock step can be added to increase the amount of nucleic acid uptake. DEAE-dextran transfection is only applicable to in vitro modification of cells and can be used to introduce DNA transiently into cells but is not preferred for creating stably transfected cells. Thus, this method can be used for short term production of a gene product but is not a method of choice for long-term production of a gene product. Protocols for DEAE-dextran-mediated transfection can be found in Current Protocols in Molecular Biology, Ausubel, F. M. et al. (eds.) Greene Publishing Associates (1989), Section 9.2 and in Molecular Cloning: A Laboratory Manual, 2nd Edition, Sambrook et al. Cold Spring Harbor Laboratory Press, (1989), Sections 16.41-16.46 or other standard laboratory manuals.

Naked nucleic acid can also be introduced into cells by incubating the cells and the nucleic acid together in an appropriate buffer and subjecting the cells to a high-voltage electric pulse. The efficiency with which nucleic acid is introduced into cells by electroporation is influenced by the strength of the applied field, the length of the electric pulse, the temperature, the conformation and concentration of the DNA and the ionic composition of the media. Electroporation can be used to stably (or transiently) transfect a wide variety of cell types. Protocols for electroporating cells can be found in Current Protocols in Molecular Biology, Ausubel F. M. et al. (eds.) Greene Publishing Associates, (1989), Section 9.3 and in Molecular Cloning: A Laboratory Manual, 2nd Edition, Sambrook et al. Cold Spring Harbor Laboratory Press, (1989), Sections 16.54-16.55 or other standard laboratory manuals.

Another method by which naked nucleic acid can be introduced into cells includes liposome-mediated transfection (lipofection). The nucleic acid is mixed with a liposome suspension containing cationic lipids. The DNA/liposome complex is then incubated with cells. Liposome mediated transfection can be used to stably (or transiently) transfect cells in culture in vitro. Protocols can be found in Current Protocols in Molecular Biology, Ausubel F. M. et al. (eds.) Greene Publishing Associates, (1989), Section 9.4 and other standard laboratory manuals. Additionally, gene delivery in vivo has been accomplished using liposomes. See for example Nicolau et al. (1987) *Meth. Enz.* 149:157-176; Wang and Huang (1987) *Proc. Natl. Acad. Sci. USA* 84:7851-7855; Brigham et al. (1989) *Am. J Med. Sci*. 298:278; and Gould-Fogerite et al. (1989) *Gene* 84:429-438.

Naked nucleic acid can also be introduced into cells by directly injecting the nucleic acid into the cells. For an in vitro culture of cells, DNA can be introduced by microinjection. Since each cell is microinjected individually, this approach is very labor intensive when modifying large numbers of cells. However, a situation wherein microinjection is a method of choice is in the production of transgenic animals (discussed in greater detail below). In this situation, the DNA is stably introduced into a fertilized oocyte which is then allowed to develop into an animal. The resultant animal contains cells carrying the DNA introduced into the oocyte. Direct injection has also been used to introduce naked DNA into cells in vivo (see e.g., Acsadi et al. (1991) Nature 332:815-818; Wolff et al. (1990) *Science* 247:1465-1468). A delivery apparatus (e.g., a "gene gun") for injecting DNA into cells in vivo can be used. Such an apparatus is commercially available (e.g., from Bio-Rad).

Naked nucleic acid can be complexed to a cation, such as polylysine, which is coupled to a ligand for a cell-surface receptor to be taken up by receptor-mediated endocytosis (see for example Wu, G. and Wu, C. H. (1988) *J Biol. Chem.* 263: 14621; Wilson et al. (1992) *J. Biol. Chem.* 267:963-967; and U.S. Pat. No. 5,166,320). Binding of the nucleic acid-ligand complex to the receptor facilitates uptake of the DNA by receptor-mediated endocytosis. Receptors to which a DNA-ligand complex have targeted include the transferrin receptor and the asialoglycoprotein receptor. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122-2126). Receptor-mediated DNA uptake can be used to introduce DNA into cells either in vitro or in vivo and, additionally, has the added feature that DNA can be selectively targeted to a particular cell type by use of a ligand which binds to a receptor selectively expressed on a target cell of interest.

Generally, when naked DNA is introduced into cells in culture (e.g., by one of the transfection techniques described above) only a small fraction of cells (about 1 out of $10^5$) typically integrate the transfected DNA into their genomes (i.e., the DNA is maintained in the cell episomally). Thus, in order to identify cells which have taken up exogenous DNA, it is advantageous to transfect nucleic acid encoding a selectable marker into the cell along with the nucleic acid(s) of interest. Preferred selectable markers include those which confer resistance to drugs such as G418, hygromycin and methotrexate. Selectable markers may be introduced on the same plasmid as the gene(s) of interest or may be introduced on a separate plasmid.

A preferred approach for introducing nucleic acid encoding a gene product into a cell is by use of a viral vector containing nucleic acid, e.g. a cDNA, encoding the gene product. Infection of cells with a viral vector has the advantage that a large proportion of cells receive the nucleic acid which can obviate the need for selection of cells which have received the nucleic acid. Additionally, molecules encoded within the viral vector, e.g. a cDNA contained in the viral vector, are expressed efficiently in cells which have taken up viral vector nucleic acid and viral vector systems can be used either in vitro or in vivo.

Defective retroviruses are well characterized for use in gene transfer for gene therapy purposes (for review see Miller, A. D. (1990) *Blood* 76:271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ψCrip, ψ2 and ψAm. Retroviruses have been used to introduce a variety of genes into many different cell types, including epithelial cells endothelial cells, lymphocytes, myoblasts, hepatocytes, bone marrow cells, in vitro and/or in vivo (see for example Eglitis, et al. (1985) Science 230:1395-1398; Danosand Mulligan (1988) *Proc. Natl. Acad. Sci. USA* 85:6460-6464; Wilson et al. (1988) *Proc. Natl. Acad. Sci USA* 85:3014-3018; Armentano et al., (1990) Proc. Natl. Acad. Sci. USA 87: 6141-6145; Huber et al. (1991) Proc. Natl. Acad. Sci. USA 88:8039-8043; Feri et al. (1991) Proc. Natl. Acad. Sci. USA 88:8377-8381; Chowdhury et al. (1991) *Science* 254:1802-1805; van Beusechem et al. (1992) Proc. Natl. Acad. Sci USA 89:7640-7644; Kay et al. (1992) *Human Gene Therapy* 3:641-647; Dai et al. (1992) *Proc. Natl. Acad. Sci. USA* 89:10892-10895; Hwu et al (1993) J. Immunol. 150: 4104-4115; U.S. Pat. Nos. 4,868,116; 4,980,286; PCT application WO 89/07136; PCT application WO 89/02468; PCT application WO 89/05345; and PCT application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol* 57:267). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics In Micro. And Immunol.* (1992) 158: 97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984)*Proc. Natl. Acad. Sci. USA* 81:6466-6470; Tratschin et al. (1985) *Mol. Cell Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be interest to be expressed by a cell is not readily assayable, an expression system can first be optimized using a reporter gene linked to the regulatory elements and vector to be used. The reporter gene encodes a gene product which is easily detectable and, thus, can be used to evaluate efficacy of the system. Standard reporter genes used in the art include genes encoding β-galactosidase, chloramphenicol acetyl transferase, luciferase, GFP/EGFP and human growth hormone.

When the method used to introduce nucleic acid into a population of cells results in modification of a large proportion of the cells and efficient expression of the gene product by the cells (e.g., as is often the case when using a viral expression vector), the modified population of cells may be used without further isolation or subcloning of individual cells within the population. That is, there may be sufficient production of the gene product by the population of cells such that no further cell isolation is needed. Alternatively, it may be desirable to grow a homogenous population of identically modified cells from a single modified cell to isolate cells which efficiently express the gene product. Such a population of uniform cells can be prepared by isolating a single modified cell by limiting dilution cloning followed by expanding the single cell in culture into a clonal population of cells by standard techniques.

As used herein, the phrase "transgenic cell" referred to a cell into which a nucleic acid sequence which is partially or entirely heterologous, i.e., foreign, to the cell in which it has been inserted or introduced. A transgenic cell can also be a cell into which an nucleic acid which is homologous to an endogenous gene of the cell has been inserted. In this case, however, the homologous nucleic acid is designed to be inserted, or is inserted, into the cell's genome in such a way as to alter the genome of the cell into which it is inserted. For example, the homologous nucleic acid is inserted at a location which differs from that of the natural gene or the insertion of the homologous nucleic acid results in a knockout of a particular phenotype. The nucleic acid inserted into the cells can include one or more transcriptional regulatory sequences and any other nucleic acid, such as an intron, that may be necessary for optimal expression of a selected nucleic acid.

In yet another aspect of the present invention, the subject micro-organ cultures may be used to aid in the diagnosis and treatment of malignancies and diseases. For example, a biopsy of an organ (e.g. skin, kidney, liver, etc.) may be taken from a patient suspected of having a hyperproliferative or neoproliferative disorder. If the biopsy explant is cultured according to the present method, proliferative cells of the explant will be clonally expanded during culturing. This will increase the chances of detecting such disorders, and, therefore, increase the accuracy of the diagnosis. Moreover, the patient's micro-organ culture could be used in vitro to screen cytotoxic and/or pharmaceutical compounds in order to identify those that are most efficacious; i.e. those that kill malignant or diseased cells, yet spare the normal cells. These agents could then be used to therapeutically treat the patient.

A further aspect of the invention pertains to a method of using the subject micro-organ cultures to screen a wide variety of compounds, such as cytotoxic compounds growth/regulatory factors, pharmaceutical agents, etc. For example, the need for thorough testing of chemicals of potentially toxic nature is generally recognized and the need to develop sensitive and reproducible short-term in vitro assays for the evaluation of drugs, cosmetics, food additives and pesticides is apparent. The micro-organ cultures described herein permits the use of a tissue-equivalent as an assay substrate and offers the advantages of normal cell interactions in a system that closely resembles the in vivo state.

To this end, the cultures are maintained in vitro and exposed to the compound to be tested. The activity of a cytotoxic compound can be measured by its ability to modulate the phenotype (including killing) of cells in the explant. This may readily be assessed by vital staining techniques, expression of markers, etc. For instance, the effect of growth/regulatory factors may be assessed by analyzing the cellular content of the culture, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the present system may be assessed. For example, drugs that decrease proliferation of psoriatic tissue can be identified.

In an exemplary embodiment of this method, derived for detecting agents which stimulate proliferation of a cell in the explant, the method includes isolating a tissue explant from a subject, wherein the population of cells of the explant retains a microarchitecture of the organ or tissue from which the explant was isolated, e.g., the explant is characterized by Aleph of at least about $1.5 \text{ mm}^{-1}$, and includes at least one cell which has the ability to proliferate. The explant is cultured and contacted with a candidate compound. The level of cell proliferation in the presence of the candidate compound is then measured and compared with the level of cell proliferation in the absence of the candidate compound. A statistically significant increase in the level of cell proliferation in the presence of the candidate compound is indicative of a cell proliferative agent.

The phrase "candidate compound" or "candidate agent" as used herein refers to an agent which is tested or to be tested for proliferative, anti-proliferative, differentiating, anti-differentiating, or anti-viral activity. Such agents can be, for example, small organic molecules, biological extracts, and recombinant products or compositions.

Methods of measuring cell proliferation are well known in the art and most commonly include determining DNA synthesis characteristic of cell replication. There are numerous methods in the art for measuring DNA synthesis, any of which may be used according to the invention. In one embodiment of the invention, DNA synthesis has been determined using a radioactive label ( 3H-thymidine) or labeled nucleotide analogues (BrdU) for detection by immunofluorescence.

Yet another embodiment provides a method for identifying an inhibitor of cell proliferation. This method includes providing a tissue explant as above, contacting that explant with a candidate compound, and measuring the level of cell proliferation in the presence of the candidate compound. A statistically significant decrease in the level of cell proliferation in the presence of the candidate compound is indicative of an inhibitor of cell proliferation.

In an illustrative embodiment, both potentiators and inhibitors of cell proliferation (also referred to herein as anti-proliferative agents) can be used, for example to control hair growth depending on the desired effect.

The growth of hard keratin fibers such as wool and hair is dependent on the proliferation of dermal sheath cells. Hair follicle stem cells of the sheath are highly active, and give rise to hair fibers through rapid proliferation and complex differentiation. The hair cycle involves three distinct phases: anagen (growing), catagen (regressing), and telogen (resting). The epidermal stem cells of the hair follicle are activated by dermal papilla during late telogen. This is termed "bulge activation". Moreover, such stem cells are thought to be pluripotent stem cells, giving rise not only to hair and hair follicle structures, but also the sebaceous gland and epidermis. Cell proliferative agents and inhibitors of cell proliferation provide means for altering the dynamics of the hair growth cycle to, for example, induce quiescence of proliferation of hair follicle cells, particularly stem cells of the hair follicle.

Inhibitors of hair follicle cell proliferation can be employed as a way of reducing the growth of human hair as opposed to its convention removal by cutting, shaving, or depilation. For example, inhibitors of hair follicle cells identified using the method of the present invention can be used in the treatment of trichosis characterized by abnormally rapid or dense growth of hair, e.g., hypertrichosis. In an illustrative embodiment, such inhibitors can be used to manage hirsutism, a disorder marked by abnormal hairiness. Use of such inhibitors can also provide a process for extending the duration of depilation.

Inhibitors of hair follicle cell proliferation can also be used to protect hair follicle cells from cytotoxic agents which require progression into S-phase of the cell-cycle for efficacy, e.g. radiation-induced death. Treatment with such inhibitors provides protection by causing the hair follicle cells to become quiescent, e.g., by inhibiting the cells from entering S phase, and thereby preventing the follicle cells from undergoing mitotic catastrophe or programmed cell death. For example, inhibitors of hair follicle cell proliferation can be used for patients undergoing chemo- or radiation-therapies which ordinarily result in hair loss. By inhibiting cell-cycle progression during such therapies, the inhibitor treatment can protect hair follicle cells from death which might otherwise result from activation of cell death programs. After the therapy has concluded, inhibitor treatment can also be removed with concomitant relief of the inhibition of follicle cell proliferation.

However, in order to start characterizing the molecular mechanisms underlying hair growth control, as well as to test potential hair affecting drugs, appropriate in vitro models for hair growth are required. In one aspect of the present invention, the subject method is used to generate hair follicle micro-organ explants which retain the microarchitecture of the follicle, e.g., the interaction between the hair follicle epithelial layer and stromal components (the dermal papilla) of the hair follicle, e.g., one or more of the stem cells, outer root sheath cells, matrix cells, and inner root sheath cells. As demonstrated in the appended examples, hair growth can be observed in these micro-organ cultures even in the absence of serum, e.g., in a minimal media. Importantly, the present invention also provides a hair follicle culture which provide the hair follicles in a substantially telogenic phase, e.g., resting. As demonstrated below, the telogenic hair follicle explants can be activated in the in vitro culture to growing anagen follicles, and in a certain embodiment, in a synchronized manner. The early transient proliferation of the epidermal stem cells of the follicle provide a unique opportunity to understand the activation of anagenic phase as mediated, for example, by paracrine and/or autocrine factors produced by the various tissues of the hair follicle organ.

Figure 17:
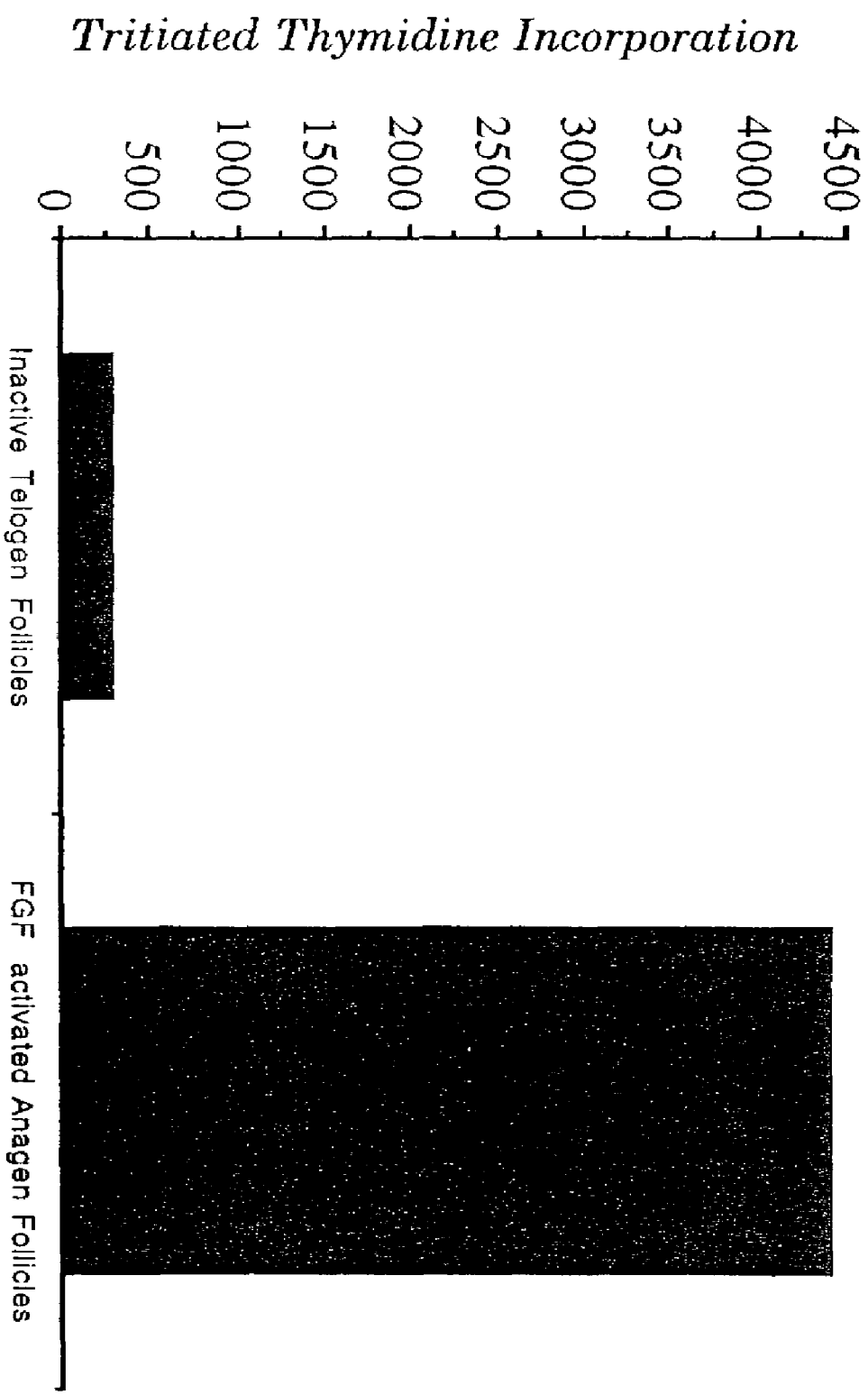
FIG. 17 is a graphic representation of the activation of telogen follicles upon treatment with FGF in micro-organ cultures of the present invention.

Moreover, the subject micro-organ cultures supply a system for identifying agents which modulate the activation or inactivation of the hair follicles, e.g., to identify agents which can either promote or inhibit hair growth. In one embodiment, telogenic (resting) hair follicle explants, such as described in Example XVIII below, are contacted with various test agents, and the level of stimulation of the hair follicles is detected. For example, transition of the hair follicle stem cells from telogen to anagen can be monitored by observing the mitotic index of the cells of the follicle, or some other similar method of detecting proliferation. To illustrate, FIG. 17 shows that thymidine incorporation can be used to measure the relative levels of stem cell activation in the explant in the absence or presence of the test compound (FGF in the figure) with increased proliferation indicative of a test agent having hair growth promoting activity.

In the reverse assay, anagenic micro-organ explants are provided in culture, e.g., such as the activated Sencar explants described in the appended examples, or growth factor stimulated explants (e.g., FGF stimulated). Test agents which inhibit proliferation of the hair follicle stem cells, e.g., relative to the untreated anagen explants, could be considered further for use as telogenic agents that prevent hair growth.

In still other embodiments, inhibitors of cell proliferation identified by the subject assay can be employed to inhibit growth of neoplastic or hyperplastic cells, e.g., tumor formation and growth. A preferred embodiment of the invention is directed to inhibition of epithelial tumor formation and growth. For a detailed description of skin epithelial tumor formation, see U.S. patent application Ser. No. 08/385,185, filed Feb. 7, 1995. Tumor formation arises as a consequences of alterations in the control of cell proliferation and disorders in the interactions between cells and their surroundings that result in invasion and metastasis. A breakdown in the relationship between increase in cell number resulting from cell division and withdrawal from the cell cycle due to differentiation or cell death lead to disturbances in the control of cell proliferation. In normal tissues, homeostasis is maintained by ensuring that as each stem cell divides only one of the two daughters remains in the stem cell compartment, while the other is committed to a pathway of differentiation (Cairns, J.(1975)Nature 255: 197-200). The control of cell multiplication will therefore be the consequence of signals affecting these processes. These signals may be either positive or negative, and the acquisition of tumorigencity results from genetic changes that affect these control points.

Figure 12:
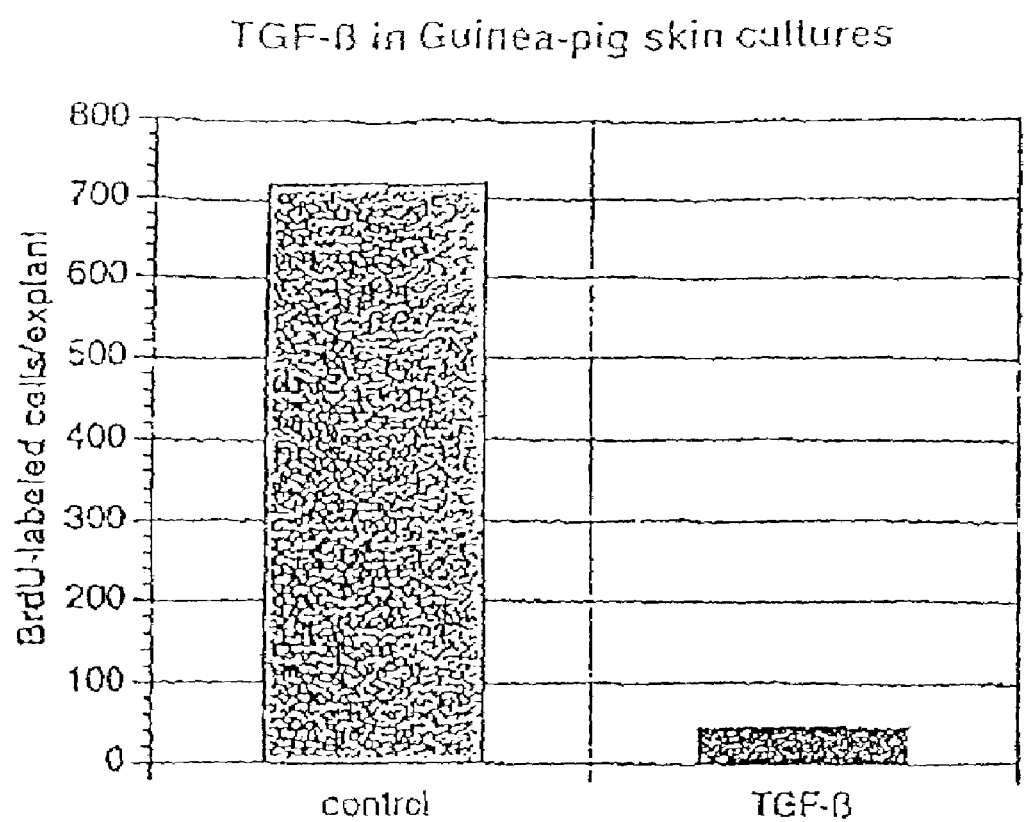
FIG. 12 is a histogram showing the inhibition of mitogenesis in micro-organ cultures in the presence of 2.5 ng/ml TGF-β in guinea-pig skin cultures.

As described in Example IX and illustrated in FIG. 12, skin micro-organ cultures of the present invention have been used for identifying cell proliferative agents and inhibitors of cell proliferation. As described in Example IX, TGF-β was tested and found to act as an inhibitor of cell proliferation. Activin, a protein which is a member of the TGF-β superfamily, has also been shown to inhibit proliferation of epidermal cells. These results indicate there may be other members of the TGF-β family that play a role in inhibition of proliferation of epithelial cells. The data suggests a role for proteins in the TGF-β family as significant regulators of epidermal homeostasis and in inhibiting epithelial tumor formation and growth in vivo.

Another aspect of the present invention pertains to a method for identifying a cell differentiating agent, i.e., a compound which causes cell differentiation. This method includes isolating a population of cells from a subject wherein the population of cells having a microarchitecture of an organ or tissue from which the cells are isolated, a surface area to volume index of at least about $1.5 \text{ mm}^{-1}$, and includes at least one cell which has the ability to differentiate. The cells are then placed in culture for at least about twenty-four hours and contacted with a candidate compound. The level of cell differentiation in the presence of the candidate compound is then measured and compared with the level of cell differentiation in the absence of the candidate compound. A statistically significant increase in the level of cell differentiation in the presence of the candidate compound is indicative of a cell differentiating agent. Differentiation, as used herein, refers to cells which have acquired morphologies and/or functions different from and/or in addition to those that the cells originally possessed. Typically, these morphologies and functions are characteristic of mature cells. The differentiation of populations of cells of the present invention can be monitored by measuring production and/or secretion of specialized cell products.

In similar fashion, the present invention also pertains to a method for identifying an inhibitor of cell differentiation. Following the same protocol as above, the level of cell differentiation in the presence of the candidate compound is measured and compared with the level of cell differentiation in the absence of the candidate compound. A statistically significant decrease in the level of cell differentiation in the presence of the candidate compound is indicative of an inhibitor of cell differentiation.

In yet another embodiment, the subject cultures permit the generation of in vitro models for viral infection. For example, epidermal or squamous tissue can be isolated, and infected with such viruses as herpes viruses, e.g., herpes simplex virus 1, herpes simplex virus 2; varicella-zoster virus; or human papilloma viruses, e.g., any of human papilloma viruses 1-58, e.g., HPV-6 or HPV-8. Similarly, hepatic models can be provided for hepatitis infection, e.g., an explant infected with hepatitis viruses, e.g., hepatitis A virus, hepatitis B virus, or hepatitis C virus. The virally-infected tissue explants can be used to identify inhibitors of viral infectivity by method of the present invention. As above, the particular micro-organ culture is provided, and contacted (optionally) with a virus which infects the cells to produce a population of virus-infected cells. The virus-infected cells can then be contacted with a candidate compound and the level of infectivity of the virus in the presence of the candidate compound measured. The measured level of viral infectivity in the presence of the candidate compound is then compared to the level of viral infectivity in the absence of the candidate compound. A statistically significant decrease in the level of infectivity of the virus in the presence of the candidate compound is indicative of an inhibitor of viral infectivity.

Methods of measuring viral infectivity are known in the art and vary depending on the type of virus used. For example, one method which can be used to measure the level of viral infectivity is by measuring the level of production in the infected cells of the micro-organ culture or in the micro-organ culture medium of gene products specific for the particular virus being tested. For example, to measure the level of infectivity of hepatitis virus, e.g., hepatitis B virus, of cells in a micro-organ culture, hepatitis protein production and hepatitis DNA can be quantitated. In general, micro-organ culture medium can be incubated with antibodies against a selected viral protein and the immunoreactive proteins analyzed by a variety of methods known in the art, e.g., on SDS-polyacrylamide gels, ELISA. For example, to measure production of hepatitis B surface antigen, micro-organ culture medium from micro-organs previously incubated with hepatitis B virus can be sampled at daily intervals and assayed for the surface antigen by an ELISA (Abbott) method as described by the manufacturer. This method can be modified for quantitation using serially diluted standard surface antigen (Cal-Biochem). A statistically significant decrease in the accumulation of hepatitis B surface antigen in the culture medium indicates that the candidate compound tested is an inhibitor of hepatitis virus infectivity.

In addition to measuring levels of HBsAg in the micro-organ culture medium, newly synthesized hepatitis B virus DNA from cell extracts from the micro-organ culture can be detected and quantitated by PCR amplification of the DNA, followed by Southern blot analysis using labeled primer pairs in the HBV pre-S (HBsAg encoding) region as probes (see e.g., Sambrook, J. Et al. (1989) Molecular Cloning-A Laboratory Manual, Cold Spring Harbor Laboratory, 2nd ed., vol. 2, pp. 10.14-10.15). Relative quantitation can be achieved by densitometry and confirmed by scintillation counting of corresponding bands. Reduction in levels of newly synthesized viral DNA indicate that the candidate compound tested is an inhibitor of hepatitis virus infectivity.

In another example, the gag, pol, and env protein products of retroviruses, e.g., human immunodeficiency virus (HIV), can also be measured using the above-described and other standard techniques known in the art. For example, pol protein expression in cells of micro-organ cultures infected with HIV can be measured by incubating cell extracts with anti pol antibodies or pooled AIDS patients sera and immunoreactive proteins analyzed on SDS/polyacrylamide gels. To measure infectivity of herpes virus, e.g., epstein/barr virus (EBV), in the micro-organ cultures of the present invention, EBV DNA and EBV induced nuclear antigen production can be analyzed using the methods described herein.

The micro-organ cultures of the present invention can also be used to promote wound healing in a subject. Thus, the present invention further pertains to a method for promoting wound healing in a recipient subject. This method includes isolating, from a donor subject, a population of cells having a surface area to volume index is at least approximately 1.5 $mm^{-1}$. Typically, the population of cells is placed in culture for at least about twenty-four hours. The population of cells can then be applied to a wound of the recipient subject. In one embodiment, the wound or lesion, is slow-healing or chronic, e.g., a wound associated with diabetes, e.g., a burn, e.g., an ulcer. As demonstrated in Examples X and XI, skin micro-organ cultures of the present invention can be used as micro-explants to be applied to chronic wounds (Example X) and can form a viable implant capable of growing hair (Example XI).

In still another embodiment, the subject micro-organ explants are provided in an assay to test for cytotoxicity or for irritation. In an exemplary embodiment, the subject method provides a technique for in vitro testing of ocular and dermal irritants. The process, much like above, involves the topical application of liquid, solid granular or gel-like materials (e.g., cosmetics) to the micro-organ cultures of the present invention, followed by detection of the effects produced in the culture.

Currently, potential eye and skin irritation of many chemicals, household cleaning products, cosmetics, paints and other materials are evaluated through direct application to animals or human subjects. However, as is appreciated by most in the industry, such approaches are not met with overwhelming public support. The present method provides an alternative assay which does not require sacrifice or permanent maiming of an animal and also provides data in an objective format. In an illustrative embodiment, skin micro-organ cultures are derived according to the present invention. The cultured explants are contacted with a test agent, such as a cosmetic preparation, and the cell viability is assessed at some time after the exposure. In a preferred embodiment, an MTT assay (based on the reduction of a tetrazolium dye by functional mitochondria) is used to score for viability.

The micro-organ cultures of the present application can additionally be used to identify factors involved in normal homeostasis of tissues and cells, study the effect on the normal homeostatis of tissues and cells of changes in the environment of the cells including changes in nutrients and the presence of potentially toxic agents, study the pathway of changes in the tissues and cells that are triggered at the beginning and during pathogenesis or trauma; identify repair mechanisms that reverse the adverse effects in an altered environment associated with pathogenesis or trauma; study developmental regulation of cells that differentiate during the normal homeostasis of the tissue and developmental regulation of specialized structures (e.g., hair follicles) within the tissue; and for organ supplementation where pieces of an individual's organ remain but are insufficient for replacing or regenerating damaged tissue such as occurs in patients which chronic skin ulcers, which have healing deficiencies caused by inappropriate blood supply, or where the local skin is unable to heal such as in the conditions known as type I or type II diabetes.

EXEMPLIFICATION

The invention now being generally described, it will be more readily understood by reference to the following examples which are included merely for purposes of illustration of certain aspects and embodiments of the present invention, and are not intended to limit the invention.

Micro-organ cultures from animals including adult human skin, mouse, guinea pig and rat skin have been isolated and grown for up to 21 days in culture. However, it is within the scope of the invention to maintain cultures periods of time beyond 21 days.

Furthermore, it is within the scope of the invention to form micro-organ cultures from a wide range of animals. The range of animals is merely exemplified but is not limited to the samples provided below.

As described in the appended examples, micro-organ cultures were prepared from skin and also from organs including the mammalian pancreas, liver, kidney, duodenum, esophagus and bladder. Similarly, micro-organ cultures of epithelia from mammalian cornea, kidney, breast tissue and various gut derived tissues in addition to the esophagus such as intestine and colon may also be prepared using the methods of the invention. Indeed, it is within the scope of the invention to isolate and maintain micro-organ cultures from any site which contains an epithelial/stromal architecture within the body.

The above notwithstanding, the subject micro-organ culture technique has been used to preserve tissue explants in long-term culture from tissue not having epithelial/stromal architecture, such as certain lymphoid tissue, e.g., thymus and spleen explants.

Example I

Preparation of Micro-Organ Cultures of Epidermis

Fresh skin was obtained after surgery, cleaned from underlying fat tissue and cut into 0.4×5 cm flaps, which are then transversely sectioned, using a tissue chopper or other suitable cutting means into 300μm sections under sterile conditions so that the final tissue segments had dimensions of 4 mm in width and 0.3 mm in thickness (see FIG. 1). These micrograms were placed in a 24-well microplate in 400 μl of DMEM in the absence of serum under 5% $CO_2$ at 37° C., under constant shaking at 12 rpm for periods of one to eight days. Twenty micro-explants were grown per well.

Example II

Measurement of the Proliferation of Mouse, Guinea Pig and Human Epidermal Micro-Organ Cultures Micro-organ cultures were prepared according to Example I and proliferation of the cells was measured by analyzing the amount of DNA synthesis as follows. Mouse skin and guinea pig skin were grown for two days and human skin grown for four days after which BrdU was added to the medium at a final concentration of 100 μM for three hours, followed by fixation of the cells in 4% formaldehyde. After fixation, the cultures were stained with goat anti-BrdU antibodies followed by anti-goat-FICT labeled IgG. Histological preparations were embedded in following fixation in 4% formaldehyde and cut into 3 μm slices and stained with methylene blue.

It was found that the fraction of cells synthesizing DNA in vitro after two to four days in culture increased up to 10 fold compared with the values observed in vivo, after which the rate of DNA synthesis gradually decreased but remained high for up to 10 days in culture(see FIGS. 2, 3 and 4A-4D). Even at six days in culture, the cells maintained a steady state of proliferation and differentiation so that the tissue architecture was preserved (FIGS. 5A-5C).

Example III

Proliferation of Cells in Micro-Organ Cultures of Various Sizes

Guinea pig micro-organs were prepared as in Example I. Whole thickness skin strips 4 mm in width were sectioned into explants of varying thickness including slices of 300, 450, 600, 700, 900, 1200 and 3000 μm thickness. These slices were placed individually into wells containing serum free medium for two days. BrdU was added for four hours before termination at a final concentration of 100 μM. The explants were then fixed in 4% formaldehyde and stained with goat antibodies to BrdU followed by an anti-goat IgG FITC labeled secondary antibody preparation. The results of this experiment are illustrated in FIG. 6. The amount of BrdU incorporation as a function of the number of cells/unit tissue is significantly reduced as the thickness of the explants increases.

Example IV

Preparation of Pancreatic Micro-Organ Cultures and Measurement of Cell Proliferation Guinea-pig pancreas was removed and then cut into sections of 300 μm in thickness, 4 mm in width and 2 mm in depth using an appropriate tissue chopper and in such a way that the pancreas microarchitecture was maintained. The micro-explants were grown in culture for several time periods from two to eighteen days. Seven micro-organs were placed in each of 96 wells of a plate in 150 μl of serum-free DMEM under 5% $CO_2$ at 37° C. under constant shaking at 12 rpm. BrdU was added three hours before termination at a final concentration of 100 μM and the explants were then fixed in 4% formaldehyde and stained with goat antibodies to BrdU followed by anti-goat-FITC labeled IgG. FIGS. 7A-7B illustrate that cells in the pancreas-derived micro-organs were actively proliferating.

Example V

Preparation of Pancreatic Micro-Organ Cultures and

Measurement of Insulin Secretion into the Culture Medium

Adult pig pancreas micro-organ cultures were prepared as in the previous examples for skin. Pancreases were removed, cut with scissors to an approximate depth of 2 mm and sliced into sections 300 μm thick having a width of 4 mm. The micro-organ cultures were grown for 14 days in serum free medium. Every two days, the medium was removed and fresh medium added. Collected media was assayed for insulin content using standard radioimmunoassay methods.

Example VI

Transplantation of Pig Pancreatic Micro-Organs into a Xenogeneic Subject

Adult pig pancreas micro-organ cultures were prepared as in the previous examples for skin. Pancreases were removed, cut with scissors to an approximate depth of 2 mm and sliced into sections 300 μm thick having a width of 4 mm. The micro-organ cultures were then grown for different time periods of 0 to 5 days in serum-free medium, and after culturing, the pancreatic micro-organs were removed from the culture and transplanted into both the visceral and parietal mesoderm of rat hosts. The micro-organs survived for at least one month in vivo and became well vascularized. After three, five, seven and fourteen days in vivo, extensive cell proliferation could be detected. Moreover, positive insulin staining was observed in vivo after four, seven, and thirty days post transplantation.

Example VII

Figure 9:
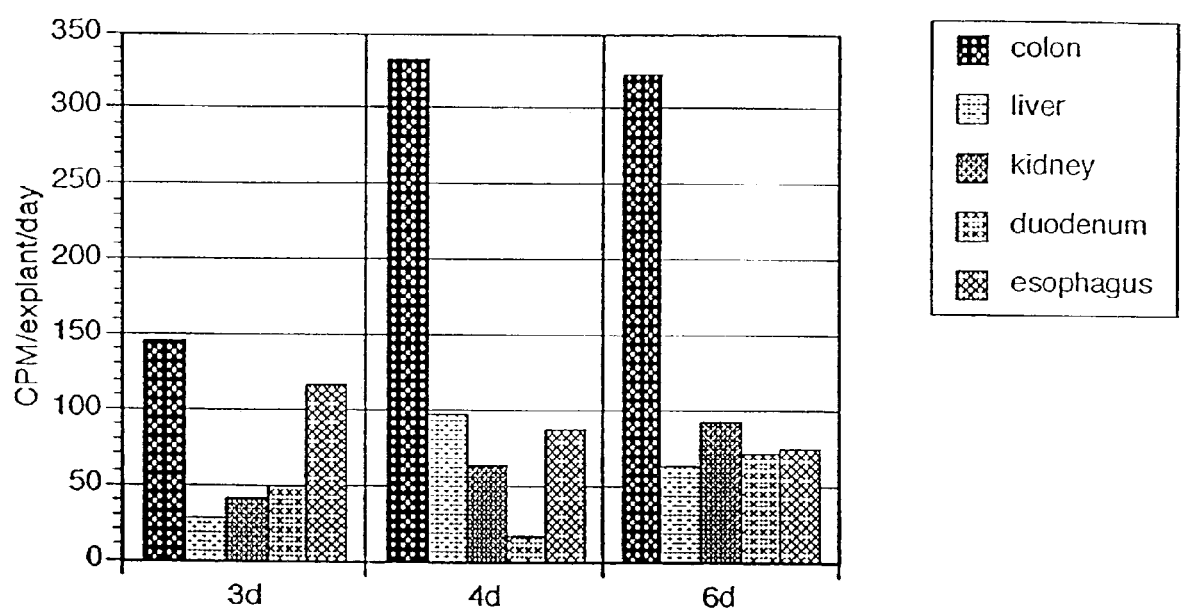
FIG. 9 is a histogram showing $^3$H-Thymidine incorporation in proliferating cells in micro-organ cultures of the colon, liver, kidney, duodenum and esophagus, at three days, four days and six days of culture.

Preparation of Liver, Kidney, Duodenum, Esophagus and Bladder Micro-Organ Cultures and Measurement of Cell Proliferation in the Micro-Organ Cultures Guinea-pig micro-organ cultures from several epithelial tissue containing organs were prepared as in previous examples for skin. Organs were removed and with scissors, were cut to an appropriate width of 2 mm, length of 3 mm, and sliced into sections of 300 µm thick. The microcultures were incubated for three, four and six days in serum-free medium. Twelve hours before termination of the experiment, $^3$H-thymidine was added to the cultures of explants. At termination, the tissue was fixed, rinsed several times and counted in a scintillation counter. The results of this experiment are illustrated in FIG. 9. As shown in FIG. 9, all tissues exhibited active proliferation which continued for six days as determined by uptake of $^3$H-thymidine.

Example VIII

Proliferation of Hair Follicles in Micro-Organ Cultures

Figure 11:
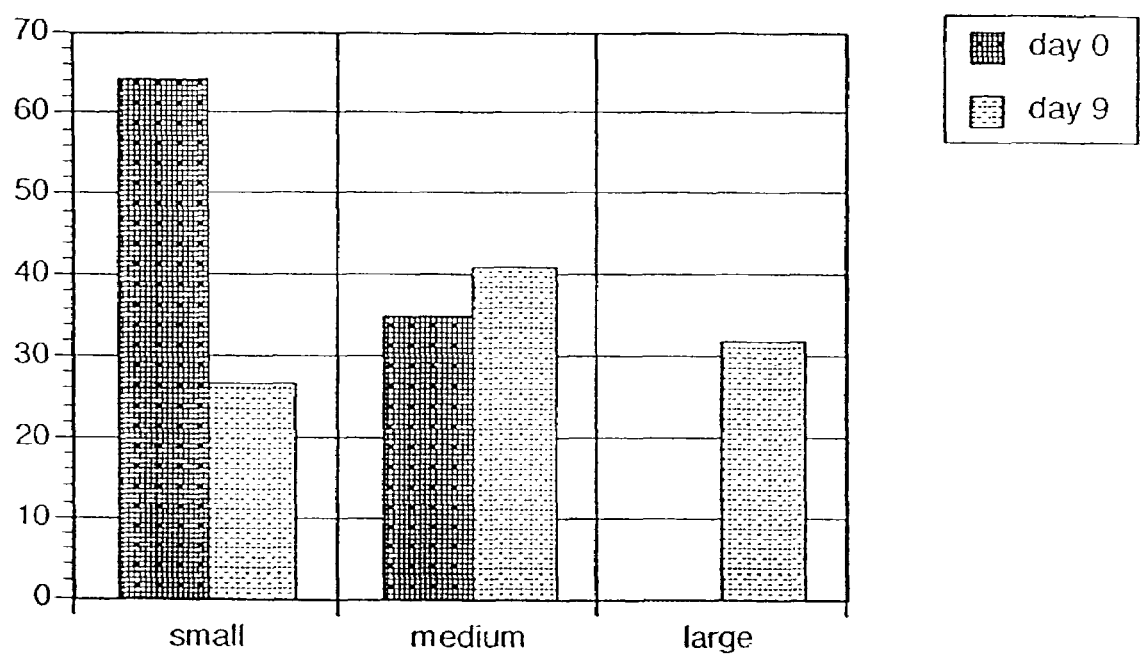
FIG. 11 is a histogram showing the size distribution of hair shafts at the beginning and end of the microculture.

Skin micro-organ cultures were prepared according to Example I and incubated for two days. BrdU was added three hours before termination of incubation. Cells were fixed in 4% formaldehyde and stained with goat anti-BrdU antibodies followed by anti-goat-FITC labeled IgG. Intact hair follicles that were present in vivo in their normal surroundings could be maintained under precisely controlled culture conditions, without the need of adding serum or any other exogenous factor. Hair follicle cells in these micro-organs were found to proliferate vigorously for several days under the conditions of the present method as indicated by the large number of hair follicles cells that incorporated BrdU (FIGS. 10A-10C). The size distribution of hair shafts at time zero of a micro-organ guinea pig culture and after two weeks is shown in FIG. 11. The medium was exchanged every two days. Hair shaft size has been arbitrarily classified as small, medium and large. After nine days in culture, there was a clear shift in size distribution so that the percentage of small hairs decreased from 64% to 28%, while large shafts which were not present at the beginning of the culture represented 30% of the shaft population.

Example IX

Preparation of Assay for Measuring the Effect of a Candidate Compound on Cell Proliferation The cultures were prepared and maintained in defined medium in similar growth conditions as described in Example I. Control samples were analyzed by immunocytochemistry to determine that the micro-organ culture was maintained in a manner that was similar to that occurring in vivo.

Duplicated samples of skin micro-cultures were treated with TGF-β at 2.5 ng/ml. A quantitative analysis of the number of BrdU labeled cells/explant was performed according to Example II. Greater than 90% inhibition of DNA synthesis was observed in the presence of TGF-β compared with controls (FIG. 12).

Example X

A Method for Promoting Healing Chronic Non-Healing Skin Ulcers

Figure 13:
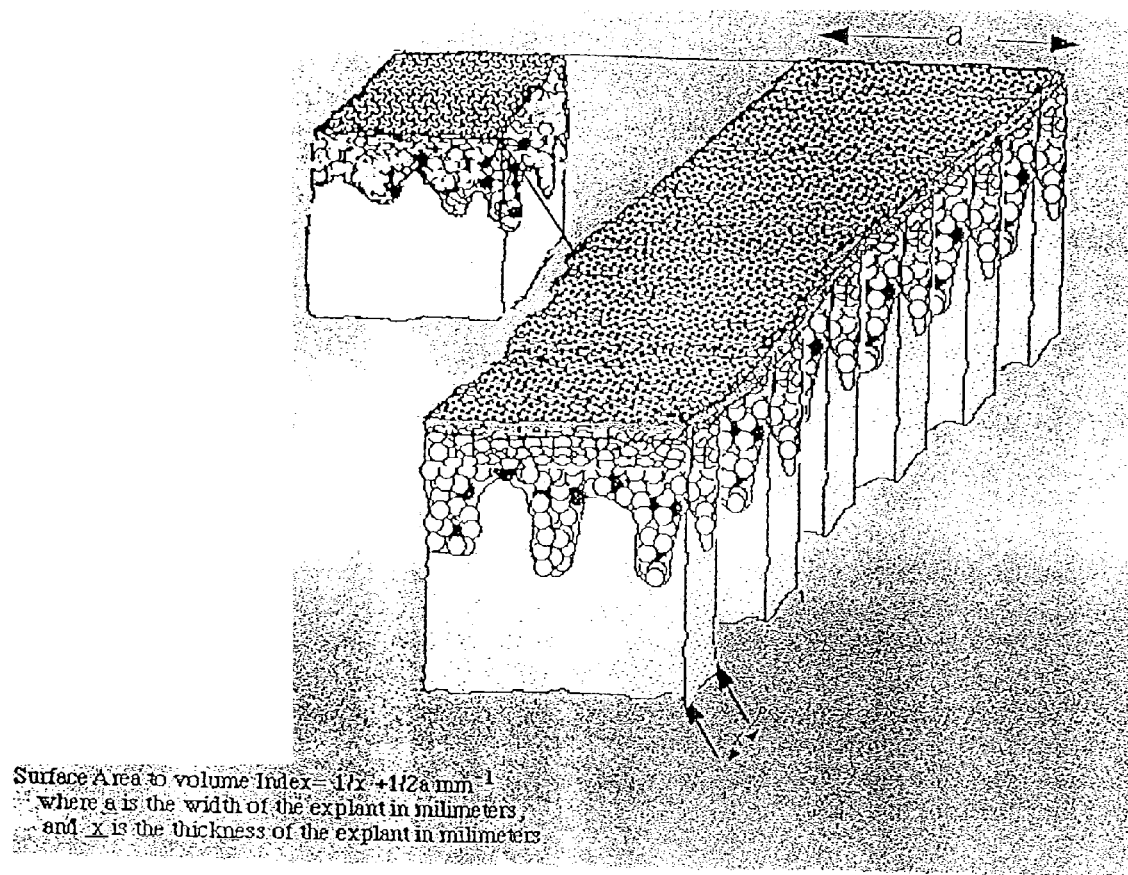
FIG. 13 is a diagrammatic representation of a micro-organ explant for treatment of chronic skin ulcers showing incomplete sectioning of tissue slices so as to maintain a structure that can be readily manipulated in vivo.

According to this method, a small-area of normal, uninvolved skin graft is removed from the patient and full thickness micro explants of 4 mm in width and 0.3 mm thick are prepared as described in Example I. The preparation however differs from Example I in that the sectioning into 0.3 mm slices is deliberately incomplete so that a series of sections are held together as indicated in FIG. 13, the upper epidermal layers including the stratum corneum. The design of this implant is directed to permitting the nutrients to reach all the cells but maintaining the tissue slices in a manipulatable format. The patient's wound is cleaned and surrounding skin edges are removed. The area devoid of skin is then carefully covered by the micro-explants, which are placed on the wound such that the non-sectioned edge is facing outward and the opposing sectioned pieces are suspended in the fluid within the wound. Sufficient micro-explants are prepared to substantially cover the wounded area. The treated region is then covered with a suitable dressing and allowed to heal.

Example XI

Proliferation of Hair Follicles in Vivo

Figure 14:
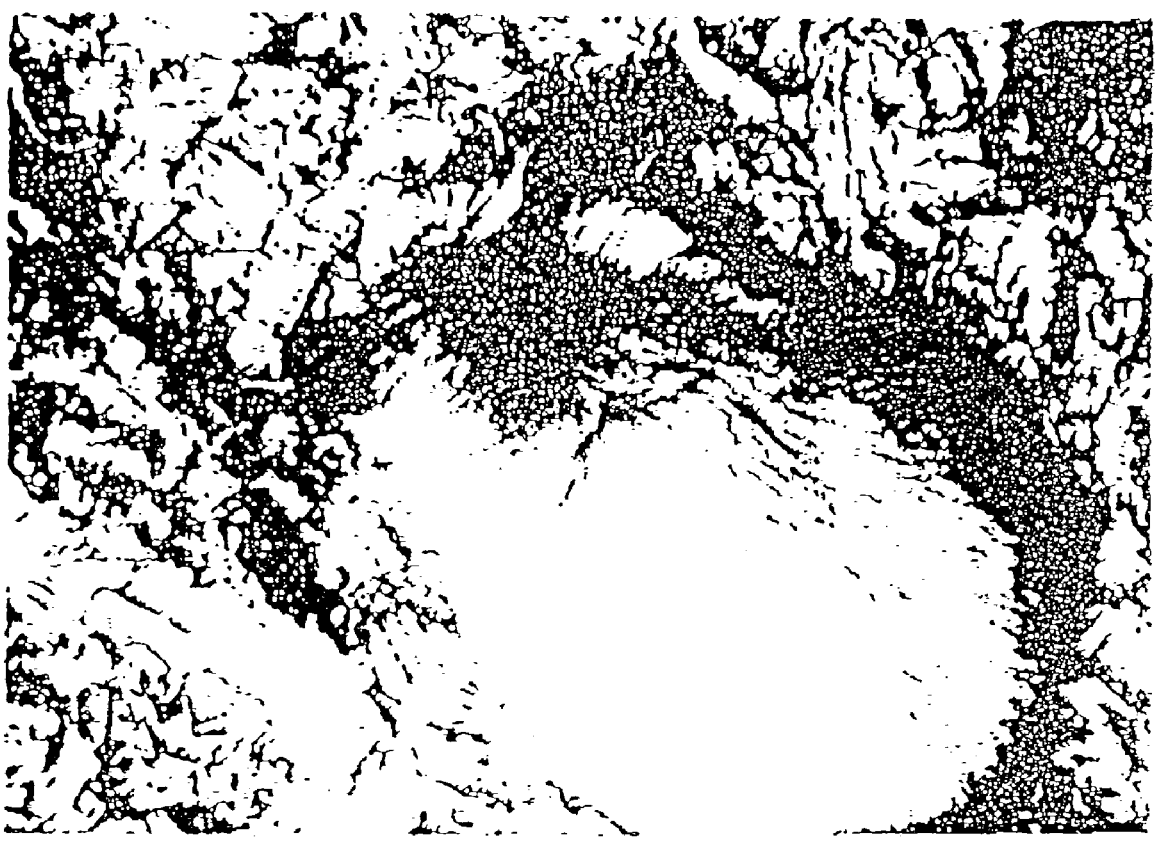
FIG. 14 is a photograph of the surface of a mouse after replacement of a piece of normal skin with a micro-organ culture; healing, generation of new hair shafts in the implant, and incorporation of the implant into the normal mouse skin can be observed (mag 10×).

An in vivo animal experiment was performed where a 1 cm$^2$ area of skin was lo removed from a mouse and incompletely microsectioned so that the stratum corneum of the whole skin area was left intact as described above. The micro-organ was reimplanted into its original position in the mouse stitched and allowed to heal. The implant remained viable, became incorporated into the animal tissue and new hair shafts grew from the implant after one to two weeks in culture. (See FIG. 14).

Example XII

Human Psoriatic Skin Micro-Organ Cultures

Split-thickness psoriatic skin from an 82 year old patient was obtained after autopsy using a dermatome. The skin was then sectioned into 0.5×5 cm flaps which were then transversely sectioned using a tissue chopper or other suitable cutting device into 300 µm sections. These micro-organ sections were placed in microplates in serum-free DMEM under 5% CO$_2$ at 37° C. under constant shaking for periods of one to fourteen days. In some instances, growth factors were added to the culture medium. The medium was changed every two days. The human psoriatic skin proliferated extensively as micro-organ culture.

Example XIII

Liver Micro-Organ Cultures Infected with Hepatitis Virus

Human, rat, mouse, and guinea pig liver was sectioned and cultured as micro-organ cultures as described in Example VII. Active proliferation in these micro-organ cultures was detected using BrdU incorporation as described herein. The hepatocytes in these micro-organ cultures were determined to be functional as measured by assay of urea (Sigma Chemical, urea detection kit) and albumin production (ELISA) after at least 14 days in culture.

Human liver micro-organ cultures prepared above were incubated with sera from patients positive for hepatitis B and hepatitis C virus. After 24 hours, the medium was removed and fresh DMEM with and without 10% normal fetal calf serum (FCS) was added. Every two days, the culture medium was exchanged with fresh medium and the conditioned medium tested for viral particles using antibodies against the viral protein HBs. A significant increase in number of viral particles was detected after 4 days in those micro-organ culture that were cultured in the presence of FCS.

Example XIV

Thymus and Spleen Micro-Organ Cultures

Mouse and rat micro-organ cultures from thymus and spleen were prepared essentially as in the previous examples for skin. Organs were removed and cut with scissors to an approximate width of 2 mm and length of 3 mm. These samples were then spliced into explants of approximately 300 µm thick using an appropriate tissue chopper in such a way as to preserve the essential microarchitecture of the organ. The micro-organs were then incubated for 1, 3, 5 and 10 days in serum free medium. Active proliferation in these micro-organ cultures was detected using BrdU incorporation as described herein.

Example XV

Bone Marrow Micro-Organ Cultures

Micro-organ cultures from bone marrow were prepared by carefully removing the bone marrow intact from femurs of rats and mice. Since the diameter of the marrow in such explants is only about 1-2 mm, the marrow was directly sliced into micro-organ explants using 300 µm thick using a tissue chopper. This method ensured the microarchitecture of the marrow was preserved while at the same time retaining a surface/volume index amenable to long-term culture. The micro-organs were incubated for 3 days in serum free medium. Active proliferation of marrow cells in these micro-organ cultures was detected using BrdU incorporation as described herein.

Example XVI

Delivery of Gene Products to Skin Micro-Organ Cultures

The high surface area to volume inherent to the micro-organ cultures of the present invention allows easy access to tissues for a variety of gene transfer techniques. In this example, micro-organ cultures are transfected with foreign genes using electroporation and lipofection. The micro-organ cultures can be transplanted into animals and survive for at least about thirty days in vivo and become vascularized. This demonstrates the feasibility of using MC cultures of tissues in ex vivo gene therapy protocols. A further advantage of the MC culture is that it can be transplanted to a defined position in the body, so that if necessary it could be readily removed in the future. This contrasts with cell suspension transplantation into the body in which the cells can migrate or become "lost" in normal tissue.

Guinea pig skin was dissected and sliced into sections with a width of 2 mm and a thickness of 300 µm. The skin was cultured as a micro-organ in serum-free Dulbecco's minimum essential media with penicillin and streptomycin at the concentrations recommended by the manufacturer. After one day in culture at 37° C. and 5% $CO_2$, the skin micro-organ cultures were rinsed with DMEM without antibiotics and added to a 0.4 cm gap disposable electroporation cuvette with 500 µl of media on ice.

Ten micrograms of the plasmid DNA containing the indicated reporter genes were added as shown (each plasmid had a cytomegalovirus promoter driving the expression of either a β- galactosidase (control) or luciferase reporter gene. The luciferase plasmid backbone was pRC-CMV (Invitrogen) fused in frame with the firefly luciferase gene.

Figure 15:
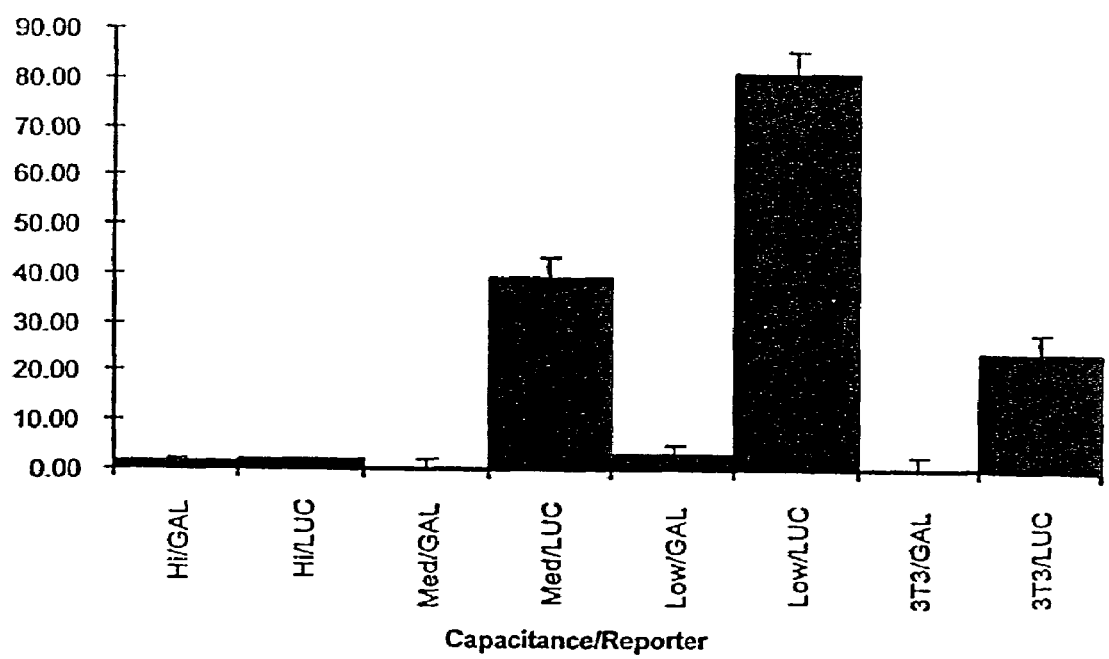
FIG. 15 is a graphic representation of the expression of a luciferase reporter gene in a guinea pig skin micro-organ culture after transfection ( of the culture with a plasmid encoding the luciferase reporter gene.

The samples were electroporated at 220 mV and the capacitance varied as shown in FIG. 15 (Hi=900 µF, medium=500 µF, low=250 µF). NIH3T3 cells were treated at 250 µF) with a Bio-Rad electroporation device. The samples were then further incubated with DMEM containing 10% bovine calf serum, penicillin, streptomycin, and glutamic acid for 2 days in a 24 well culture plate. The media was removed, and the samples were suspended in about 700 µl of cell culture lysis reagent (Promega). The tissue pieces were homogenized, and then 20 µl was added to 100 µl of luciferase assay reagent (Promega), and luminescence was detected in triplicate with the Packard TopCount. As a positive control, NIH3T3 cells from a 75 cm culture flask were trypsinized, and treated identically to the micro-organ cultures. As illustrated in FIG. 15, at the medium (500 µF) and low (250 µF) capacitance settings, significant luciferase activity was detected. For comparison, similar amount of NIH3T3 immortal cultured cells were electroporated with the same plasmids at 250 µF.

Figure 18:
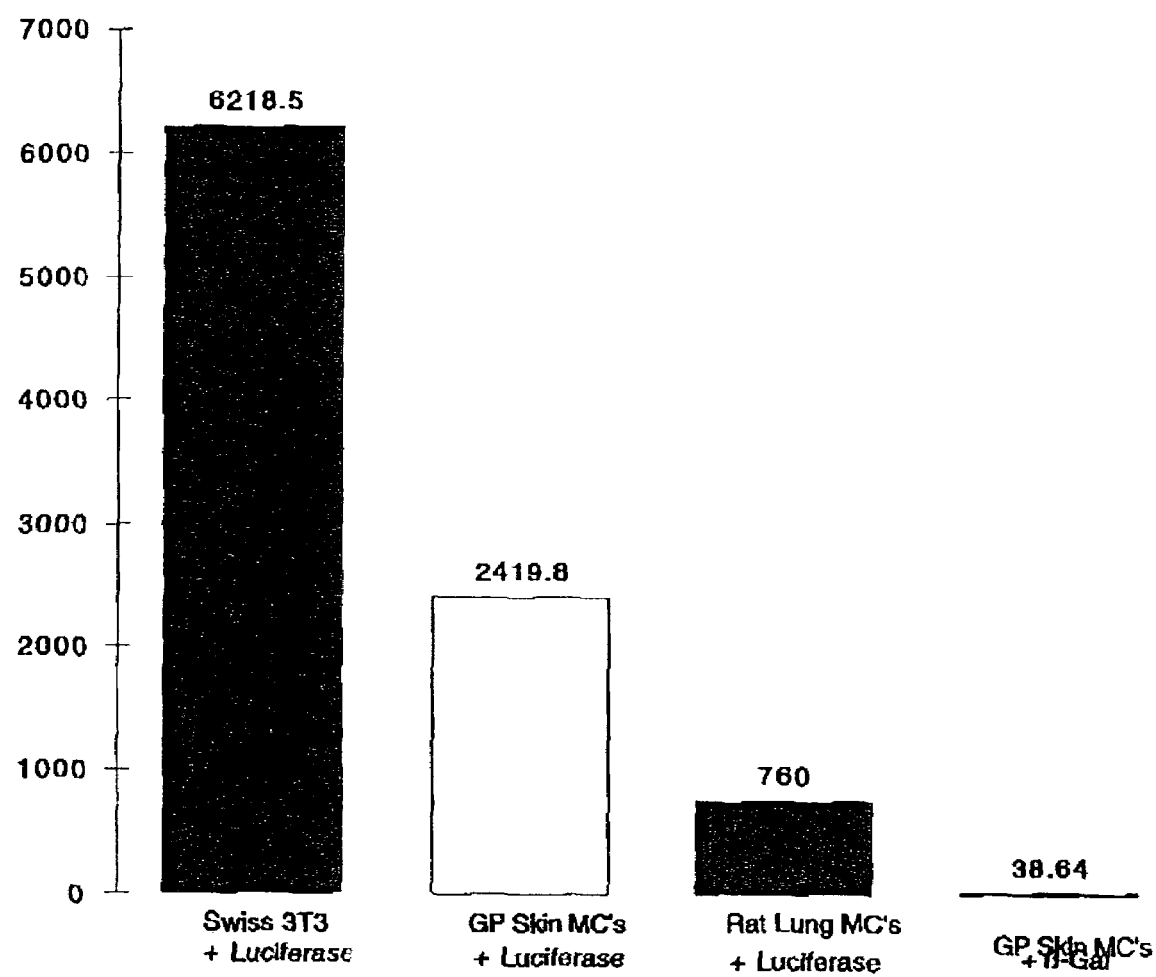
FIG. 18 is a graphic representation of the expression of a transgenic luciferase gene in micro-organ explants of the present invention.

In another experiment, the transfection of the micro-organ explants was accomplished by lipofection, which was observed to be more efficient than electroporation. In particular, micro-organ cultures from guinea pig skin, newborn mouse skin, and rat lung were transfected with a plasmid containing a luciferase reporter. Briefly, the micro-organ cultures were grown at 37° C. in 5.5% $CO_2$ in DMEN with 1% penicillin/streptomycin and 1% L-glutamine for one day before transfection. The explants were plated on 24 well plates with 20 explants and 400 µl of media per well. For transfection, the micro-organ cultures were rinsed twice with Optimem, and 10 µl of Lipofectin (Gibco BRL)+2 µg of DNA+Optimem was added to each well with the final volume being 500 µl. The Optimem/Lipofectin/DNA solution was made according to the Lipofectin manufacturer's directions. The cultures were then incubated for 5-6 hours at 37° C. in 5.5% $CO_2$. The Optimem/Lipofectin/DNA media was then replaced with 400 µl of DMEN with 1% penicillin/streptomycin, 1% L-glutamine and 10% FCS, and the cultures incubated overnight at 37° C. in 5.5% $CO_2$. The following morning, the micro-organ cultures were removed, washed twice with 1X PBS, and ground in a hand-operated glass tissue grinder in 750 µl of 1X cell culture lysis buffer (Promega). Luciferase activity from the transgene was detected using Luciferase Assay System (Promega), with the results reported in FIG. 18.

Example XVII

Delivery of Gene Products to Micro-Organ Cultures

Figure 16:
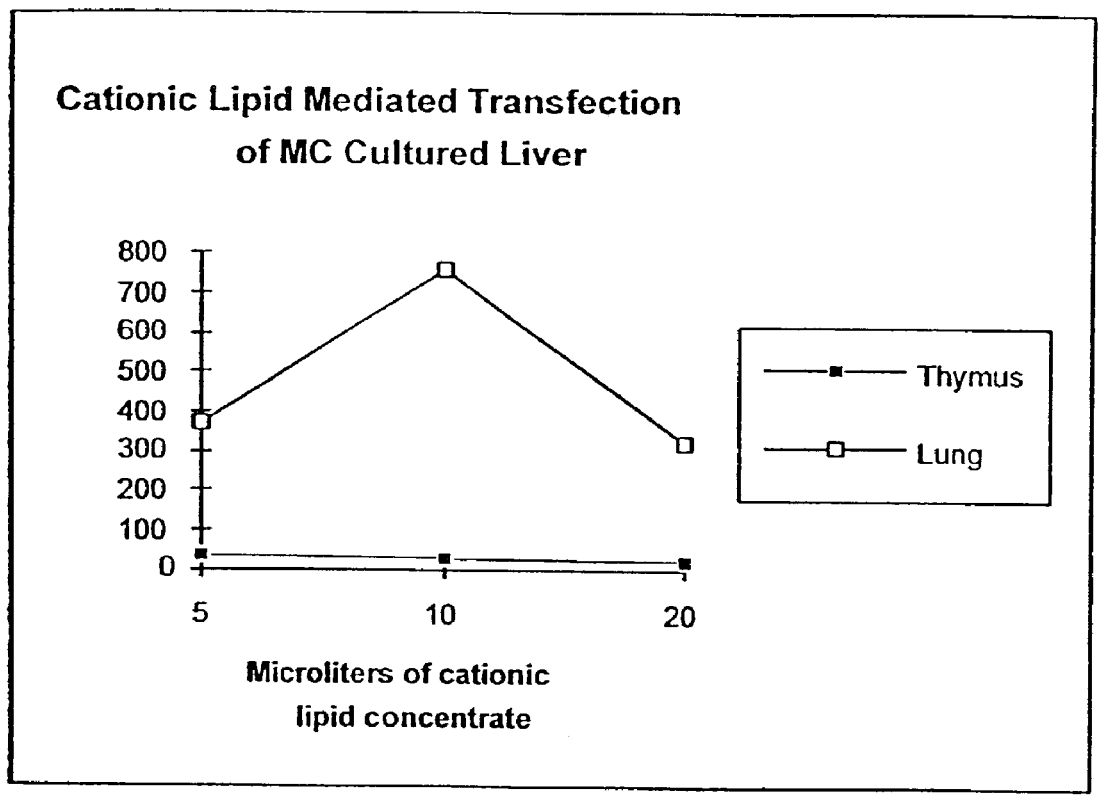
FIG. 16 is a graphic representation of the expression of a luciferase gene in rat lung and thymus micro-organ cultures after cationic lipid mediated transfection of the culture with plasmid encoding the luciferase reporter gene.

Lung and thymus from an eight week old female Lewis rat were dissected and processed for micro-organ culturing as described in Example XV. The micro-organ cultures were placed in culture wells and transfected with cationic lipid/luciferase encoding plasmid DNA complexes for five to six hours while incubating at 37° C. The cationic lipid/plasmid DNA solution was aspirated, and the cultures were then incubated in medium plus 10% serum for two days, and then assayed for luciferase reporter gene expression (expressed in arbitrary light units). The results of this experiment are illustrated in FIG. 16. As demonstrated in FIG. 16, the lung, but not the thymus expresses the transfected luciferase gene under these conditions. As expected, the negative control β-galactosidase transfected lung micro-organ culture (10 μl cationic lipid concentrate) was near machine background for light production (23 light units).

Example XVIII

Hair Shaft Growth in vitro

New born mouse skin was obtained after surgery, cleaned of underlying fat tissue and cut into 0.4×5 cm flaps, which were then transversely sectioned, using a tissue chopper or other suitable cutting devise into 300 μm sections. The micro-organs were placed in microplates in DMEM in the absence of serum under 5% $CO_2$ at 37° C. under constant shaking for periods of 1 to 14 days. Certain of the micro-organ explants were contacted with a growth factor, e.g., FGF, which was added to the culture media. The medium was changed every 2 days.

New born "hairless" skin can be induced to produce hair shafts when grown in MC cultures. Micrographs of skin from 30 hr-old mouse, grown in micro-organ cultures for 3 days in the presence of 1 ng/ml EGF indicated the development of hair shafts in the explants, which growths were not present at the beginning of the culture period.

In another set of experiments, activation of telogen follicles was observed. The Sencar mouse provides a useful model to study hair follicle activation because the follicles are well synchronized and the cycle stages have been well characterized. Sencar mice provide an in vivo model for anagen activation. The removal of the club from a telogen follicle can induce new hair formation, the first signs of which, are well characterized. Skin from adult Sencar mice was obtained after surgery, cleaned from underlying fat tissue and cut into 0.4×5 cm flaps, which were then transversely sectioned, using a tissue chopper or other suitable cutting device into 300 μm sections. The micro-organs were placed in microplates in DMEM in the absence of serum 5% $CO_2$ at 37° C. under constant shaking for periods of 1 to 14 days. Activation of telogenic follicles, whether induced by club removal or growth factor treatment, was manifested by the proliferation of follicle stem cells. FIG. 17 illustrates the activation of a telogenic explant, as detected by thymidine incorporation.

Example IXX

Preparation of Pancreatic Islets for Transplantation

Several techniques have been developed to prepare islet cells from various mammalian sources, in large quantities since they constitute a potentially transplantable beta cell mass with which to treat established type 1 diabetes. Two main drawbacks have been encountered so far. It has proven difficult to obtain a reproducible reliable way of preparing beta cells. Second, the viability of these cells both in vitro and in vivo is largely variable . In part due to the first reason and in part due to the fact that the β-cells most likely require support from the stroma that underlies the islets in the normal pancreas. Attempts of course at maintaining pancreatic organs ex vivo have so far been unsuccessful. Using the MC culture technology described herein, success has been achieved for establishing micro-organ cultures of mouse, rat, guinea pig and pig pancreas in vitro in defined culture medium Pancreas micro-organ cultures have now been grown in vitro for periods of up to one month. Within the cultures, explants maintain their tissue microarchitecture and certain cell subpopulations proliferate actively as determined by BrdU incorporation and labeling. Furthermore the islet cells secrete insulin into the medium even after one month of in vitro culture.

Transplantation experiments have been performed in which pig micro-organ pancreas cultures have been implanted into both the visceral and parietal mesoderm of rat hosts. Explants have been kept for periods varying from a few days up to one month in vivo. The explants become well vascularized and incorporate into the tissue host.

Example XX

Preparation of Human Psoriatic Skin Micro-Organ Cultures

Split-thickness psoriatic skin from a patient was obtained after autopsy, using a dermatome. The skin was cut into 0.4×5 cm flaps, which were then transversely sectioned with a tissue chopper into 300 μm thick sections. These micro-organ explants were cultured in DMEM (no serum) in microplates at 37° C. and 5% $CO_2$ for periods of 1 to 14 days. Inspection of the micro-organ explants at various time points indicated that the cells of the explant had remained viable, and proliferation was occurring.

All of the above-cited references and publications are hereby incorporated by reference.

EQUIVALENTS

Those skilled in the art will recognize, or be able to ascertain using no more than routine experimentation, numerous equivalents to the specific assay and reagents described herein. Such equivalents are considered to be within the scope of this invention and are covered by the following claims.

What is claimed is:

1. A method of delivering a gene product to a recipient, said method comprising the steps of: (a) providing a micro-organ explant expressing at least one recombinant gene product, said micro-organ explant comprising a population of cells, said micro-organ explant maintaining a microarchitecture and a three dimensional structure of an organ from which it is obtained and at the same time having dimensions selected so as to allow diffusion of adequate nutrients and gases to cells in said micro-organ explant and diffusion of cellular waste out of said micro-organ explant so as to minimize cellular toxicity and concomitant death due to insufficient nutrition and accumulation of the waste in said micro-organ explant, at least some of the cells of said population of cells of said micro-organ explant expressing at least one recombinant gene product, wherein said organ is skin and said explant has a surface area to volume index characterized by the formula $1/x + 1/a \geq 1.5$ mm$^{-1}$, wherein "x" is tissue section thickness and "a" is tissue section width in millimeters; and (b) implanting said micro-organ explant in an allogeneic or autologous recipient wherein step (a) is effected by: (i) isolating said micro-organ explant from a donor; and (ii) genetically modifying at least some of the cells of said micro-organ explant with a recombinant gene to express said at least one recombinant gene product.

2. The method of claim 1, wherein said micro-organ explant is derived from said recipient.

3. The method of claim 1, wherein said micro-organ explant is derived from said donor subject.

4. The method of claim 1, wherein said micro-organ explant is derived from a human being.

5. The method of claim 1, wherein said micro-organ explant is derived from a non-human animal.

6. The method of claim 1, wherein the recipient is a human being.

7. The method of claim 1, wherein the recipient is a non-human animal.

8. The method of claim 1, wherein said at least one recombinant gene product is selected from the group consisting of a recombinant protein and a recombinant functional RNA molecule.

9. The method of claim 8, wherein said recombinant protein is normally produced by the organ from the micro-organ explant is derived.

10. The method of claim 8, wherein said recombinant protein is normally not produced by the organ from which the micro-organ explant is derived.

11. The method of claim 8, wherein said recombinant protein is selected from the group consisting of a protease, a lipase, a ribonuclease, a deoxyribonuclease, a blood clotting factor, a cytochrome p450 enzyme, a transcription factor and a MHC component.

12. The method of claim 8, wherein said recombinant protein is selected from the group consisting of a peptide, a glycoprotein and a lipoprotein.

13. The method of claim 8, wherein said recombinant protein is selected from the group consisting of insulin, trypsinogen, chymotrypsinogen, carboxypeptidase, triaclyglycerol lipase, phospholipase $A_2$, elastase, amylase, UDP glucuronyl transferase, ornithine transcarbanoylase, adenosine deaminase, serum thymic factor, thymic humoral factor, thymopoietin, thymosin $\alpha_1$, gastrin, secretin, cholecystokinin, somatostatin, substance P and growth hormone.

14. The method of claim 1, wherein said micro-organ explant comprises epithelial and connective tissue cells.

15. The method of claim 1, wherein the organ is skin, and the explant includes at least one hair follicle and at least one gland.

16. The method of claim 1, wherein the organ is a diseased skin, and the explant includes a population of hyperproliferative or neoproliferative cells from the diseased skin.

17. The method of claim 1, wherein said micro-organ explant is maintainable in a minimal medium.

18. The method of claim 1, wherein said micro-organ explant is maintainable in an artificial medium.

19. The method of claim 1, wherein said micro-organ explant is maintainable in a defined medium.

20. The method of claim 1, wherein at least a portion of said population of cells is transduced, transformed or transfected with a recombinant construct carrying a recombinant gene encoding said recombinant gene product.

21. The method of claim 20, wherein said recombinant construct is a virus vector selected from the group consisting of a recombinant hepatitis virus, a recombinant adeno virus, a recombinant adeno-associated virus, a recombinant papilloma virus, a recombinant retrovirus, a recombinant cytomegalovirus and a recombinant simian virus.

22. The method of claim 20, wherein said recombinant construct is a naked nucleic acid molecule.

23. The method of claim 1, wherein at least a portion of the population of cells are transformed with a foreign nucleic acid sequence via a transformation method selected from the group consisting of calcium-phosphate mediated transfection, DEAE-dextran mediated transfection, electroporation, liposome-mediated transfection, direct injection, and receptor-mediated uptake.

24. The method of claim 1, further comprising the step of encapsulating said micro-organ explant prior to said step (b).

25. The method of claim 1, wherein said micro-organ explant is maintainable in culture for at least about twenty-four hours.

* * * * *